(12) United States Patent
Gertner et al.

(10) Patent No.: US 8,363,783 B2
(45) Date of Patent: Jan. 29, 2013

(54) METHOD AND DEVICE FOR OCULAR ALIGNMENT AND COUPLING OF OCULAR STRUCTURES

(75) Inventors: Michael Gertner, Menlo Park, CA (US); Mark Arnoldussen, San Carlos, CA (US); Matt Herron, Palo Alto, CA (US); Junzhong Liang, Fremont, CA (US)

(73) Assignee: Oraya Therapeutics, Inc., Newark, CA (US)

( * ) Notice: Subject to any disclaimer, the term of this patent is extended or adjusted under 35 U.S.C. 154(b) by 1214 days.

(21) Appl. No.: 12/103,534

(22) Filed: Apr. 15, 2008

(65) Prior Publication Data

US 2009/0163898 A1    Jun. 25, 2009

Related U.S. Application Data

(63) Continuation-in-part of application No. 12/027,069, filed on Feb. 6, 2008, and a continuation-in-part of application No. 12/027,083, filed on Feb. 6, 2008, and a continuation-in-part of application No. 12/027,094, filed on Feb. 6, 2008.

(60) Provisional application No. 61/016,472, filed on Dec. 23, 2007, provisional application No. 61/020,655, filed on Jan. 11, 2008.

(51) Int. Cl.
*A61N 5/10* (2006.01)
(52) U.S. Cl. .......................................... 378/65; 351/206
(58) Field of Classification Search .................... 378/65, 378/205; 606/4; 351/206, 246
See application file for complete search history.

(56) References Cited

U.S. PATENT DOCUMENTS

| | | | |
|---|---|---|---|
| 3,073,960 | A | 1/1963 | Guentner et al. |
| 4,391,275 | A | 7/1983 | Fankhauser et al. |
| 4,521,905 | A | 6/1985 | Hosokawa |
| 4,710,193 | A | 12/1987 | Volk |
| 4,718,418 | A | 1/1988 | L'Esperance, Jr. |
| 4,817,432 | A | 4/1989 | Wallace et al. |
| 5,008,907 | A | 4/1991 | Norman et al. |
| 5,027,818 | A | 7/1991 | Bova et al. |

(Continued)

FOREIGN PATENT DOCUMENTS

| EP | 2152145 A1 | 2/2010 |
|---|---|---|
| EP | 2231277 A1 | 9/2010 |

(Continued)

OTHER PUBLICATIONS

International Search Report and Written Opinion for PCT/US2008/013886, search report dated May 22, 2009, 19 pages (2009).

(Continued)

*Primary Examiner* — Courtney Thomas
(74) *Attorney, Agent, or Firm* — James W. Hill; M. Todd Hales; McDermott Will & Emery LLP

(57) ABSTRACT

Embodiments provide method and systems for determining or measuring objective eye alignment in an external-coordinate system so as to define a reference axis. Additional embodiments provide a method and system of aligning an objectively determined reference axis of the eye in a selected relationship to a therapeutic axis of an ophthalmic therapeutic apparatus and/or a diagnostic axis of an ophthalmic diagnostic apparatus. Embodiments provide a method and system for planning an ophthalmic treatment procedure based on objective eye alignment in an external-coordinate system so as to define a reference axis of an eye to be treated. The reference axis may be used to position a therapeutic energy component, for example, an orthovoltage X-ray treatment device, e.g., positioned to provide treatment to tissue on the retina, such as the macula.

47 Claims, 23 Drawing Sheets

U.S. PATENT DOCUMENTS

| | | |
|---|---|---|
| 5,065,031 A | 11/1991 | Moscovitch |
| 5,116,115 A | 5/1992 | Lange et al. |
| 5,139,494 A | 8/1992 | Freiberg |
| 5,171,254 A | 12/1992 | Sher |
| 5,189,687 A | 2/1993 | Bova et al. |
| 5,207,223 A | 5/1993 | Adler |
| 5,216,255 A | 6/1993 | Weidlich |
| 5,304,167 A | 4/1994 | Freiberg |
| 5,336,215 A | 8/1994 | Hsueh et al. |
| 5,339,347 A | 8/1994 | Slatkin et al. |
| 5,354,323 A | 10/1994 | Whitebook |
| 5,373,844 A | 12/1994 | Smith et al. |
| 5,411,026 A | 5/1995 | Carol |
| 5,422,926 A | 6/1995 | Smith et al. |
| 5,427,097 A | 6/1995 | Depp |
| 5,430,308 A | 7/1995 | Feichtner et al. |
| 5,446,548 A | 8/1995 | Gerig et al. |
| 5,468,238 A | 11/1995 | Mersch |
| 5,528,652 A | 6/1996 | Smith et al. |
| 5,556,417 A | 9/1996 | Sher |
| 5,635,721 A | 6/1997 | Bardi et al. |
| 5,644,616 A | 7/1997 | Landi et al. |
| 5,651,043 A | 7/1997 | Tsuyuki et al. |
| 5,668,847 A | 9/1997 | Hernandez |
| 5,708,696 A | 1/1998 | Kantor |
| 5,724,400 A | 3/1998 | Swerdloff et al. |
| 5,727,042 A | 3/1998 | Brenneisen |
| 5,737,384 A | 4/1998 | Fenn |
| 5,744,919 A | 4/1998 | Mishin et al. |
| 5,745,545 A | 4/1998 | Hughes |
| 5,771,270 A | 6/1998 | Archer et al. |
| 5,778,043 A | 7/1998 | Cosman |
| 5,820,553 A | 10/1998 | Hughes |
| 5,870,697 A | 2/1999 | Chandler et al. |
| 5,901,199 A | 5/1999 | Murphy et al. |
| 6,001,054 A | 12/1999 | Regulla et al. |
| 6,104,778 A | 8/2000 | Murad |
| 6,126,668 A | 10/2000 | Bair et al. |
| 6,134,294 A | 10/2000 | Gibbs |
| 6,135,996 A | 10/2000 | Kolesa et al. |
| 6,144,875 A | 11/2000 | Schweikard et al. |
| 6,149,643 A | 11/2000 | Herekar et al. |
| 6,179,422 B1 | 1/2001 | Lai |
| 6,245,059 B1 | 6/2001 | Clapham |
| 6,257,722 B1 | 7/2001 | Toh |
| 6,260,005 B1 | 7/2001 | Yang et al. |
| 6,278,764 B1 | 8/2001 | Barbee, Jr. et al. |
| 6,287,299 B1 | 9/2001 | Sasnett et al. |
| 6,299,054 B1 | 10/2001 | Gibbs, Jr. |
| 6,299,307 B1 | 10/2001 | Oltean et al. |
| 6,301,328 B1 | 10/2001 | Sliski et al. |
| 6,301,329 B1 | 10/2001 | Surridge |
| 6,312,393 B1 | 11/2001 | Abreu |
| 6,359,963 B1 | 3/2002 | Cash |
| 6,373,571 B1 | 4/2002 | Juhasz et al. |
| 6,385,286 B1 | 5/2002 | Fitchard et al. |
| 6,405,072 B1 | 6/2002 | Cosman |
| 6,436,113 B1 | 8/2002 | Burba et al. |
| 6,459,762 B1 | 10/2002 | Wong et al. |
| 6,494,878 B1 | 12/2002 | Pawlowski et al. |
| 6,501,981 B1 | 12/2002 | Schweikard et al. |
| 6,512,813 B1 | 1/2003 | Krispel et al. |
| 6,535,574 B1 | 3/2003 | Collins et al. |
| 6,544,193 B2 | 4/2003 | Abreu |
| 6,560,312 B2 | 5/2003 | Cash |
| 6,621,889 B1 | 9/2003 | Mostafavi |
| 6,690,965 B1 | 2/2004 | Riaziat et al. |
| 6,714,620 B2 | 3/2004 | Caflisch et al. |
| 6,728,335 B1 | 4/2004 | Thomson et al. |
| 6,744,846 B2 | 6/2004 | Popescu et al. |
| 6,778,850 B1 | 8/2004 | Adler et al. |
| 6,789,900 B2 | 9/2004 | Van de Velde |
| 6,792,073 B2 | 9/2004 | Deasy et al. |
| 6,810,107 B2 | 10/2004 | Steinberg |
| 6,837,862 B2 | 1/2005 | Driver, Jr. |
| 6,853,704 B2 | 2/2005 | Collins et al. |
| 6,863,667 B2 | 3/2005 | Webb et al. |
| 6,865,253 B2 | 3/2005 | Blumhofer et al. |
| 6,865,254 B2 | 3/2005 | Nafstadius |
| 6,875,165 B2 | 4/2005 | Dejuan, Jr. et al. |
| 6,888,919 B2 | 5/2005 | Graf et al. |
| 6,937,696 B1 | 8/2005 | Mostafavi |
| 6,942,656 B2 | 9/2005 | Pawlowski et al. |
| 6,965,847 B2 | 11/2005 | Wessol et al. |
| 6,977,987 B2 | 12/2005 | Yamashita et al. |
| 6,990,175 B2 | 1/2006 | Nakashima et al. |
| 7,018,376 B2 | 3/2006 | Webb et al. |
| 7,027,557 B2 | 4/2006 | Llacer |
| 7,044,602 B2 | 5/2006 | Chernyak |
| 7,046,762 B2 | 5/2006 | Lee |
| 7,046,765 B2 | 5/2006 | Wong et al. |
| 7,070,327 B2 | 7/2006 | Collins |
| 7,070,554 B2 | 7/2006 | White et al. |
| 7,085,347 B2 | 8/2006 | Mihara et al. |
| 7,103,144 B2 | 9/2006 | Wong et al. |
| 7,103,145 B2 | 9/2006 | Wong et al. |
| 7,115,120 B2 | 10/2006 | Lin |
| 7,139,601 B2 | 11/2006 | Bucholz et al. |
| 7,154,991 B2 | 12/2006 | Earnst et al. |
| 7,158,607 B2 | 1/2007 | Dimanian et al. |
| 7,158,610 B2 | 1/2007 | Mostafavi |
| 7,166,852 B2 | 1/2007 | Saracen et al. |
| 7,171,257 B2 | 1/2007 | Thomson |
| 7,179,254 B2 | 2/2007 | Pendekanti et al. |
| 7,187,792 B2 | 3/2007 | Fu et al. |
| 7,194,063 B2 | 3/2007 | Dilmanian et al. |
| 7,204,640 B2 | 4/2007 | Fu et al. |
| 7,221,733 B1 | 5/2007 | Takai et al. |
| 7,225,012 B1 | 5/2007 | Susil et al. |
| 7,227,925 B1 | 6/2007 | Mansfield et al. |
| 7,231,076 B2 | 6/2007 | Fu et al. |
| 7,239,684 B2 | 7/2007 | Hara et al. |
| 7,239,908 B1 | 7/2007 | Alexander et al. |
| 7,260,426 B2 | 8/2007 | Schweikard et al. |
| 7,266,176 B2 | 9/2007 | Allison et al. |
| 7,278,787 B2 | 10/2007 | Hack et al. |
| 7,280,865 B2 | 10/2007 | Adler et al. |
| 7,283,610 B2 | 10/2007 | Low et al. |
| 7,346,144 B2 | 3/2008 | Hughes et al. |
| 7,418,079 B2 | 8/2008 | Schildkraut et al. |
| 7,453,983 B2 | 11/2008 | Schildkraut et al. |
| 7,453,984 B2 | 11/2008 | Chen et al. |
| 7,496,174 B2 | 2/2009 | Gertner et al. |
| 7,505,559 B2 | 3/2009 | Kuduvalli |
| 7,535,991 B2 | 5/2009 | Gertner |
| 7,564,946 B2 | 7/2009 | Gertner |
| 7,587,024 B2 | 9/2009 | Grozinger et al. |
| 7,590,219 B2 | 9/2009 | Maurer et al. |
| 7,620,144 B2 | 11/2009 | Bodduluri |
| 7,620,147 B2 | 11/2009 | Gertner et al. |
| 7,672,429 B2 | 3/2010 | Urano et al. |
| 7,680,244 B2 | 3/2010 | Gertner et al. |
| 7,680,245 B2 | 3/2010 | Gertner |
| 7,693,258 B2 | 4/2010 | Gertner |
| 7,693,259 B2 | 4/2010 | Gertner |
| 7,693,260 B2 | 4/2010 | Gertner et al. |
| 7,697,663 B2 | 4/2010 | Gertner |
| 7,792,249 B2 | 9/2010 | Gertner et al. |
| 7,801,271 B2 | 9/2010 | Gertner et al. |
| 7,822,175 B2 | 10/2010 | Gertner et al. |
| 7,831,073 B2 | 11/2010 | Fu et al. |
| 7,894,649 B2 | 2/2011 | Fu et al. |
| 7,912,178 B2 | 3/2011 | Gertner |
| 7,912,179 B2 | 3/2011 | Gertner et al. |
| 7,953,203 B2 | 5/2011 | Gertner et al. |
| 7,961,845 B2 | 6/2011 | Gertner et al. |
| 7,978,818 B2 | 7/2011 | Gertner et al. |
| 7,978,819 B2 | 7/2011 | Gertner et al. |
| 2002/0051513 A1 | 5/2002 | Pugachev et al. |
| 2002/0065461 A1 | 5/2002 | Cosman |
| 2002/0099363 A1 | 7/2002 | Woodward et al. |
| 2002/0106054 A1 | 8/2002 | Caflisch et al. |
| 2002/0106055 A1 | 8/2002 | Cash |
| 2002/0115902 A1 | 8/2002 | Dejuan et al. |
| 2002/0131556 A1 | 9/2002 | Steinberg |
| 2002/0161356 A1 | 10/2002 | Bille et al. |
| 2002/0198453 A1 | 12/2002 | Herrick, II |

| | | |
|---|---|---|
| 2002/0198553 A1 | 12/2002 | Schumer et al. |
| 2003/0112922 A1 | 6/2003 | Burdette et al. |
| 2003/0120141 A1 | 6/2003 | Adler |
| 2003/0125622 A1 | 7/2003 | Schweikard et al. |
| 2003/0161826 A1 | 8/2003 | Arnason et al. |
| 2003/0189689 A1 | 10/2003 | Rathjen |
| 2003/0211075 A1 | 11/2003 | Thorpe et al. |
| 2003/0219098 A1 | 11/2003 | McNutt et al. |
| 2004/0019274 A1 | 1/2004 | Galloway, Jr. et al. |
| 2004/0037390 A1 | 2/2004 | Mihara et al. |
| 2004/0054359 A1 | 3/2004 | Ruiz et al. |
| 2004/0071261 A1 | 4/2004 | Earl et al. |
| 2004/0131150 A1 | 7/2004 | Pankratov et al. |
| 2004/0138515 A1 | 7/2004 | White et al. |
| 2004/0267294 A1 | 12/2004 | Will |
| 2005/0010109 A1 | 1/2005 | Faul |
| 2005/0049478 A1 | 3/2005 | Kuduvalli et al. |
| 2005/0058245 A1 | 3/2005 | Ein-Gal |
| 2005/0111621 A1 | 5/2005 | Riker et al. |
| 2005/0175218 A1 | 8/2005 | Vertegaal et al. |
| 2005/0180544 A1 | 8/2005 | Sauer et al. |
| 2005/0192562 A1 | 9/2005 | Loesel et al. |
| 2005/0203499 A1 | 9/2005 | Pendekanti et al. |
| 2005/0226482 A1 | 10/2005 | Kuduvalli |
| 2005/0228255 A1 | 10/2005 | Saracen et al. |
| 2005/0234327 A1 | 10/2005 | Saracen et al. |
| 2005/0270486 A1 | 12/2005 | Teiwes et al. |
| 2005/0271590 A1 | 12/2005 | Schwartz et al. |
| 2006/0002601 A1 | 1/2006 | Fu et al. |
| 2006/0002615 A1 | 1/2006 | Fu et al. |
| 2006/0002630 A1 | 1/2006 | Fu et al. |
| 2006/0002631 A1 | 1/2006 | Fu et al. |
| 2006/0002632 A1 | 1/2006 | Fu et al. |
| 2006/0004281 A1 | 1/2006 | Saracen |
| 2006/0033044 A1 | 2/2006 | Gentry et al. |
| 2006/0067469 A1 | 3/2006 | Dooley et al. |
| 2006/0072821 A1 | 4/2006 | Wang |
| 2006/0074292 A1 | 4/2006 | Thomson et al. |
| 2006/0074299 A1 | 4/2006 | Sayeh |
| 2006/0074304 A1 | 4/2006 | Sayeh |
| 2006/0078087 A1 | 4/2006 | Forman et al. |
| 2006/0084952 A1 | 4/2006 | Pallikaris et al. |
| 2006/0093089 A1 | 5/2006 | Vertatschitsch et al. |
| 2006/0170679 A1 | 8/2006 | Wang et al. |
| 2006/0170865 A1 | 8/2006 | Hirohara et al. |
| 2006/0176997 A1 | 8/2006 | Dilmanian et al. |
| 2006/0182326 A1 | 8/2006 | Schildkraut et al. |
| 2006/0192921 A1 | 8/2006 | Loesel et al. |
| 2006/0193441 A1 | 8/2006 | Cadman |
| 2006/0199991 A1 | 9/2006 | Lewis et al. |
| 2006/0203964 A1 | 9/2006 | Nyholm et al. |
| 2006/0245543 A1 | 11/2006 | Earnst et al. |
| 2006/0271025 A1 | 11/2006 | Jones et al. |
| 2006/0274061 A1 | 12/2006 | Wang et al. |
| 2006/0274885 A1 | 12/2006 | Wang et al. |
| 2006/0274924 A1 | 12/2006 | West et al. |
| 2006/0274925 A1 | 12/2006 | West et al. |
| 2006/0285641 A1 | 12/2006 | Scherch |
| 2006/0287662 A1 | 12/2006 | Berry et al. |
| 2006/0291621 A1 | 12/2006 | Yan et al. |
| 2006/0291710 A1 | 12/2006 | Wang et al. |
| 2006/0293583 A1 | 12/2006 | Saracen et al. |
| 2007/0003007 A1 | 1/2007 | Carrano et al. |
| 2007/0003123 A1 | 1/2007 | Fu et al. |
| 2007/0015991 A1 | 1/2007 | Fu et al. |
| 2007/0038058 A1 | 2/2007 | West et al. |
| 2007/0053490 A1 | 3/2007 | Wang et al. |
| 2007/0053491 A1 | 3/2007 | Schildkraut et al. |
| 2007/0071168 A1 | 3/2007 | Allison et al. |
| 2007/0071176 A1 | 3/2007 | Main et al. |
| 2007/0078306 A1 | 4/2007 | Allison et al. |
| 2007/0083087 A1 | 4/2007 | Carda |
| 2007/0093795 A1 | 4/2007 | Melcher et al. |
| 2007/0118010 A1 | 5/2007 | Hillstead et al. |
| 2007/0127622 A1 | 6/2007 | Main et al. |
| 2007/0127845 A1 | 6/2007 | Fu et al. |
| 2007/0140413 A1 | 6/2007 | Saracen |
| 2007/0169265 A1 | 7/2007 | Saracen et al. |
| 2007/0195929 A1 | 8/2007 | Ruchala et al. |
| 2007/0225691 A1 | 9/2007 | Silvestrini et al. |
| 2007/0225693 A1 | 9/2007 | Muehlhoff et al. |
| 2007/0249911 A1 | 10/2007 | Simon |
| 2008/0049896 A1 | 2/2008 | Kuduvalli |
| 2008/0056434 A1 | 3/2008 | Grozinger et al. |
| 2008/0159478 A1 | 7/2008 | Keall et al. |
| 2008/0187099 A1 | 8/2008 | Gertner |
| 2008/0187101 A1 | 8/2008 | Gertner |
| 2008/0192892 A1 | 8/2008 | Dilmanian et al. |
| 2008/0212737 A1 | 9/2008 | D'Souza et al. |
| 2008/0212738 A1 | 9/2008 | Gertner |
| 2008/0317312 A1 | 12/2008 | Carl et al. |
| 2009/0003525 A1 | 1/2009 | Gertner et al. |
| 2009/0163898 A1 | 6/2009 | Gertner et al. |
| 2009/0182310 A1 | 7/2009 | Gertner et al. |

FOREIGN PATENT DOCUMENTS

| | | |
|---|---|---|
| JP | 2002-540837 A | 12/2002 |
| JP | 2007-501057 A | 1/2007 |
| JP | 2007-509668 A | 4/2007 |
| JP | 4436139 B2 | 1/2010 |
| JP | 4602356 B2 | 10/2010 |
| WO | 9527453 A1 | 10/1995 |
| WO | 00/59395 A1 | 10/2000 |
| WO | WO-0126591 A1 | 4/2001 |
| WO | WO-0235996 A1 | 5/2002 |
| WO | 03/008543 A | 1/2003 |
| WO | WO-03/039370 A1 | 5/2003 |
| WO | 2005/016258 A2 | 2/2005 |
| WO | 2005/049139 A1 | 6/2005 |
| WO | 2005/079294 A2 | 9/2005 |
| WO | WO-2006086631 A2 | 8/2006 |
| WO | WO-2007/027164 | 3/2007 |
| WO | 2007/045075 A1 | 4/2007 |
| WO | 2008/124801 A2 | 10/2008 |
| WO | 2008/150330 A1 | 12/2008 |
| WO | 2009/075714 A1 | 6/2009 |

OTHER PUBLICATIONS

Preliminary Amendment for U.S. Appl. No. 12/027,069, filed Feb. 6, 2008, 94 pages (2008).
Preliminary Amendment U.S. Appl. No. 12/027,083, filed Feb. 6, 2008, 105 pages (2008).
Preliminary Amendment U.S. Appl. No. 12/027,094, filed Feb. 6, 2008, 111 pages (2008).
Preliminary Amendment U.S. Appl. No. 12/262,031, filed Oct. 30, 2008, 163 pages (2008).
U.S. Appl. No. 12/338,634, filed Dec. 18, 2008, 244 pages (2008).
Bogner, J. et al. 2003. A Noninvasive Eye Fixation and Computer-Aided Eye Monitoring System for Linear Accelerator-Based Stereotactic Radiotherapy of Uveal Melanoma. International Journal of Radiation Oncology Biology Physics, vol. 56, No. 4, Jun. 20, 2001, pp. 1128-1136.
Petersch, B. et al. 2004. Automatic Real-Time Surveillance of Eye Position and Gating for Stereotactic Radiotherapy of Uveal Melanoma. Medical Physics, vol. 31, No. 12, Nov. 24, 2004, pp. 3521-3527.
Extended European Search Report, dated Jun. 1, 2011, for European Patent Application No. 08743035.1, which entered the European Regional Phase on Dec. 3, 2009, Applicant Oraya Therapeutics, entitled "Device and Assembly for Positioning, Stabilizing and Treating an Eye," based on PCT Application No. PCT/US2008/004999.
Extended European Search Report, dated Jun. 15, 2011, for European Patent Application No. 08743125.0, which entered the European Regional Phase on Dec. 3, 2009, Applicant Oraya Therapeutics, entitled "Method and Device for Ocular Alignment and Coupling of Ocular Structures," based on PCT Application No. PCT/US2008/005101.
Bangerter, A. and Jager, T., "Forty Years' Experience with a Special, Non-Tumorous Application of Radiotherapy for the Eye", *European Journal of Medical Research*, 1:582-588 (1996).
California Department of Health and Human Services, Bailey Edgar D., C.H.P., Chief Radiologic Health Branch, *Syllabus on Radiography, Radiation Protection*, Filtration Regulatory Requirements, pp. 11-12 (2004).

Marcus et al., "External Beam Irradiation of Subfoveal Choroidal Neovascularization Complicating Age-Related Macular Degeneration", *Arch Ophthalmology*, 119:171-180 (2001).

Marcus, D.M. and The Amdrt Research Group, "The Age-Related Macular Degeneration Radiotherapy Trial (AMDRT): On e Year Results From a Pilot Study", *American Journal of Ophthalmology*, 138:818-828 (2004).

Sagerman, R.H. and Alberti, W.E., *Radiotherapy of Intraocular and Orbital Tumors* , 2$^{nd}$ Revised Edition, Springer, Chapter 24, Radiation Techniques for the Treatment of Retinoblastoma and Orbital Tumors, pp. 233-237 (2003).

Schilling et al., "Long Term Results After Low Dose Ocular Irradiation for Choroidal Haemangiomas", *British Journal of Ophthalmology*, 81:267-273 (1997).

Schipper, J. and Tan, K.E., "Management of Retinoblastoma by Precision Megavoltage Irradiation" *Department of Radiation Therapy of the University Hospital and the Royal Dutch Eye Hospital*, Utrecht, The Netherlands, 534-540 (1983).

Senan, S. and Smit, E.F., "Design of Clinical Trials of Radiation Combined with Antiangiogenic Therapy", *The Oncologist*, 12:465-477 (2007).

Toma et al., "External Bean Radiotherapy for Retinoblastoma:II Lens Sparing Technique", *British Journal of Ophthalmology*, 79:112-117 (1995).

International Search Report and Written Opinion for PCT/US2008/004999, search report dated Sep. 2, 2008, 9 pages (2008).

International Search Report and Written Opinion for PCT/US2008/005101, search report dated Sep. 2, 2008, 11 pages (2008).

Jaywant, S.E. et al., "Stereotactic Radiotherapy in the Treatment if Ocular Melanoma: A Noninvasive Eye Fixation Aid and Tracking System", *Journal of Applied Clinical Medical Physics*, 4(2):156-161 (2003).

Dieckmann et al., "A Linac-Based Stereotactic Irradiation Technique of Uveal Melanoma," Radiotherapy and Oncology, 61:49-56 (2001).

Gao et al., "Orthovoltage radiation therapy treatment planning using Monte Carlo Simulation: treatment of Neuroendocrine carcinoma of the maxillary sinus", ISSN: 0031-9155; vol. 42, No. 12, pp. 2421-2433 (1997).

Kim et at "Combination hyperthermia and radiation therapy for malignant melanoma," Cancer, 50:478-482 (1982).

Kobayashi at al., Radiotherapy for subfoveal neovascularisation associated with pathological myopia: a pilot study., J. Ophth. 87:761-766 (2000).

Cornsweet, T.N. and Crane, H.D., "Accurate Two-Dimensional Eye Tracker Using First and Fourth Purkinje", *Journal of the Optical Society of America*, 63(8):921-928 (1973).

Das et al., "Small Fields: Nonequilibrium Radiation Dosimetry", *Medical Physics*, 35(1):206- 215 (2008).

Esquivel, Carlos Jr. et al., Novel low-kVp beamlet system for choroidal melanoma, *Radiation Oncology*, 1:36, 12 pages (2006).

Fakiris, Achilles J. et al., Gamma-Knife-Based Stereotactic Radiosurgery for Uveal Melanoma, *Stereotactic and Functional. Neurosurgery.*, 85:106-112 (2007).

Francescon et al., "Total Scatter Factors of Small Beans: A Multidetector and Monte Carlo Study", *Medical Physics*, 35(2):504-513 (2008).

Georgopoulos, Michael et al., Tumour Regression of Uveal Melanoma after Ruthenium-106 Brachytherapy or Stereotactic Radiotherapy with Gamma Knife or Linear Accelerator, *Ophthalmologica*, 217:315-319 (2003).

Kirwan, James F. et al., Effect of β radiation on success of glaucoma drainage surgery in South Africa: randomized controlled trial, *BMJ online*, BMJ doi:10.1136/bmj.38971.395301.7C (Oct. 5, 2006).

Kishi, Kazushi et al., Lead Contact Lens for Crystalline Lens Shielding in Electron Therapy for Eyelid Tumors, *Radiation Medicine*, 14(2):107-109 (1996).

International Search Report and Written Opinion for PCT/US2008/012341, search report dated Feb. 5, 2009, 21 pages (2009).

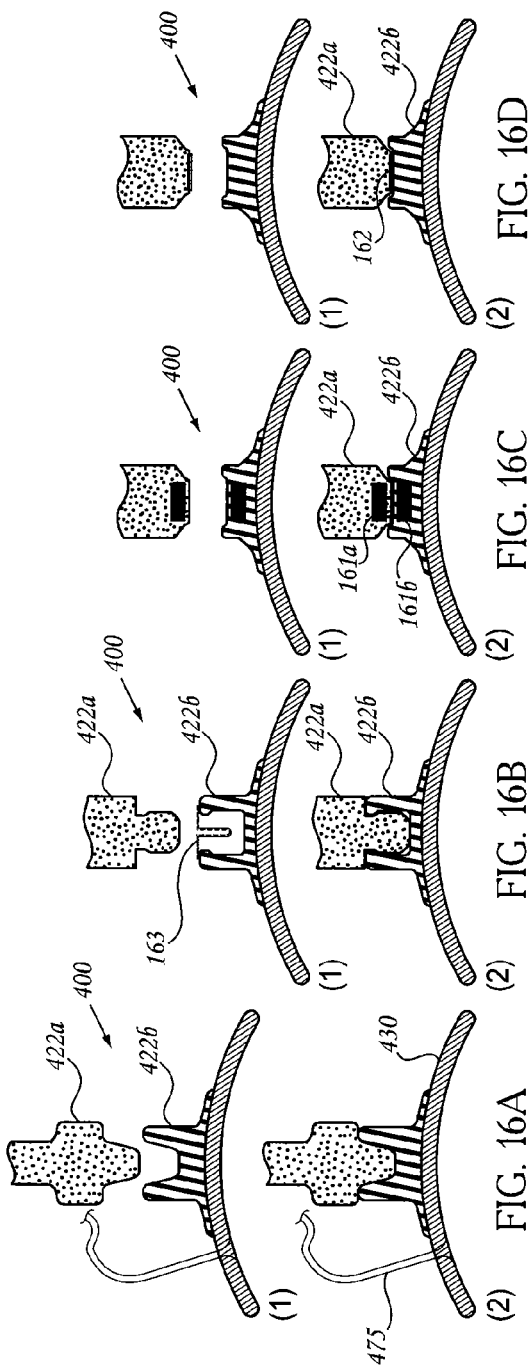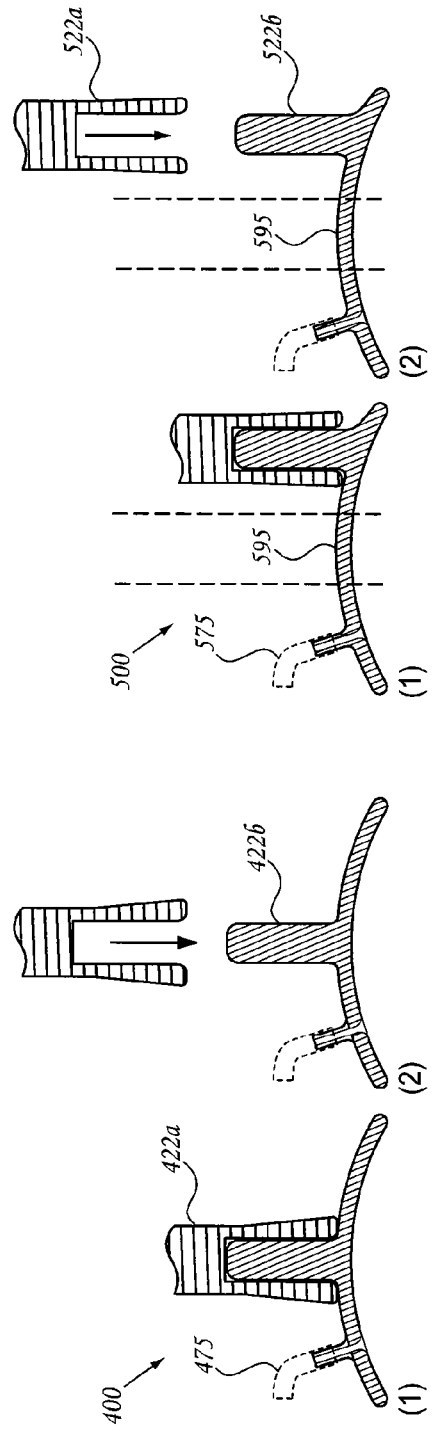

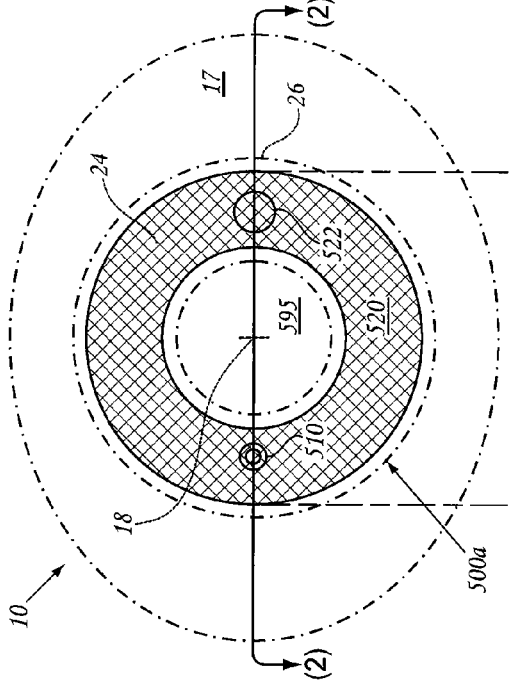
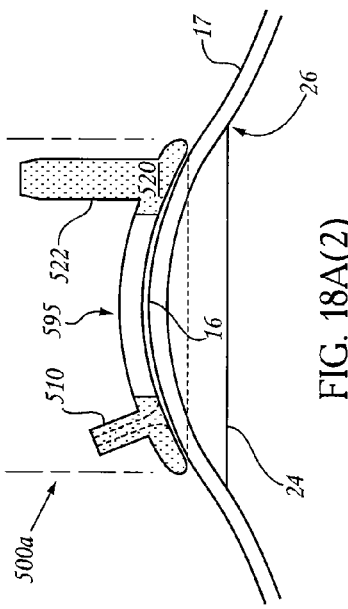
FIG. 18A(1)
FIG. 18A(2)
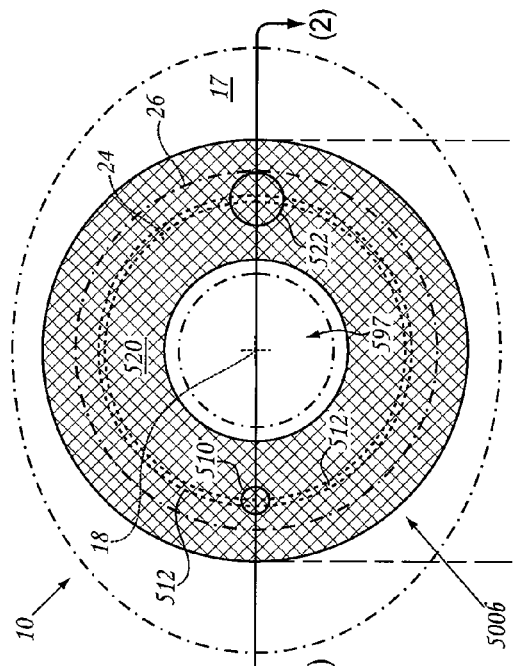
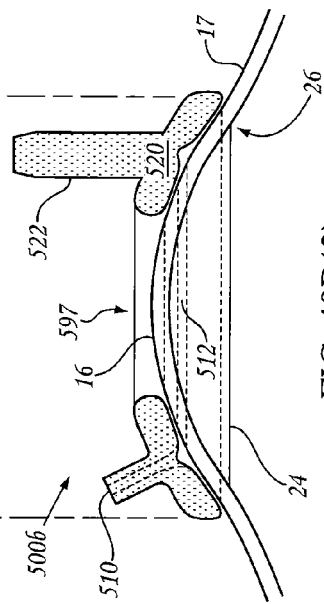
FIG. 18B(1)
FIG. 18B(2)

METHOD AND DEVICE FOR OCULAR ALIGNMENT AND COUPLING OF OCULAR STRUCTURES

This application claims the benefit of priority to U.S. Provisional Patent Applications No. 61/016,472 filed Dec. 23, 2007 and No. 61/020,655 filed Jan. 11, 2008. This Application also claims priority as a continuation-in-part of U.S. patent applications Ser. No. 12/027,069, Ser. No. 12/027,083, and Ser. No. 12/027,094, each filed Feb. 6, 2008. Each of the above applications is incorporated herein in its entirety by reference.

In addition, each of the following commonly-owned US applications are incorporated by reference in their entirety: No. 60/933,220 filed Jun. 4, 2007; Ser. No. 11/879,843 filed Jul. 18, 2007; Ser. No. 11/879,901 filed Jul. 18, 2007; Ser. No. 11/833,939 filed Aug. 3, 2007; Ser. No. 11/873,386 filed Oct. 16, 2007; Ser. No. 12/023,954 filed Jan. 31, 2008; Ser. No. 12/023,905 filed Jan. 31, 2008; Ser. No. 12/023,968 filed Jan. 31, 2008; Ser. No. 12/024,934 filed Feb. 1, 2008; Ser. No. 12/023,884 filed Jan. 31, 2008; and Ser. No. 12/026,507 filed Feb. 5, 2008; and Ser. No. 12/100,398 filed Apr. 9, 2008.

FIELD OF THE INVENTION

The invention relates to systems and methods for aligning the eye of a subject. More specifically, the invention relates to providing an imaging system and a method of use of an imaging system for determining objective eye alignment.

BACKGROUND OF THE INVENTION

Accurate alignment of a subject's eye is important in a number of situations. For example, when taking certain types of eye measurements, it is critical to know that the eye is in a particular reference position. When measuring the cornea of a patient's eye before therapeutic treatment, it can be important to repeat those measurements after the treatment to determine how much, if any, the treatment has affected the measurements. In order to accomplish this, one must ensure that the eye alignment is in the same position each time the particular measurements are made. Otherwise, the difference in data from before and after the treatment might be due to a change in eye alignment rather than the treatment.

In addition to those situations where one needs to ensure that the eye is aligned in the same position for two or more measurements, there are situations where eye alignment is desirable for diagnostic measurements of eye performance. There are situations when a human subject can simply be requested to fixate on a particular object. Thus, the human may state that he or she is currently looking at a light source, thereby providing "subjective" eye alignment information. However, there are situations where a physician or researcher would like "objective" eye alignment information indicating the orientation of the eye and, to the extent possible, indicating what the eye is viewing.

For example, very young children cannot be relied upon to fixate on such an object for measurements, such as refraction measurements which are very desirable to ensure that "in focus" images are being received when the child's brain is learning to interpret images. Likewise, adults subjected to extended eye examinations may become tired or subject to other duress and fail to maintain reliable fixation. A patient who is subjected to a therapeutic process such as laser ablation eye surgery may not be able to maintain desired eye orientation over an extended treatment time because of applied anesthesia, fatigue, or distraction by the procedure. Further, a research animal typically cannot be trained to fixate during eye measurements.

In each of the above cases, the failure or inability of the subject to maintain eye fixation upon an object can produce eye measurements or treatments that are seriously in error. Therefore, there are situations where absolute eye alignment data is needed (i.e., the eye is aligned in a certain manner) and situations where comparative eye alignment data (i.e., the eye is in the same alignment as when earlier measurements were taken) are needed and one cannot rely upon a subject maintaining the alignment.

A high level of accuracy is often required when performing surgery or other treatment on a part of the body that is subject to involuntary movement. It is typically a problem to align a patient's eye. The eye is predisposed to saccades, which are fast, involuntary movements of small magnitude. A patient may voluntarily shift their gaze during surgery, and furthermore, eye position stability is affected by the patient's heartbeat and other physiological factors. Moreover, there is still debate regarding the proper reference axis for alignment of the eye for treatment, such as laser refractive surgery.

In typical laser ophthalmic systems for treatment of defects or conditions, an eyetracker component of the system is utilized to track the motion of the eye during surgery, and to interrupt delivery of the therapeutic treatment when tracking cannot be maintained. Often, the surgeon will engage an eye tracker manually when it appears to be properly aligned. This subjective technique is prone to error which may lead to decentered ablations and other impediments to satisfactory vision correction. Various eye tracker technologies are commercially available. In some embodiments of the present invention described below, it is desirable to engage an eye tracker when it is locked onto the desired reference point on the eye.

Various types of visual axis detecting devices have been proposed. For example, some visual axis detecting devices are based on the patient's gaze. Japanese Patent Publication 1-274736, for example, describes a device which projects parallel light beams to an eyeball of an observer from a light source and determines a visual axis by making use of an image reflected from a cornea, that is, a cornea reflected image, or Purkinje image, and the imaging position of a pupil.

Thus, there is a need for more reliability and accuracy in eye alignment, particularly as it relates to eye treatment methods such as laser ophthalmic surgery.

SUMMARY OF THE INVENTION

Accordingly, it is an object of the invention to provide a method and system of determining or measuring objective eye alignment in an external-coordinate system so as to define a reference axis of a subject's eye. It is another object of the invention to provide a method and system of aligning an objectively determined reference axis of the eye in a selected relationship to a therapeutic axis of an ophthalmic therapeutic apparatus and/or a diagnostic axis of an ophthalmic diagnostic apparatus.

It is another object of the invention to provide an eye tracking method and system to monitors the movement of a patient's eye during an ophthalmic procedure, wherein the eye tracker system is automatically engaged upon determining objective eye alignment in an external coordinate system.

It is yet another object of the invention to provide a method and system for planning an ophthalmic treatment procedure based, at least in part, on objective eye alignment in an external-coordinate system so as to define a reference axis of an eye to be treated. It is yet another object of the invention to provide an ophthalmic treatment method and system, wherein a therapeutic energy component is controlled in one or more operative respects based on upon determining objective eye alignment in an external coordinate system.

It is yet another object of the invention to provide an ophthalmic treatment method and system, wherein a therapeutic energy component is positioned and/or stabilized with respect to a reference axis of an eye to be treated, defined by objective eye alignment in an external coordinate system. It is yet another object of the invention to provide an ophthalmic treatment method and system, wherein an objectively determined reference axis of an eye to be treated is positioned and/or stabilized with respect to a therapeutic energy component.

It is yet another object of the invention to provide an ophthalmic treatment system, wherein a therapeutic energy component is controlled in one or more operative respects based on upon determining objective eye alignment in an external coordinate system.

In one embodiment having aspects of the invention, a method is provided for determining when a subject's eye position is aligned with a reference axis in an external coordinate system, wherein the method comprises determining positions of the limbus (the generally circular sclera/cornea boundary) of the subject's eye in the external coordinate system, and from these positions, determining the center of the limbus in the external-coordinate system. The method further comprises determining the position of an image of a light beam reflected from the patient's eye (e.g., the cornea), and determining that the subject's eye is aligned with the reference axis when the determined position of the reflection is coincident with the determined center of the limbus.

In embodiments of this method, the determinations of limbus center and corneal reflection may be carried out with the patient's head stabilized in a head restraint, and may be carried out by an imaging system disposed in the external coordinate system. For example, the method may include recording an image of the subject's limbus by an optical detector, fitting the limbus image to a circle, and determining the position of the center of the circle with respect to the external coordinate system.

In some embodiments of this method, the reflection from the patient's eye is a first Purkinje image formed by reflection of a coherent or focused light beam off the anterior surface of the cornea. For example, the optical axis of the coherent or focused light beam may be aligned with the reference axis.

Some embodiments of this method include generating an eye-alignment signal when the subject's eye position is aligned with an external-coordinate reference axis. As an example, a signal may be generated upon a determination that the position of the corneal reflection is coincident with the center of the limbus. The method may include using this signal as an element of a procedure, such as using the eye-alignment signal to attach an ocular positioning and stabilizing device to the subject's eye; and/or using the eye-alignment signal to activate a therapeutic beam aimed along a path having a known relationship with the external-coordinate reference system. In some embodiments, the method is used in treating macular degeneration, for example wherein the therapeutic beam includes one or more low-energy collimated X-ray beams, which are aimed along a path that intersects the reference axis at a selected region of the subject's eye, e.g. at an intersection angle of between about 10 to about 45 degrees.

In some embodiments, the reference axis may define a geometric axis of the patient eye, and the method may include calculating the distance between the cornea and the retina along this axis.

In some embodiments, the method may be applied to determine the position of intersection of the reference axis with the patient's retina relative to a structure of interest on the retina. Additional steps may include determining the position of an image formed by a light beam reflected from the retina of the patient's eye. For example, a light beam used to obtain an anterior eye reflection, such as a first Purkinje image, may also be used to illuminate the retina, so as to obtain a retinal reflection image, such as when a first Purkinje image is coincident with the center of the limbus image and thus the retinal reflection image is aligned with the reference axis. Further, a second coherent or focused light beam may be passed through the pupil of the subject's eye to reflect off a structure of interest in the retina, and the position of the image of the reflection of the second beam off the structure of interest may be determined in the external coordinate system, relative to the axis of reference.

In yet another embodiment having aspects of the invention, a method is provided for defining a reference axis of a patient's eye in an external coordinate system, wherein the method comprises determining positions of the limbus of the patient's eye in the external coordinate system, and from these positions, determining the center of the limbus in the external-coordinate system. The method further comprises determining the position of an image of a light beam reflected from the cornea of the patient's eye, and adjusting the position of the eye until the position of the reflection is coincident with the center of the limbus, at which position an axis normal to the cornea at the corneal center defines the patient reference axis.

In some embodiments, the reference axis defined by the method extends from the cornea to a position on the retina which is a maximum distance from the cornea. The method may further include superimposing the patient reference axis on a three-dimensional model of the eye by aligning the patient reference axis with a model reference axis. In some embodiments, the method may be applied for conducting a diagnostic or therapeutic procedure on the eye, the method further including positioning a beam of a diagnostic or therapeutic device at a selected position and angle with respect to the patient reference axis.

Some embodiments of this method include generating an eye-alignment signal when the patient's eye position is aligned with an external-coordinate reference axis. The method may include using this signal to attach an ocular positioning and stabilizing device to the subject's eye. Alternatively or additionally, the method may include using the eye-alignment signal to activate a therapeutic beam aimed along a path having a known relationship with the external-coordinate reference system. In some embodiments, the method is used in treating macular degeneration, for example wherein the therapeutic beam is a low-energy collimated x-ray beam, and the therapeutic beam is aimed along a path that intersects the reference axis in a macular region of the subject patient's eye, and at an angle between about 10-45 degrees with respect to the reference axis.

In some embodiments, the method may be applied to determine the position of intersection of the reference axis with the patient's retina relative to a structure of interest on the retina, including determining the position of an image formed by a light beam reflected from the retina of the patient's eye, when a corneal refection of the light beam is coincident with the center of the limbus. Further, a second coherent or focused light beam may be passed through the pupil of the subject's eye to reflect off a structure of interest in the retina, and the position of the image of the reflection off the structure of interest may be determined in the external coordinate system.

In yet another embodiment having aspects of the invention, a system is provided of defining a reference axis of a patient's eye in an external coordinate system, wherein the system comprises (a) a head support for supporting the patient's head, (b) a light source for illuminating the sclera/cornea boundary (limbus) of the patient's eye, (c) a light source for directing a coherent or focused light beam on the cornea of the patient's eye, (d) an imaging system for recording an image of the patient's limbus and an image formed by reflection of the coherent or focused light beam from the cornea of the patient's eye, and (e) a processor operatively connected to the imaging system for (i) from the image of the sclera/cornea boundary, determining the center of the limbus of the patient's eye in the external-coordinate system, and (ii) from the image of the reflection of the coherent or focused light beam off the cornea, determining when the position of the reflection image is coincident with the center of the limbus image, at which position an axis normal to the cornea at the corneal center defines the reference axis.

In some system embodiments, the light source for illuminating the limbus is effective to illuminate the entire eye, and the light source for directing a coherent or focused light beam on the cornea is a coherent light beam. In some system embodiments, the imaging system includes a CCD photodetector. In some system embodiments, the processor operates to fit the image of the limbus to a circle, and find the center of the circle. Further, the processor may operate to determine, at each eye position of the patient eye, whether the center of the patient eye limbus is the same as the position of the reflection image from the cornea. In some system embodiments, the processor may operate to generate a signal when the position of the reflection image is coincident with the center of the limbus image. Further, the processor may operate to generate positioning signals for positioning a diagnostic or therapeutic device at a selected position and angle with respect to the reference axis.

In some embodiments, the system further operates to record reflections of a coherent or focused beam off of the surface of the retina, wherein the processor further operates to (iii) determine the position of an image formed by reflection of the light beam off the retina, when the position of the reflection image off the cornea is coincident with the center of the limbus image, (iv) determine the position of an image formed by reflection of another coherent or focused light beam off a selected structure of interest in the retina, and (v) determine the position of the image of the reflection of the other beam off the structure of interest in the external coordinate system, relative to the position of the image of the reflection off the retina along the reference axis.

In yet another embodiment having aspects of the invention, a method of is of placing a patient's eye in alignment with a reference axis in an external coordinate system is provided, comprising (a) placing an ocular guide on a patient's eye, (b) centering the guide with respect to the sclera/cornea boundary of the patient's eye, (c) stabilizing the ocular guide on the eye by applying a negative pressure between the guide and eye, (d) moving the ocular guide, and thus patient's eye, until the ocular guide is aligned with the reference axis, thus to place the patient's eye in alignment with the reference axis. The ocular guide may have a peripheral ring dimensioned to be contained within or substantially coincident with the sclera/cornea boundary of the patient's eye, and step (b) may include adjusting the position of the guide until the peripheral ring and sclera/cornea boundary are coaxially aligned.

In yet another embodiment having aspects of the invention, an image-guided ocular treatment system is provided, comprising (a) a head support for supporting a patient's head, (b) a eye guide adapted to be placed on the patient's eye, and stabilized on the eye by the application of negative pressure between the eye guide and eye when the guide is approximately centered with respect the sclera/cornea boundary of the patient's eye, (c) a camera for recording an image of the eye guide on the patient's eye, (d) a guide-alignment assembly for detecting alignment between the eye guide, with such stabilized on a patient's eye, and an external-coordinate reference axis, (e) an external arm pivotally attached to the eye guide to hold the eye at a position in which the eye guide is aligned with the external-coordinate reference axis, (e) a processor operatively connected to the camera and guide-alignment assembly for (i) determining from the image of eye guide and the sclera/cornea boundary, any variation from true centering of the eye guide on the patient's eye, (ii) if variation from true centering is determined, constructing a coordinate transform between the actual and centered positions of the eye guide, (iii) with the eye guide moved to and held at its aligned position, and applying the coordinate transform if necessary, determining the position of the eye with respect to the external-coordinate reference axis, (iv) from the determination in step (iii) determining a treatment axis or axes along which a therapeutic beam will be aimed at a target region of the eye, and (f) a display monitor operatively connected to the processor for displaying to the user, an image of the patient's eye and attached eye guide, information about the extent of alignment between the eye guide and reference beam, and a virtual image of the treatment axis or axis.

In some embodiments, the processor may include stored fundus images, and operates to superimpose those images on the image of the patient's eye displayed on the monitor, allowing the user to view the areas of intersection of the therapeutic beam axes and fundus.

These and other objects and features of the invention will be more fully appreciated when the following detailed description of the invention is read in conjunction with the accompanying figures.

BRIEF DESCRIPTION OF THE FIGURES

The figures and the associated descriptions are provided to illustrate embodiments of the disclosure and not to limit the scope of the disclosure. Throughout the figures, reference numbers are reused to indicate correspondence between referenced elements. The figures are in simplified form and are not necessarily precise in scale. In reference to the disclosure herein, for purposes of convenience and clarity only, directional terms, such as top, bottom, left, right, up, down, over, above, below, beneath, rear, and front are used with respect to the accompanying figures. Such directional terms are not to be construed as limiting the scope of the invention in any manner.

The particular figures may be briefly summarized as follows:

FIG. 3D is a detail frontal view of an eye as seen aligned with a system reference axis.

FIGS. 11A-B show a pair of fundus images obtained with the system as in FIG. 10, wherein FIG. 11A depicts an image in which the focus of the laser beacon and the laser beacon reflection are aligned with the center of the limbus, and FIG. 11A depicts an image in which the beacon is not aligned with the center of the limbus.

FIGS. 12A-B depict a summary of the methodology system having aspects of the invention, adapted to be used to deliver radiation therapy to the macula of a patient, wherein FIG. 12A is a diagram of the treatment system FIG. 12B shows a fundus image of the subject retina.

FIGS. 13A-C depict x-ray therapy beams traveling through an eye to a therapy center or target, wherein FIG. 13A shows in cross section the angular arrangement of the beams, FIG. 13B depicts a retinal image in which the radiation therapy center is centered about the treatment axis, and FIG. 13B depicts a retinal image in which the radiation therapy center is coincident with the macula and not the treatment axis.

FIGS. 16A-F depict alternative species having aspects of the invention of a "breakaway" post fitting which may be employed with eye positioning and/or stabilizing devices such as shown in FIGS. 4A-B and 5A-B.

FIGS. 18A(1)-18B(2) depict embodiments of eyeholders having aspects of the invention having alternative configurations of a contact member.

DETAILED DESCRIPTION OF THE INVENTION

Figure 1:
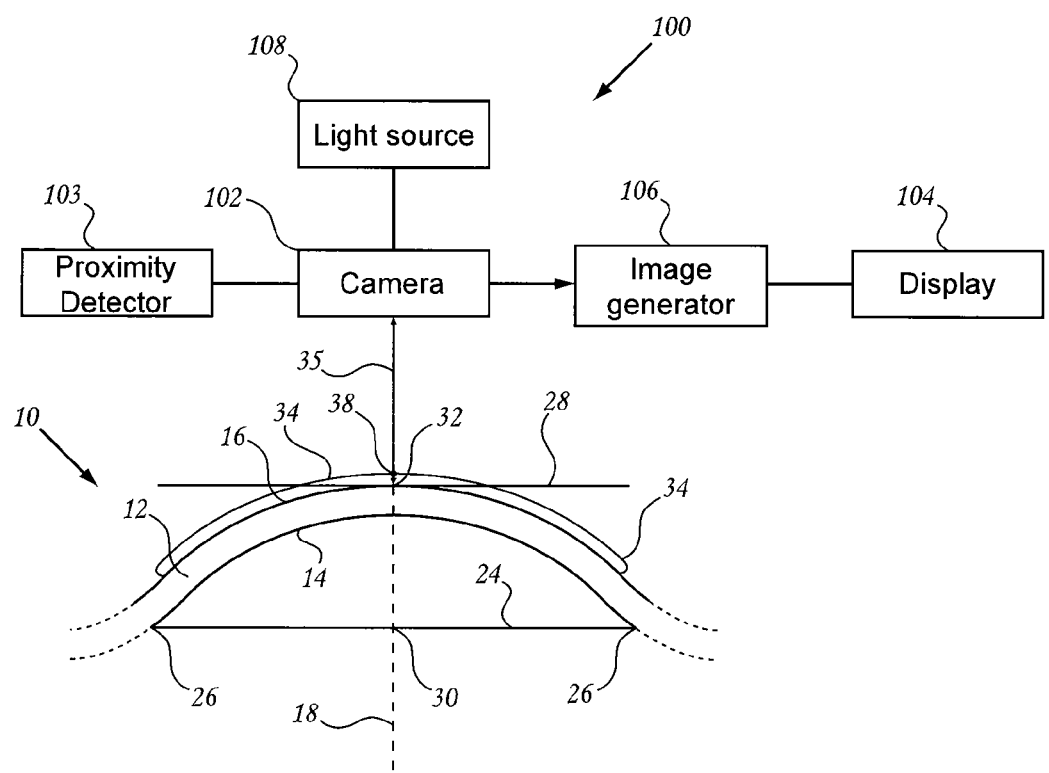
FIG. 1 illustrates a schematic side view of an anterior portion of an eye in association with an embodiment of an alignment system having aspects of the invention.

Reference will now be made in detail to disclosed embodiments of the invention, examples of which are illustrated in the accompanying figures.

I. Definitions

Unless otherwise indicated, all technical and scientific terms used herein have the same meaning as they would to one skilled in the art of the present invention. It is to be understood that this invention is not limited to the particular methodology and protocols described, as these may vary.

As used herein, "accommodation" refers to the ability to change focus from distant objects to near objects, which ability may tend to diminish with age.

The term choroid" refers to the highly vascular layer of the eye beneath the sclera.

As used herein, "ciliary muscle" refers to a muscular ring of tissue located beneath the sclera and attached to the lens via zonules.

As used herein, "conjunctiva" refers to the thin, transparent tissue covering the outside of the sclera. In some embodiments of the invention, reference is made to one or more devices or systems of the invention in contact with outer structures of the eye, such as the sclera. In these embodiments, it is to be understood that the device or systems of the invention may be in contact with the named structure, or may be in contact with the conjunctiva covering the structure.

As used herein, "cornea" refers to the transparent, avascular tissue that is continuous with the opaque sclera and semi-transparent conjunctiva, and covered by tear film, or corneal epithelium, on its anterior surface and bathed by aqueous humor on its posterior surface.

As used herein, "limbus" refers to the boundary where the cornea meets the sclera.

As used herein, "retina" refers to the light-sensitive layer of tissue that lines the inner back of the eye and sends visual impulses through the optic nerve to the brain.

As used herein "ocular disease" refers to a disease of the eye, including, but not limited to tumors, ocular degeneration, retinopathies, retinitis, retinal vasculopathies, diabetic retinopathies, diseases of the Bruch's membrane and the like.

As used herein, the term "reducing ocular disease" also encompasses treating and alleviating the ocular disease.

As used herein, "sclera" refers to the outer supporting structure, or "white," of the eye.

As used herein, the term "subject" refers to man or any animal that has an eye.

As used herein, "vitreous body" refers to the clear colorless transparent jelly that fills the eye posterior to the lens and that is enclosed by a hyaloid membrane.

As used herein, "zonules" refers to a circular assembly of radially directed collagenous fibers that are attached at their ends to the lens and at their outer ends to the ciliary muscle.

As used herein, the term "presbyopia," refers to the inability of the eye to focus sharply on nearby objects. Presbyopia is associated with advancing age and typically entails a decrease in accommodation. Introduction of treatment, e.g., laser ablation, according to any of the implementations described herein, preferably increases or facilitates an increase in accommodation, thereby mitigating effects of presbyopia.

The term "radiodynamic therapy" refers to the combination of collimated x-rays with a concomitantly administered systemic therapy.

The term "radiodynamic agents" is intended to have its ordinary and plain meaning, which includes, without limitation, agents that respond to radiation, such as x-rays, and agents that sensitize a tissue to the effects of radiation.

The term "photodynamic therapy" refers to a therapeutic or diagnostic method involving use of a photoreactive agent and radiation of a sufficient intensity and wavelength to activate the photoreactive agent. The activated photoreactive agent then, through emission of energy, exerts a therapeutic effect or allows for diagnosis through detection of emitted energy.

The term "photodynamic agents" is intended to have its plain and ordinary meaning, which includes, without limitation, agents that react to light and agents that sensitize a tissue to the effects of light.

"Radiation," as used herein, is intended to have its ordinary meaning, which includes, without limitation, at least any photonic-based electromagnetic radiation which covers the range from gamma radiation to radiowaves and includes x-ray, ultraviolet, visible, infrared, microwave, and radiowave energies. Therefore, planned and directed radiotherapy can be applied to an eye with energies in any of these wavelength ranges.

"Radiotherapy," as used herein, and is intended to have its ordinary meaning, which includes, without limitation, at least any type of clinical therapy that treats a disease by delivery of energy through electromagnetic radiation. X-ray radiation generally refers to photons with wavelengths below about 10 nm down to about 0.01 nm. Gamma rays refer to electromagnetic waves with wavelengths below about 0.01 nm. Ultraviolet radiation refers to photons with wavelengths from about 10 nm to about 400 nm. Visible radiation refers to photons with wavelengths from about 400 nm to about 700 nm. Photons with wavelengths above 700 nm are generally in the infrared radiation regions. Within the x-ray regime of electromagnetic radiation, low energy x-rays can be referred to as orthovoltage. While the exact photon energies included within the definition of orthovoltage varies, for the disclosure herein, orthovoltage refers at least to x-ray photons with energies from about 20 keV to about 500 keV.

As used herein, "treatment" refers to any manner in which one or more of the symptoms of a disease or disorder are ameliorated or otherwise beneficially altered. Treatment also encompasses any therapeutic use of the systems herein.

Diagnostics can also be performed with any type of energy source or treatment described herein and may be referred to as "radiation diagnostics."

As used herein, the term "global coordinate system" or "external coordinate system" refers to a physical world of a machine or room. The global coordinate system is generally a system relating a machine, such as a computer or other operating device, to the physical world or room that is used by the machine. The global coordinate system can be used, for example, to move a machine, components of a machine, or other elements from a first position to a second position. The global coordinate system can also be used, for example, to identify the location of a first item with respect to a second item.

"Kerma," as used herein, refers to the energy released (or absorbed) per volume of air when the air is hit with an x-ray beam. The unit of measure for Kerma is Gy. Air-kerma rate is the Kerma (in Gy) absorbed in air per unit time. Similarly, "tissue kerma" rate is the radiation absorbed in tissue per unit time. Kerma is generally agnostic to the wavelength of radiation, as it incorporates all wavelengths into its joules reading.

As used herein, the term "radiation dose" is meant to include, without limitation, absorbed energy per unit mass of tissue. One example of a measure of radiation dose is the Gray, which is equal to 1 joule per kilogram, which generally also equals 100 rad. For example, as used herein in some embodiments, a radiation dose may be the amount of radiation, or absorbed energy per unit mass of tissue, that is received or delivered during a particular period of time. For example, a radiation dose may be the amount of absorbed energy per unit mass of tissue during a treatment process, session, or procedure.

As used herein, the term "trajectory" is meant to include, without limitation, a general path, orientation, angle, or direction of travel. For example, as used herein in some embodiments, the trajectory of a light beam can include the actual or planned path of the light beam. In some embodiments, the trajectory of a light beam can be determined by an orientation of a light source that emits the light beam, and the trajectory can, in some embodiments, be measured, such as by an angle, or determined as with respect to a reference, such as an axis or plane.

As used herein, the term "geometric axis" refers to that axis which is the axis of symmetry of the eye in the anterior to posterior direction. This axis extends from the center of the cornea through to the center of the posterior pole of the eye and is that axis which the eye can be rotated around with rotational symmetry. The geometric axis is an axis purely related to ocular anatomy and can be determined in any eye, even in a blind patient.

As used herein, the term "optical axis" of the eye is taken to be generally synonymous with the term "geometric axis".

As used herein, the term "visual axis" is the axis which passes through the center of the lens to reach the center of the fovea. It is typically determined when the subject is looking directly at an object, the axis intersecting a region on the fovea. The visual axis is to an extent determined by patient-specific visual function, may be affected by eye pathology and adaptive patient behavior, and may be difficult to determine in some patients.

As used herein, the term "reference axis" refers to an axis which relates a subject's ocular anatomy to an external coordinate system, i.e., a coordinate system external to the eye, such as a coordinate system defined by an ophthalmologic treatment or diagnostic device (in some instances a reference axis may be referred to herein as an "axis of interest". In the embodiments described in particular detail herein, the reference axis generally is, or accurately approximates and represents, the geometric axis of the eye as referenced in an external coordinate system.

However, alternative reference axes may be defined, and it should be understood, that many aspects of the invention may be usefully applied, without departing from the spirit of the invention, to systems and methods in which the axis of interest is different than the geometric axis. For example, in certain embodiments having aspects of the invention the "axis of interest" may be the visual axis. Alternative embodiments may define an eye reference system with respect to a number of other observable and/or measurable eye structures or properties. Regardless of the eye axis being defined as a reference axis, it can be aligned with respect to an external coordinate system, and may serve as a reference axis for anatomic structures of the eye which may be of interest in diagnosis or treatment, such as a macula of the retina exhibiting macular degeneration.

As used herein, the term "aligned with" means to arrange in a line or so as to be coincident or parallel. In particular, a patient's eye position is aligned with a reference axis in an external coordinate system when the geometric axis of the eye is coincident with the reference axis.

The term "positioned with respect to" is meant to include, without limitation, having a fixed angular relationship between zero and 180 degrees. For example, as used herein, two light beams or x-ray beams are positioned with respect to each other if they are collinear, are oriented with respect to each other at a fixed angle, or have another fixed relationship. In some embodiments, the angle between aligned light beams or x-ray beams can range from about zero degrees to about 360 degrees, and can include about 90 degrees, about 180 degrees, and about 270 degrees.

"Beam axis" or "device axis", as used herein, is meant to include, without limitation, a characteristic directional axis of a treatment or diagnostic device, for example, an axis of propagation of a collimated or focused light beam and/or a collimated X-ray beam emitted by a device for treatment or diagnosis in some embodiments, a beam axis may be the axis of a collimated orthovoltage X-ray beam emitted by an X-ray device and used for treating a target tissue in an organ, such as an eye. Such an embodiment may also emit a collimated or focused laser beam which is co-linear with the X-ray beam, i.e., and also aligned with the beam axis.

"Treatment axis," as used herein, is meant to include, without limitation, an axis of an organ or anatomical structure in relation to a treatment device. For example, in some embodiments, the treatment axis of the organ is related, such as by an angle, to an characteristic axis of the treatment device (e.g., the beam axis of a treatment beam-emitting device). In some embodiments, the intersection of the treatment axis and the device axis is used to define the target for the radiotherapy beam.

As used herein, the term "treatment session" is meant to include, without limitation, a single or a plurality of administrations of therapeutic treatment of a target tissue, e.g., heat therapy and/or radiation therapy. For example, in some embodiments, a treatment session can include a single administration of x-ray beams to the eye. In some embodiments a treatment session can include a plurality of administrations of x-ray beams and laser radiation to the subject's eye. In some embodiments, a treatment session is limited to, for example, a single visit by a patient to a clinic for treatment, and in some embodiments, a treatment session can extend over a plurality of visits by a patient to the clinic. In some embodiments, a treatment session can include a single procedure of administering radiotherapy, and in some embodiments, a treatment session can include a plurality of procedures following different protocols for each procedure. In some embodiments, a treatment session may be limited to about a single day, and in some embodiments, a treatment session can be about 2 days, about 3 days, about 5 days, about 1 week, about 10 days, about 2 weeks, about 3 weeks, about 1 month, about 6 weeks, about 2 months, about 3 months, about 6 months, about 1 year, or longer.

As used herein, the term "treatment period" is meant to include, without limitation, any single or plurality of administrations of radiotherapy or related therapeutic treatment of tissue, and can include a single or plurality of treatment sessions.

As used herein, the term "orders of magnitude, is meant to include, without limitation, a class of scale or magnitude of any amount, where each class contains values of a ratio related to the class preceding it. For example, in some embodiments, the ratio relating each class may be 10. In these embodiments, one order of magnitude is a magnitude based on a multiple of 10, two orders of magnitude is based on two multiples of 10, or 100, and three orders of magnitude is based on three multiples of 10, 1000.

"Laser" energy is composed of photons of different energies ranging from short wavelengths, such as ultraviolet radiation, up to long wavelengths, such as infrared radiation. Laser refers more to the delivery mechanism than to the specific wavelength of radiation. Laser light is considered "coherent" in that the photons travel in phase with one another and with little divergence. Laser light is also collimated in that it travels with relatively little divergence as it proceeds in space. Light can be collimated without being coherent (in phase) and without being a laser; for example, lenses can be used to collimate non-x-ray light. X-ray light is typically collimated with the use of non-lens collimators, the penumbra defining the degree of successful collimation. Laser pointers are typically visualization tools, whereas larger, higher-flux lasers are utilized for therapeutic applications. In some embodiments of the systems and methods described herein, optics can be used, such as lenses or mirrors, and in some embodiments, there are no intervening optical elements, although collimators may be used.

The two eye chambers are the anterior and posterior chambers. The anterior chamber includes, among other things, the lens, the conjunctiva, the cornea, the sclera, the trabecular apparatus, the ciliary bodies, muscles, and processes, and the iris. The posterior chamber includes, among other structures, the vitreous humor, the retina, and the optic nerve.

"Ocular diseases," as used in this disclosure, is intended to have its ordinary meaning, which includes, without limitation, at least diseases of the anterior eye (e.g., glaucoma, presbyopia, cataracts, dry eye, conjunctivitis) as well as diseases of the posterior eye (e.g., retinopathies, age related macular degeneration, diabetic macular degeneration, and choroidal melanoma).

Drusen are hyaline deposits in Bruch's membrane beneath the retina. The deposits are caused by, or are at least markers of inflammatory processes. They are present in a large percentage of patients over the age of 70. Although causality is not known, drusen are associated with markers of the location where inflammation is occurring and where neovascularization has a high likelihood of occurring in the future; these are regions of so called "vulnerable retina." Therefore, applying inflammation-reducing radiation to the region is beneficial, in accordance with so me embodiments of the invention.

As used herein, Purkinje is a term used to denote a reflected image off a surface of the eye. For example, the first Purkinje refers to the reflection off the anterior surface of the cornea and the second Purkinje refers to the reflection off the posterior surface of the cornea.

II. Eye Alignment System and Method

One aspect of the invention is directed to systems and methods for objectively and accurately identifying and aligning a reference axis of a patient's eye. In the embodiments described in particular detail, the reference axis is, or accurately approximates and represents, the geometric axis of the eye, and therefore, the terms "geometric axis" and "reference axis" will frequently be used interchangeably. In these embodiments, the geometric axis of the eye is identified and aligned with reference to an external coordinate system.

In another aspect of the invention, the aligned eye can then be positioned relative to the beam axis or device axis of a diagnostic or a therapeutic component whose position is referenced to the common external coordinate system, such as an excimer laser of a refractive vision correction surgery system, an orthovoltage X-ray treatment system, or the like. Typically, the external coordinate system will be a 3-dimensional coordinate system for purposes of alignment of the eye, regardless of the particular degrees of freedom of motion that may be incorporated in the structure of a particular associated diagnostic or therapeutic device.

Aspects of the invention will find utility both in laboratory research and in clinical application. The advantages of the present invention are numerous. Exemplary advantages of the systems and methods described below include:

(i) providing objective eye alignment information which permits eye alignment relative to an external point or line, such as an instrument or device axis, or to provide eye alignment information by indicating when the present eye alignment is the same as an earlier eye alignment;

(ii) providing eye alignment data which can be used in combination with other diagnostic and therapeutic instruments;

(iii) allowing eye alignment data to be provided without requiring instrumentation, such as an eye guide, which could block or prevent use of diagnostic and/or therapeutic devices which may advantageously use eye alignment information for improving their diagnostic and/or therapeutic operations; and (iv) allowing one to bring the eye of a subject to a particular desired alignment, while the subject is under general anesthesia or is otherwise unable to cooperate in bringing their eye to a particular alignment, e.g., with use of an eye guide, the eye of a subject can be brought to a predetermined alignment.

Referring now to the figures, and more particularly to FIG. 1, a schematic side view of an anterior portion of an eye 10 is shown in association with a block diagram of an alignment system 100 having aspects of the invention. The alignment system and method in this embodiment of the invention is based on the detection of the co-alignment of the first Purkinje reflection from the subject's eye 10 with the center of the limbus 30 of the subject's eye. When the eye 10 is appropriately illuminated by a light source, four Purkinje reflections can be detected but the first (anterior cornea) is the brightest typically.

The elements of eye 10 necessary for understanding the present invention will be described briefly below. The cornea 12 of eye 10 is characterized by an anterior surface 16 and a posterior surface 14 that are concentric with one another. The remaining portions of eye 10 depicted in FIG. 1 are the iris 24 extending outward to posterior surface 14 of cornea 12. The circle of intersection between iris 24 and interior surface 14 is an anatomical landmark known as the limbus, the position indicated by reference numeral 26. The limbus 26 of an eye is visible from the outside and is readily imageable.

In embodiments having aspects of the invention, a reference axis may be defined by the co-alignment of the first, second, third, or fourth Purkinje reflection with the center of the limbus. The first Purkinje reflex is defined as the virtual image formed by the light reflected from the anterior surface 16 of the cornea 12. The second Purkinje reflex is an image of the input light formed by the reflection from the posterior corneal surface 14. The light that is not reflected from either the anterior corneal surface 16 or the posterior corneal surface 14 propagates through the cornea and aqueous humor, and through the lens of the eye onto the retina. The third Purkinje reflex is a virtual image formed by the input light 14 reflected from the anterior surface of the lens, while the fourth Purkinje image is formed by light reflected from the posterior surface of the lens at its interface with the vitreous humor. See, e.g., P. N. Cornsweet and H. D. Crane, *J. Opt. Soc. Am.*, 63, 921 (1973) for a more detailed discussion of Purkinje image formation, which is incorporated by reference.

Alternatively, the axis is defined by a Purkinje from an optional surface 34 placed over the eye 10 such as any of the eye contact surfaces discussed in the priority applications incorporated by reference herein. Likewise, in FIG. 1, a reflection from corneal covering 34 may be termed a "first Purkinje reflex". See for example, the discussion below with respect to the embodiment shown in FIGS. 5A-5B, in which the term "first Purkinje reflex" is used to describe a reflection from an anterior surface of a device element (contact member 520) which in operation is disposed over the corneal surface (this may be a transparent member or may include a mirror surface to enhance reflection) and acts in certain respects as a surrogate for the anterior corneal surface 16.

In the embodiments described in particular detail, the geometric reference axis is identified and determined by the co-alignment of the center of the limbus 26 and a first Purkinje reflex. That is, the reference axis 18 in FIG. 1 is coincident with the center of the limbus 26 and the plane 28 normal to the cornea 12 where plane 28 meets the anterior portion 16 of the cornea at point 32, which is substantially in the center of the cornea of the eye. This reference axis is, or accurately approximates and represents, the geometric axis of the eye, and therefore, the term "geometric axis" may be used interchangeably with "reference axis" in this example.

FIG. 1 shows a block diagram of a system 100 for carrying out a method having aspects of the invention. In the illustrated embodiment, system 100 includes a camera 102 positioned to image eye 10 along the geometric axis 18. Camera 102 provides video image data of eye 10 on a display 104. Coupled to display 104 is an image generator 106, such as a personal computer programmed with commercially-available computer aided design software, capable of generating and overlaying geometric images onto the image of eye 10 appearing on display 104. In operation, image generator 106 overlays an image on the image of eye 10 on display 104. The overlaid image is typically a geometric shape sized and positioned to coincide with an anatomical landmark appearing in the image of eye 10. The selected anatomical landmark should be one that remains unchanged in size, shape and position relative to the eye 10.

A preferred anatomical landmark is limbus 26, which is generally circular. Accordingly, as a first step, image generator 106 can be operated to position an image of a circle on the image of limbus 26. Image generator 106 comprises a processor and can locate the center 30 of limbus 26 using the processor within the system. Next, the first Purkinje reflex 32 is identified. Light from light source 108 travels along path 35, entering the eye 10 through the cornea 12 and is directed by the lens to the retina. A portion of the light is reflected at point 32 off the anterior surface of the cornea 16 (or optionally, the anterior surface of the covering 34), identifying the first Purkinje reflex. Alignment of the limbus center 30 with the first Purkinje reflex 32 defines and allows accurate location of the geometric axis 18. The generation of these image coordinates is well understood in the fields of computer graphics and computer aided design. Thus, one embodiment of the invention includes an image capture system 102 for generating an alignment along the geometric axis 18 from information captured at two distinct but interrelated locations in a subject's eye 10. In a preferred embodiment, the alignment is generated from a combined image of the limbic center 30 and the corneal reflex at location 32. Alternatively, in another embodiment, covering surface 34 provides a reflective surface for a Purkinje image 38.

The limbic center 30 and the anterior corneal Purkinje reflex 32 are ocular features that are both independent and strongly coupled. They are independent in that they are extracted from different biological structures; they are strongly coupled because there is generally a close geometric relationship between the limbic center 30 and the anterior corneal reflex 32 which is derived from the apex of the curvature of the cornea. Specifically, the position and orientation of the eye can be determined simultaneously when these two ocular features are co-aligned. The strong coupling between the limbic center and the anterior corneal reflex ocular features not only facilitates the simultaneous capture of both, but allows these features to be cross-referenced or combined in a common feature space that preserves the geometric relationship between the two.

As noted above, an image capture system 102 generates images 106 of these features by capturing an image of the anterior corneal reflex, capturing an image of the limbic boundary, processing these images, and correlating the spatial distribution of the limbic center and the anterior corneal reflex to provide a combined limbic center/Purkinje reflex image, or covering lens center/Purkinje reflex center. The image capture system 102 includes, or is attached to, one or more light sources 108 such as LED(s) that direct light to the surface of eye 10. The camera system 102 preferably includes optics which include at least one partially reflective mirror that directs light to the eye 10 and that passes light reflected from the eye 10 to an image capture device 102. The optics also include, in one embodiment, a lens system with one or more lenses such that light from the light source 108 is directed to reflect from the anterior corneal surface 32 wherein the light reflected from the anterior corneal surface 32 represents a first Purkinje reflex. The lens system also directs light from the light source 108 to reflect the light from the iris 24, the light reflected from the outer iris representing the limbic boundary.

In one embodiment, the light reflected by the anterior cornea at point 32 and the light reflected by the iris 24 are simultaneously captured by an image capture device 102, such as a digital image capture device, and displayed on display 104 so as to capture and generate a combined image of a limbic boundary and a first Purkinje reflex that can be used to determine ocular alignment. In one embodiment, the image capture device 102 is formed of two cameras that respectively capture an image of a first Purkinje reflex 32 and an image of an iris 24 and sclera 17 which determines the limbic boundary at the same time or near in time. In this embodiment, a limbic boundary representing at least a portion of the captured iris and a first Purkinje reflex representing at least a portion of the anterior corneal reflex are generated wherein the limbic center and the first Purkinje reflex are correlated. These correlated images can be combined together to form one image or they can be linked so that they can be analyzed as either one image or as two separate images. In the various embodiments of the present invention, the combined limbic center and first Purkinje reflex information provides a unique axis geometric axis 18 that can be used to determine eye alignment, treatment and/or diagnostic references.

Objective eye alignment can be determined by positioning the subject's eye 10 relative to the image capture device 102 to allow imaging of the subject's eye. The image capture device obtains data on the patient's eye while the subject's face is placed approximately upright on and secured by an articulated head restraint such that the subject's eyes face substantially forward, in the direction of the image capture device 102. In certain embodiments, the image capture device is adjustable, e.g., using a joystick. The joystick can be tilted horizontally, vertically, or both horizontally and vertically, on a fixed base, in order to adjust the location and/or image displayed on the display 104 by the imaging module 400.

A light beam 35 is applied to the subject's eye 10. The image capture device 102 detects a portion of the beam 35 returned after striking the subject's eye 10 and generates, based on the detected portion of the beam, a limbus image of a limbus portion of the subject's eye and/or a first Purkinje reflex of the subjects eye, which can be displayed on display 104. By observing positions of the limbus image and the first Purkinje reflex, objective and reproducible eye alignment can be determined. A concentric co-alignment of the first Purkinje reflex of the subject's eye and the center of the limbus of the subject's eye establishes the alignment of an ocular geometric axis 18 with the system 100.

In some embodiments of the invention, the system 100 further includes a controller to control the time at which the image capturing device 102 respectively captures images of the cornea and limbus and couples digital representations thereof to the controller for analysis. The controller preferably includes a microprocessor and associated memory. The microprocessor may analyze the captured cornea and limbus images to generate a respective first Purkinje reflex and a limbus center which are combined or linked together as described below. Alternatively, the microprocessor may store the captured and correlated images for transmission via a communication interface to a remote computer for analysis and to generate the respective limbus center, first Purkinje reflex and combined or linked ocular information. In this embodiment, before transmitting data representing the captured images, the microprocessor determines whether the captured images are sufficient to provide alignment data, i.e. data used to align the eye. If the corneal reflex image is determined to be sufficient, the microprocessor controls the image capture device 102 to capture an image of the iris nearly simultaneously with the captured corneal image that was determined to be sufficient for providing eye alignment data. As used herein the term simultaneously refers to being at the same time or near in time, e.g., within approximately 0.5 seconds, such that the captured retina and iris images are correlated.

Signal Generation Upon Optical Alignment

In one embodiment of the invention, the microprocessor controls one or more of the cameras in the image capture device 102 to capture a corneal image capturing and/or an iris image, and generate an alignment signal indicating that an eye is properly aligned with the system. Proper alignment is when an axis intersects the eye at least two predetermined features on the eye, e.g., the limbus center and the first Purkinje reflex. The alignment signal may be generated by a switch or the like that is manually actuated by a physician when the subject's eye is determined to be in alignment as displayed on display 104. Alternatively, the system can automatically detect when the eye is in sufficient alignment with the system.

Figure 2:
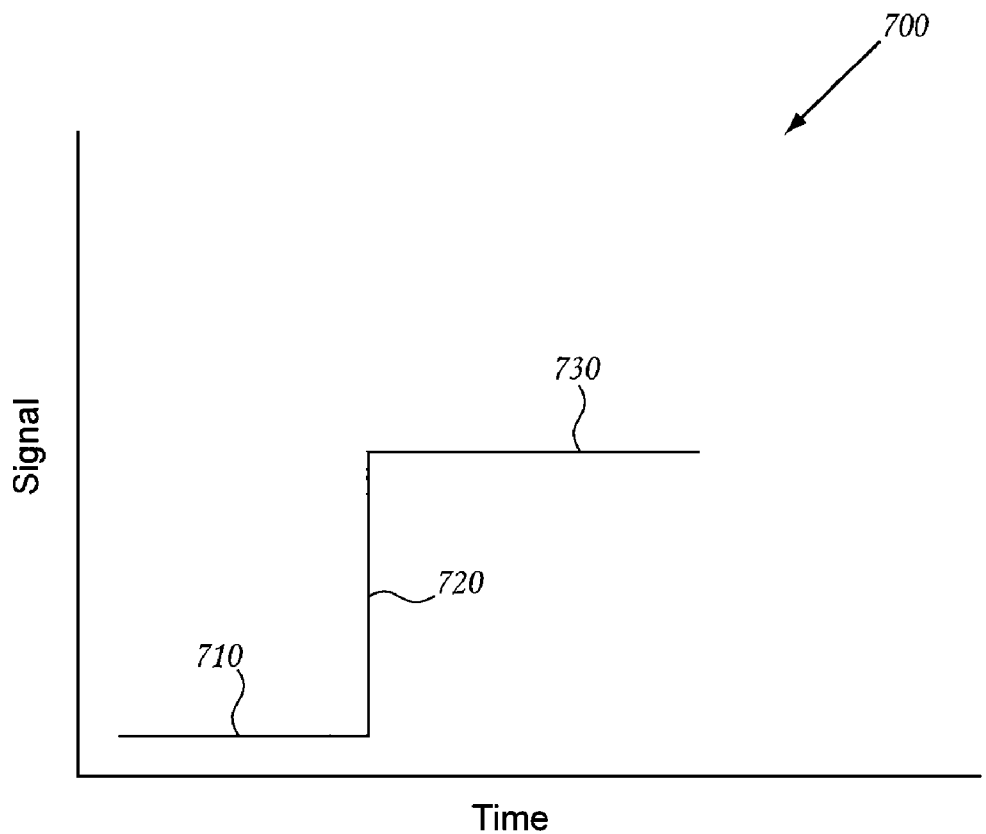
FIG. 2 is an exemplary plot of a co-alignment detection signal indicative of coincident reflection of the first Purkinje reflex and the center of the limbus.

A signal is generated only when the beam path 35 of the light beam reflected from a measurement surface 32 is co-aligned with the center of the limbus 30 or center of covering surface 34. In order to achieve co-alignment, the image capture device 102, in cooperation with image generator 106, recognizes the reflection of the probe beam 35 from the anterior corneal surface corresponding to the first Purkinje reflex, and the center of the limbus. As shown in the graph 700 in FIG. 2, the co-alignment signal 710 is essentially zero until the coincident reflection of the first Purkinje reflex and the center of the limbus are detected 720. At point 730, the geometric axis is aligned with the system, and according to the invention, this signal can be used to trigger a subsequent desired event. Or indeed, at alignment, the signal is defined and then if there is a non-signal, this itself is a signal that the device is out of alignment.

In one embodiment, an alignment signal activates an eyetracker apparatus for monitoring the movement of the eye during a diagnostic or therapeutic procedure or other desired function. In a conventional eyetracker system, the patient may be asked to fixate on an illumination source while a visible laser beam coincident with a therapeutic beam axis is directed onto the patient's cornea. Based upon the surgeon's observation of the visible laser beam in relation to the corneal position, the surgeon will manually engage the eyetracker using his or her best judgment about the corneal position. Advantageously, according to the invention, the eyetracker can now be triggered automatically and more accurately since the alignment signal will only be generated when the patient's geometric axis is properly aligned.

In certain embodiments, the eye-tracking system is configured to track patient movement, such as eye movement, for use by the system. The eye-tracking system can calculate a three-dimensional image of the patient's eye via physician inputs, and can include real-time tracking of movement of the patient's eye. The eye-tracking system obtains data that becomes a factor for determining treatment planning for a number of medical conditions relating to the eye. For example, the eye-tracking system may create an image of the posterior region of the patient's eye using the data it obtains. In certain embodiments, the data can be transferred via cable communication or other means, such as wireless means, to a treatment or diagnostic device. In certain embodiments, a processing module coupled to the treatment or diagnostic device may process data on the patient's eye and present an image of the patient's eye on a coupled display. In certain embodiments, the coupled display may present a real-time image of the patient's eye, including movement of the eye.

In another embodiment, the alignment signal is utilized to reversibly engage an ocular positioning and/or stabilizing device to the subject's eye, the ocular positioning and stabilizing device being in cooperative engagement with the system. An exemplary positioning and/or stabilizing device is described in detail below, and illustrated in FIGS. 4A-5B.

Range Finder

In another embodiment of the invention, the system includes a proximity detector (103 in FIG. 1) in the form of a range finder (camera) or transducer such as an ultrasound transducer to determine when an eye is at a predetermined distance from the system. The proximity detector is preferably positioned adjacent the image capture device 102. The proximity detector is operated in a transmit and a receive mode. The distance between a system reference point (e.g., a selected point co-linear with path 35) and the subject's eye (e.g., the corneal surface 16) can be determined by the microprocessor or a dedicated integrated circuit coupled to the proximity detector. The microprocessor or integrated circuit calculates the distance between the eye and the system to determine the proximity of the eye to the system.

In one embodiment, the microprocessor or integrated circuit compares the determined distance between the eye and the system to a predetermined distance value stored in the memory, a register or the like, accessible by the microprocessor or integrated circuit. When the microprocessor determines from the output of the proximity detector that the individual is at a predetermined or correct distance, the microprocessor signals the image capture device 102 to capture an image of an area of the limbus 26. Simultaneously, the microprocessor may signal the image capture device 102 to capture an image of the cornea 12. In one embodiment, the microprocessor first controls the image capture device 102 to capture an image of the cornea which is immediately analyzed by the microprocessor to determine whether the first Purkinje reflex captured is sufficient to provide alignment information as discussed above. When a sufficient first Purkinje image is detected, the microprocessor signals the image capture device 102 to capture an image of the limbus 26. In this embodiment, the microprocessor analyzes the captured image of the cornea for sufficiency in sufficient time that the microprocessor can signal the image capture device to capture an image of the limbus near enough in time to the captured image of the cornea so that the images are correlated and can be considered simultaneously captured.

Note, that in addition to use in operation of the alignment system as described above, the proximity detector can be configured to monitor eye distance over any selected time period, for example after the alignment of the eye reference axis (e.g., axis 18) by the alignment system, during treatment or diagnostic operation (e.g., input for controls feedback, safety interlocks and the like).

Coupling the Alignment System to a Treatment System

In some embodiments of the invention, the system alignment is directly, or indirectly, coupled to a treatment or diagnostic device. The alignment method is used in combination with a treatment device to treat a wide variety of medical conditions relating to the eye. As discussed in further detail below, once the reference axis is defined, it can be geometrically linked to anatomic structures of the eye which may be of interest in treating structures or diseases, e.g., tissue sites on the retina such as the macula affected by macular degeneration. Likewise, the reference axis may be linked to other regions of treatment of the eye, such as regions of the retina such as the fovea, the macula, a pathologic lesion such as a tumor, a growth of blood vessels, a membrane, a telectasia, and an edematous region, and the like.

For example, the system may be used alone or in combination with other treatments to treat macular degeneration, diabetic retinopathy, inflammatory retinopathies, infectious retinopathies, tumors in, around, or near the eye, glaucoma, refractive disorders, cataracts, post-surgical inflammation of any of the structures of the eye (e.g., trabeculoplasty, trabeculectomy, intraocular lenses, glaucoma drainage tubes, corneal transplants, infections, idiopathic inflammatory disorders, etc.), ptyrigium, dry eye, and other ocular diseases or other medical conditions relating to the eye. The treatment system is preferably a radiotherapy system that also includes controls for defining the maximum beam energy (e.g., ranging between about 30 keV to about 150 keV), beam angles, eye geometries, and controls to turn off the device when the patient and/or eye move out of position.

The radiotherapy treatment system includes, in some embodiments, a radiation source, a system to control and move the source to a coordinate in three-dimensional space, an imaging system, and an interface for a health care professional to input treatment parameters. Specifically, some embodiments of the radiotherapy system include a radiotherapy generation module or subsystem that includes the radiation source and the power supplies to operate the source, an electromotive control module or subsystem that operates to control power to the source as well as the directionality of the source, a coupling module that links the source and control to the eye, and an imaging subsystem. In some embodiments, these modules are linked to an interface for a health-care professional and form the underpinnings of the treatment planning system. In another embodiment described below, the treatment system is a photoablative laser surgery system.

Figure 3A:
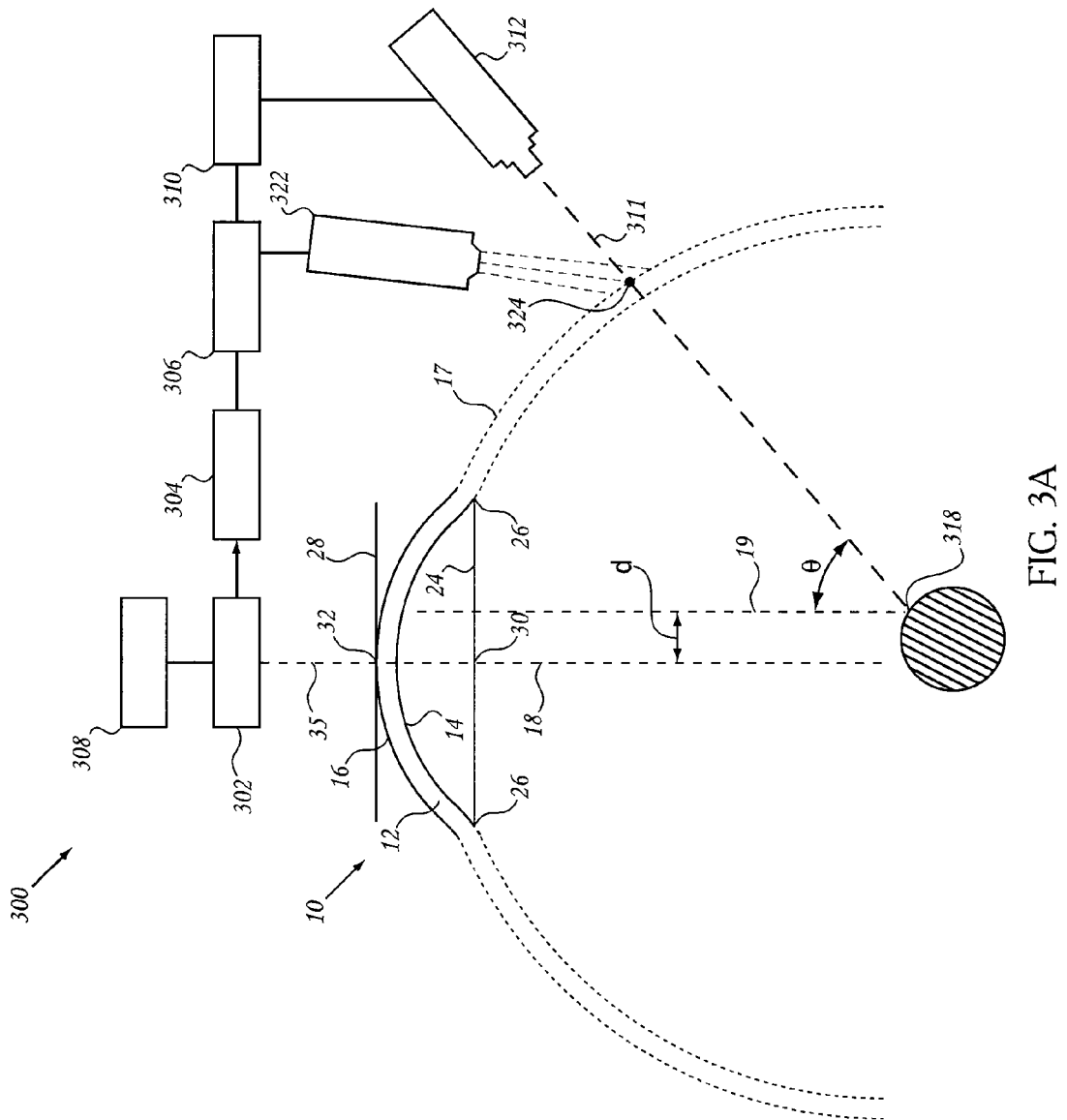
FIGS. 3A and 3B illustrate exemplary ophthalmic treatment systems having aspects of the invention, including a treatment device which is positioned and/or controlled by an eye positioning/stabilizing device.
Figure 3B:
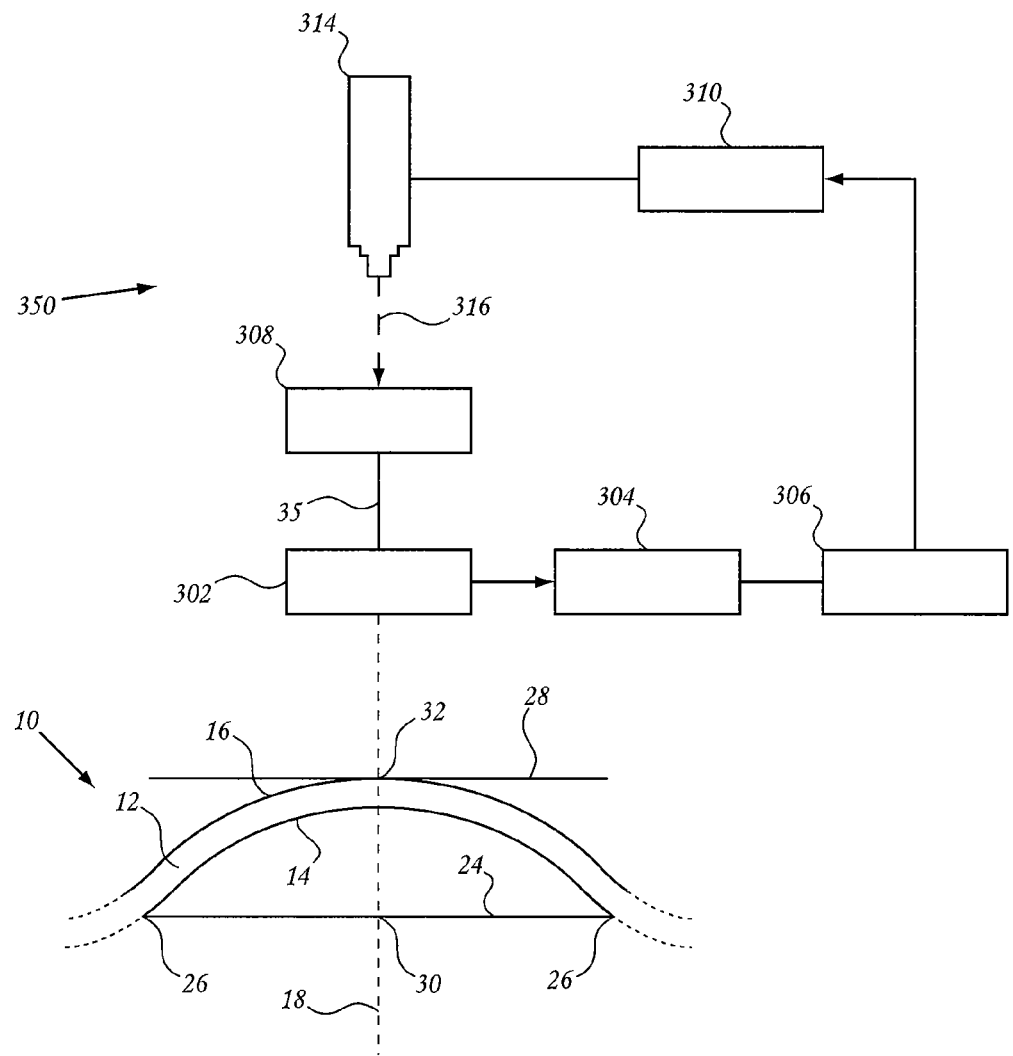

FIGS. 3A and 3B illustrate two examples of embodiments having aspects of the invention, in which the alignment system is coupled to a treatment system (e.g., a radiotherapy device, an ablation laser, or the like) and configured to provide operative control and/or monitoring of the treatment system functionality, such as position control, orientation control, timing control, power enablement-disablement, and the like. In the examples shown, the alignment system is coupled to a treatment system, where image generator 306 is coupled to a positioning device 310 used to position an ophthalmic treatment device (312 and 314 in FIGS. 3A and 3B, respectively), e.g., an ablation laser or radiotherapy device.

In FIG. 3A, the position of the geometric axis 18, properly located by the alignment system, can be used by positioning device 310 to direct ophthalmic treatment device 312 at a tissue target 318, which may or may not be positioned along axis 18. In this example, target 318 is positioned off-axis with respect to geometric axis 18, as further discussed below.

In FIG. 3B, the position of the geometric axis 18, properly located by the alignment system, can be used by positioning device 310 to "center" ophthalmic treatment device 314 on the eye's geometric axis 18, for example, where as a treatment target is centered on the geometric axis, as further discussed below.

In these embodiments of the invention, the position of the eye and the treatment device are known at all times, and the angles of entry of the therapeutic or diagnostic beam can therefore be realized. For example, the geometric axis of the eye can be determined and defined as the reference axis of the system. A treatment axis may be defined with respect to the reference axis, and then the treatment device may be positioned at a known angle and/or offset distance from the reference axis. For treatment targets lying on the reference axis, the treatment axis may be defined as the reference axis. Depending on the region to be treated, the treatment device can be readjusted; for example, a robot arm can move the treatment device to a position to send a therapeutic beam to a location on or in the eye.

Returning to the embodiment illustrated in FIG. 3A a schematic view is shown of an alignment and treatment embodiment, including a cross-sectional view of a portion of the eye taken along the geometric axis. System 300 includes an image capture device 302 positioned to image eye 10 along the geometric axis 18. Image capture device 302 provides video image data of eye 10 to a display 304. Coupled to display 304 is an image generator 306, such as a personal computer programmed with commercially-available computer aided design software, capable of generating and overlaying geometric images onto the image of eye 10 appearing on display 304. In operation, image generator 106 overlays an image on the image of eye 10 on display 304. The overlaid image is typically a geometric shape sized and positioned to coincide with an anatomical landmark appearing in the image of eye 10. The selected anatomical landmark should be one that remains unchanged in size, shape and position relative to the eye 10.

A preferred anatomical landmark is limbus 26, which is circular. Accordingly, as a first step, image generator 306 can be operated to position an image of a circle on the image of limbus 26. Image generator 306 can then locate the center 30 of limbus 26. Next, the first Purkinje reflex 32 is identified. Light from light source 308 travels along path 35, entering the eye 10 through the cornea 12 and is directed by the lens to the retina. A portion of the light is reflected at point 32 off the anterior surface of the cornea 16, identifying the first Purkinje reflex. Alignment of the limbus center 30 with the first Purkinje reflex 32 defines and allows accurate location of the geometric axis 18 as a reference axis with respect to the external coordinate system.

With the position of the geometric axis 18 properly located, the geometric axis 18 becomes an axis of reference, and can thereby be used by positioning device 310 to direct ophthalmic treatment device 312 toward the eye at a predetermined orientation with respect to from geometric axis 18 such that a therapeutic beam, such as a beam of collimated electromagnetic radiation 311, can be aimed at a predetermined coordinate of the eye 10 so as to enter the body surface (point 324 on the surface sclera 17) and propagate to impinge on a selected target tissue 318.

Note that FIG. 3A is a planar illustration of 3-dimensional eye anatomy, and in general beam axis 311 of device 312 need not intersect the geometric reference axis 18 (i.e., axes 18 and 311 may, but need not, lie within a plane). In general, the beam axis 311 may have a selected orientation with respect to geometric reference axis 18, such as a selected angle "θ" and offset "d" with respect to axis 18. The device 312 can in fact be angled to intersect any anterior-posterior line within the eye.

Once reference axis 18 is identified, treatment may be carried out by a device oriented with respect axis 18, for example where a treatment target lies along axis 18 (see description regarding FIG. 3B). Alternatively, a distinct axis 19 may be defined with respect to axis 18, for example by a shift of distance "d", so that axis 19 intersects treatment target 318 positioned off-axis with respect to axis 18. Axis 19 may be called the "treatment" axis. Based on straightforward geometry, the device 312 can now be positioned so that its beam axis 311 intersects treatment axis 19 at tissue target 318. Axis 18 may be used to define one or more correlated geometric axes in the external coordinate system, and to define one or more additional intersection points with respect to beam 311. Note for treatment targets lying on reference axis 18, offset "d" may be about zero, and for treatment delivered through or to the cornea, angle "θ" may approach zero.

Figure 3C:
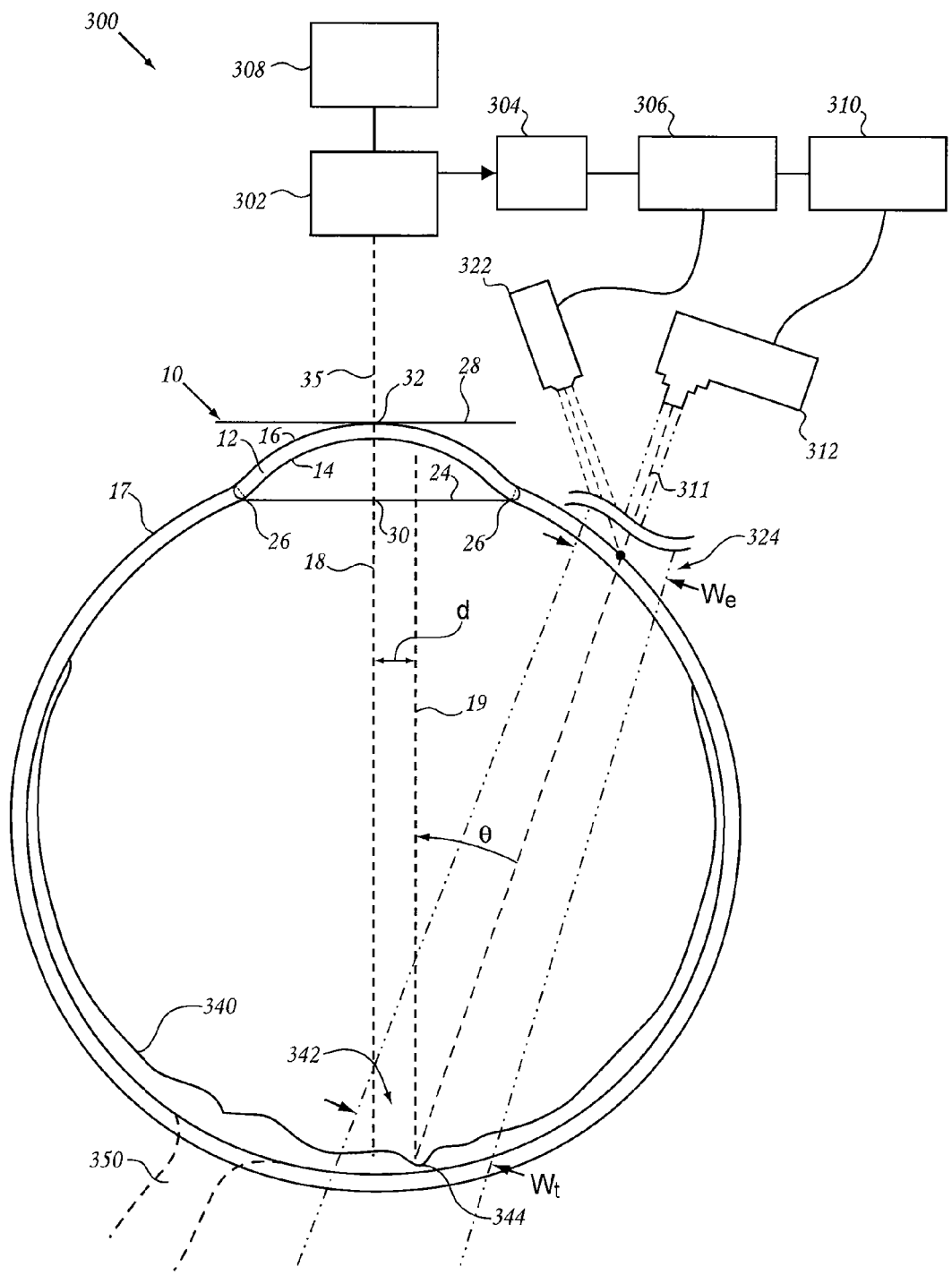
FIGS. 3C and 3D illustrate exemplary ophthalmic treatment system for X-ray treatment of the retina, wherein FIG. 3C a cross-sectional view of an eye taken along the geometric axis in a horizontal plane.
Figure 3D:
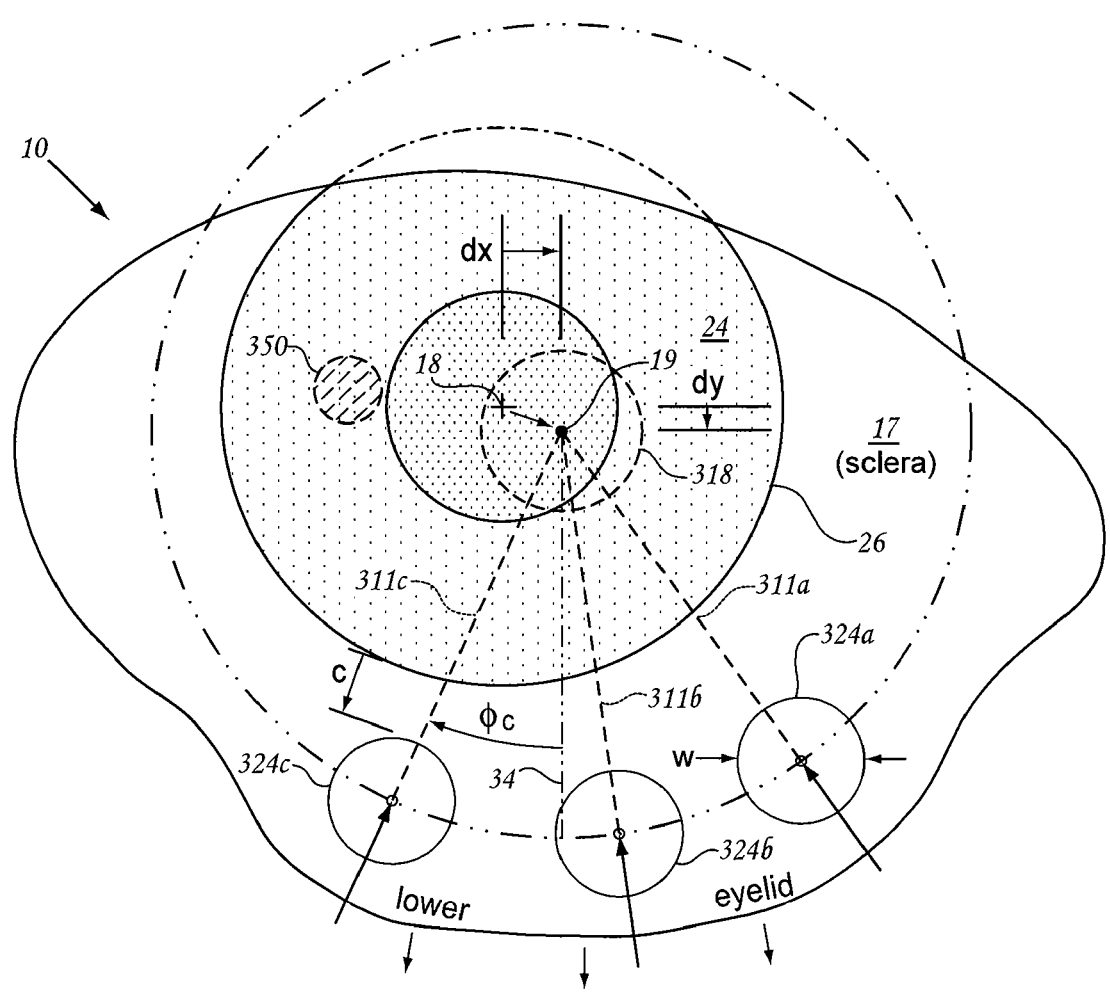

FIGS. 3C-3D illustrate an example of an embodiment in which the alignment system is coupled to a treatment system adapted for orthovoltage X-ray treatment of a region of the retina generally including the macula. FIG. 3C a cross-sectional view of an eye taken along the geometric axis in a horizontal plane, shown in association with alignment-treatment system 300. FIG. 3D is a detail frontal view of an eye as seen aligned with axis 18 (temporal to right, nasal to left).

As shown in FIG. 3D, although a single beam axis 311 may be employed, a plurality of beam axes may be defined in which two or more treatment beams are aimed to impinge on target 318 stereotactically. Treatment axis 19 may be chosen to intersect a selected target 318 within the eye, and employed as a reference to orient two or more treatment beams aimed to impinge on target 318 stereotactically. In the example of FIG. 3D, treatment axis 19 is chosen to intersect a selected target 318 within the eye, and employed as a reference to orient three treatment beams projected along three different beam axes 311a, 311b and 311c, the beam axes defined so as to each impinges on target 318 from a different direction.

Multiple beams may be projected simultaneously, or sequentially, with intervening periods of no treatment if desired. Likewise, multiple beams may be provided by multiple separately-positioned treatment devices. However, a preferred embodiment employs a single treatment device 312 (e.g. a collimated orthovoltage X-ray source), which is sequentially repositioned by positioning device 310 to administer treatment in sequential doses along each of a plurality of beam axes, such as axes 311a, 311b and 311c.

The beam axes each have a different respective point of entry into the body surface (324a, 324b and 324c respectively) and each follows a different tissue path leading to target 318. Likewise each beam follows a different tissue path for any propagation beyond target 318. In this way, treatment beam dosage penetrating tissue remote from target 318 may be minimized relative to the dosage received at target 318.

Beam axis 311 (or for multiple beams, each of axes 311*a-c*) may be selected to follow a tissue path which avoid vulnerable structures or tissues which are remote from target 318, so as to minimize dosage received by such tissues. For example, in treatment of the macula for macular degeneration, axes 311*a-c* may be selected to deliver a selected dose of beam treatment (e.g., a selected dosage of absorbed X-ray energy) to a target 318 on or near the retina 340, centered on the macula 342 while minimizing absorbed radiation by the optic nerve 350, the lens, and the like.

In the example shown, three beam axis 311*a*, 311*b* and 311*c* are defined, so that the beams directed towards the posterior eye enter the body on the surface of the anterior sclera 17 at points 324*a*, 324*b* and 324*c*, each entry point a selected distance beyond the limbus 26. Such beam orientation can avoid or minimize absorption by the lens and other structures within the eye, by appropriate selection of the beam paths.

Positioning device 310 may provide for robotic control with any selected degrees of freedom and may have corresponding feedback sensors to permit accurate treatment control by a processor and/or manual operator. See for example, high degree-of-freedom robotic surgical control systems such as employed in the CyberKnife® robotic radiosurgery system (Accuray, Inc. Sunnyvale, Calif.) and the da Vinci® minimally-invasive surgical system (Intuitive Surgical, Inc., Sunnyvale, Calif.). Such systems can provide for a high degree of operational range and flexibility. Note that in the most general case, treatment axis 19 need not be parallel to reference axis 18, and target 318 may be located relative to axis 18 by other analytical methods not including a separately-defined treatment axis. On the other hand, a real or at least conceptual hazard of high degree-of-freedom robotic systems employing energy beam treatment, is the large possible range of beam paths (e.g., upon a control system failure), and associated risk issues, regulatory complexity, and high end-user installation and site modification costs.

Important safety and regulatory/validation advantages, and well as compactness and cost reduction, may be provided by configuring positioning device 310 to have a reduced degrees of freedom and simplified control devices and/or software. Particularly where a treatment system is optimized for a particular range of treatment procedures (e.g., treatment targets in or near the retina), a finite number of rotational or translational degrees of freedom (e.g., track or pivot mounted electrical actuators) can provide the desired range of selectable beam paths to administer a medically optimal dosage to the treatment target.

As illustrated in FIG. 3D, one or more of beam axes (311*a*, 311*b* and 311*c*) are defined such that each axis lies within a conical conceptual surface and whereby each beam intersects the apex of the cone. The cone may be defined having as its conical axis the treatment axis 19 with the apex disposed at target 318. In this example, treatment axis 19 is defined parallel to reference axis 18, having x-y offsets define in an perpendicular plane by "dx" and "dy" respectively (for a treatment target intersected by the reference axis the offsets are zero). Once the treatment axis 19 is defined, the base 34, the apex angle ("θ" in FIG. 3C), and rotational positions of axes 311*a-c* with respect to axis 19, may be adjusted to provide both beam intersection at about target 318 as well as to provide entry points 324*a-c* located at a desired position of the body surface.

As shown in FIG. 3C, in one example of an orthovoltage X-ray treatment for macular degeneration, off-sets dx and dy are selected to define a treatment axis 19 centered on the macula, angle θ is selected to provide intersection of beams 311*a-c* on the macular surface, and base 34 is selected to provide surface entry points 324*a-c* in a region of the lower anterior sclera beyond the boundary of limbus 26. In this example, an X-ray beam source may positioned by positioning device 310 so as to project a collimated beam from a selected X-ray source distance so as to form a beam having a characteristic width at tissue entry "w". Note that although a treatment beam may be projected through an eye-lid or other tissue proximal to the eye, the eyelids (in this case the lower eyelid) may be conveniently retracted so as to expose an additional area of the anterior sclera 17.

In the example shown in FIGS. 3C-3D, target 318 is approximately the fovea 344. As shown in FIG. 3C, collimated orthovoltage X-ray beam 311 at entry to the sclera has a effective beam with of $W_e$ (e.g., as defined by a boundary at the 90% isodose). The beam 311 spreads at it propagates through the eye, to have an effective beam width of $W_t$, which covers an area surrounding the target constituting the treatment region, in this case corresponding to the macula.

In the example shown, for each beam axis 311*a-c*, a rotational angle φ may be selected to define a distinct propagation path for the beam (e.g., a path which avoids vulnerable structures such as the optic nerve 350 and which is sufficiently distinct from other treatment beams to reduce collateral tissue dosage). Note that where the treatment axis 19 is offset from geometric reference axis 18, the points 324*a-c* will tend to be different distances from limbus 26, and the combination off base 34 and rotational angle φ for the closest beam may be selected to assure a desired minimum corneal clearance "c" for beam entry (324*a* in FIG. 3B).

The positioning device 310 may conveniently have actuators providing for 5 degrees of freedom of motion for treatment device 312, such as providing x-y-z adjustment relative to the patient's eye, and rotation for the angles θ and φ to direct each of beams 311*a-c* to target 318 along a distinct path. See, for example the constrained positioning system for an X-ray source and collimator, as described and shown with respect to FIGS. 12E-F of co-invented/owned U.S. patent application Ser. No. 12/100,398, entitled "Orthovoltage Radiosurgery" filed Apr. 9, 2008 by Gertner et al., which is incorporated by reference.

Without departing from the spirit of the invention, one of ordinary skill in the art will appreciate that for a specialized device optimized for a particular range of treatments, fewer degrees of freedom may be provided, as, for example, when certain of the parameters described may reasonably be fixed. Note in this regard that an eye positioning and/or stabilizing device, such as shown if FIGS. 4-5, may include actuators (or employ manual patient movement) sufficient to change the position and orientation of the treated eye 10, so as to substitute for degrees of freedom of the positioning device 310 with respect to the treatment device 312. Thus, the patient and/or eye may be moved in one or more parameter with respect to device 312, until it is determined that the treatment path 311 is correctly aimed at target 318 (which may be confirmed by the alignment system).

In some embodiments, one or more additional imaging camera systems may be included. In the example shown in FIG. 3A, camera 322 is configured to be positioned by positioning device 310, and aimed so as to obtain an image of the area of intersection of therapeutic beam 311 with an exposed body surface, such as an exposed area of the scleral surface of the eye. Additionally, a reference light beam may be provided to illuminate and/or mark the of intersection area. For example, device 312 may incorporate a laser pointer beacon along a path coincident with therapeutic beam 311 (e.g., directed by a co-aligned mirror), so as to indicate the intersection of beam 311 on a surface of the eye (e.g., for visual or automated confirmation of the alignment of beam 311, or the like). Alternatively, a reference light beam may be provided which is not aimed along a path coincident with therapeutic beam 311, for example, configured to be aimed by positioning device 310 on a path intersecting the surface at area (see FIG. 2C and related description of co-owned U.S. application Ser. No. 11/873,386 filed Oct. 16, 2007, which is incorporated by reference).

In the embodiment depicted in FIG. 3B, system 350 includes a camera 302 positioned to image eye 10 along the geometric or reference axis 18. Camera 302 provides video image data of eye 10 to a display 304. Coupled to display 304 is an image generator 306, such as a personal computer programmed with commercially-available computer aided design software, capable of generating and overlaying geometric images onto the image of eye 10 appearing on display 304. In operation, image generator 306 overlays an image on the image of eye 10 on display 304. The overlaid image is typically a geometric shape sized and positioned to coincide with an anatomical landmark appearing in the image of eye 10. The selected anatomical landmark should be one that remains unchanged in size, shape and position relative to the eye 10.

A preferred anatomical landmark is limbus 26, which is circular. Accordingly, as a first step, image generator 306 can be operated to position an image of a circle on the image of limbus 26. Image generator 306 can then locate the center 30 of limbus 26. Next, the first Purkinje reflex 32 is identified. Light from light source 308 travels along path 35, entering the eye 10 through the cornea 12 and is directed by the lens to the retina. A portion of the light is reflected at point 32 off the anterior surface of the cornea 16, identifying the first Purkinje reflex. Alignment of the limbus center 30 with the first Purkinje reflex 32 defines and allows accurate location of the geometric axis 18. With the position of the geometric axis 18 properly located, the geometric axis 18 becomes an axis of reference, and can thereby be used by positioning device 310 to direct ophthalmic treatment device 314 toward the eye and co-aligned with the geometric axis 18 such that a therapeutic beam, such as a beam of an ablation laser 316, can be aimed at a predetermined coordinate of the eye 10, such as point 32 on the cornea 12 of eye 10.

The treatment device 314, in one embodiment of the invention, is a utilized for treating macular degeneration of the eye using radiotherapy. For example, in some embodiments, systems and methods are described for use of radiotherapy on select portions of the retina to impede or reduce neovascularization of the retina. Some embodiments described herein also relate to systems and methods for treating glaucoma or controlling wound healing using radiotherapy. For example, embodiments of systems and methods are described for use of radiotherapy on tissue in the anterior chamber following glaucoma surgery, such as trabeculoplasty, trabeculotomy, canaloplasty, and laser iridotomy, to reduce the likelihood of post-operative complications. In other embodiments, systems and methods are described to use radiotherapy to treat drusen, inflammatory deposits in the retina that are thought to lead to vision loss in macular degeneration. Localized treatment of drusen and the surrounding inflammation may prevent the progression of dry and/or wet AMD.

In some embodiments, laser therapy is applied to drusen in combination (adjuvant therapy) with co-localized x-ray radiation to substantially the same location where the laser is incident upon the retina; the laser can create a localized heating effect which can facilitate radiation treatment, or the laser can ablate a region, or laser spot, while the radiation can prevent further scarring around the region. Such combination therapy can enhance the efficacy of each therapy individually. Similarly, adjuvant therapies can include x-ray radiotherapy in combination with one or more pharmaceuticals or other radiotherapy-enhancing drugs or chemical entities. In some embodiments, x-ray therapy is combined with invasive surgery such as a vitrectomy, cataract removal, trabeculoplasty, trabeculectomy, laser photocoagulation, and other surgeries.

Reversibly Coupling an Ocular Device to the Eye Following Alignment

Figure 4A:
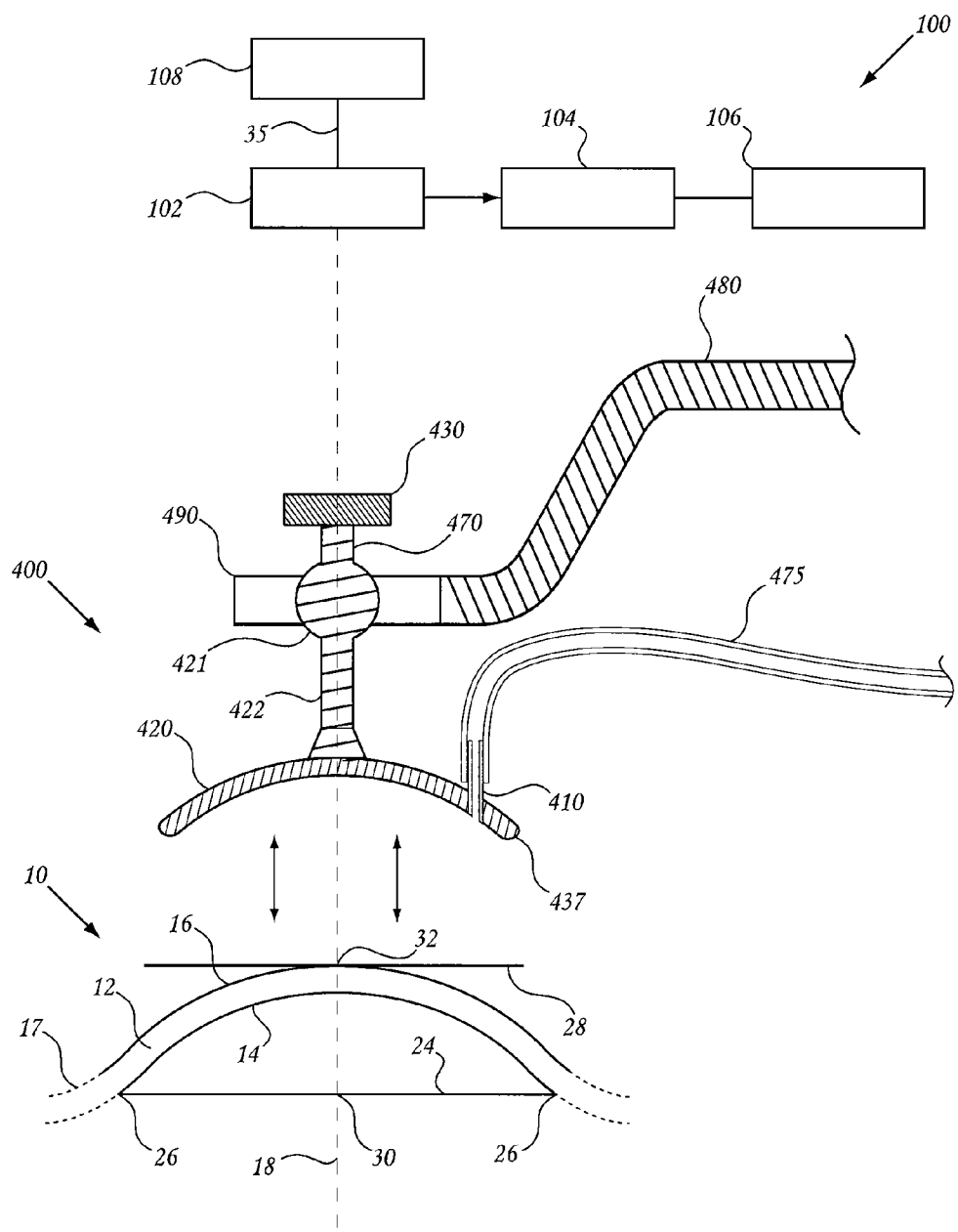
FIGS. 4A-B and 5A-B illustrate exemplary eye positioning and/or stabilizing devices having aspects of the invention.
Figure 4B:
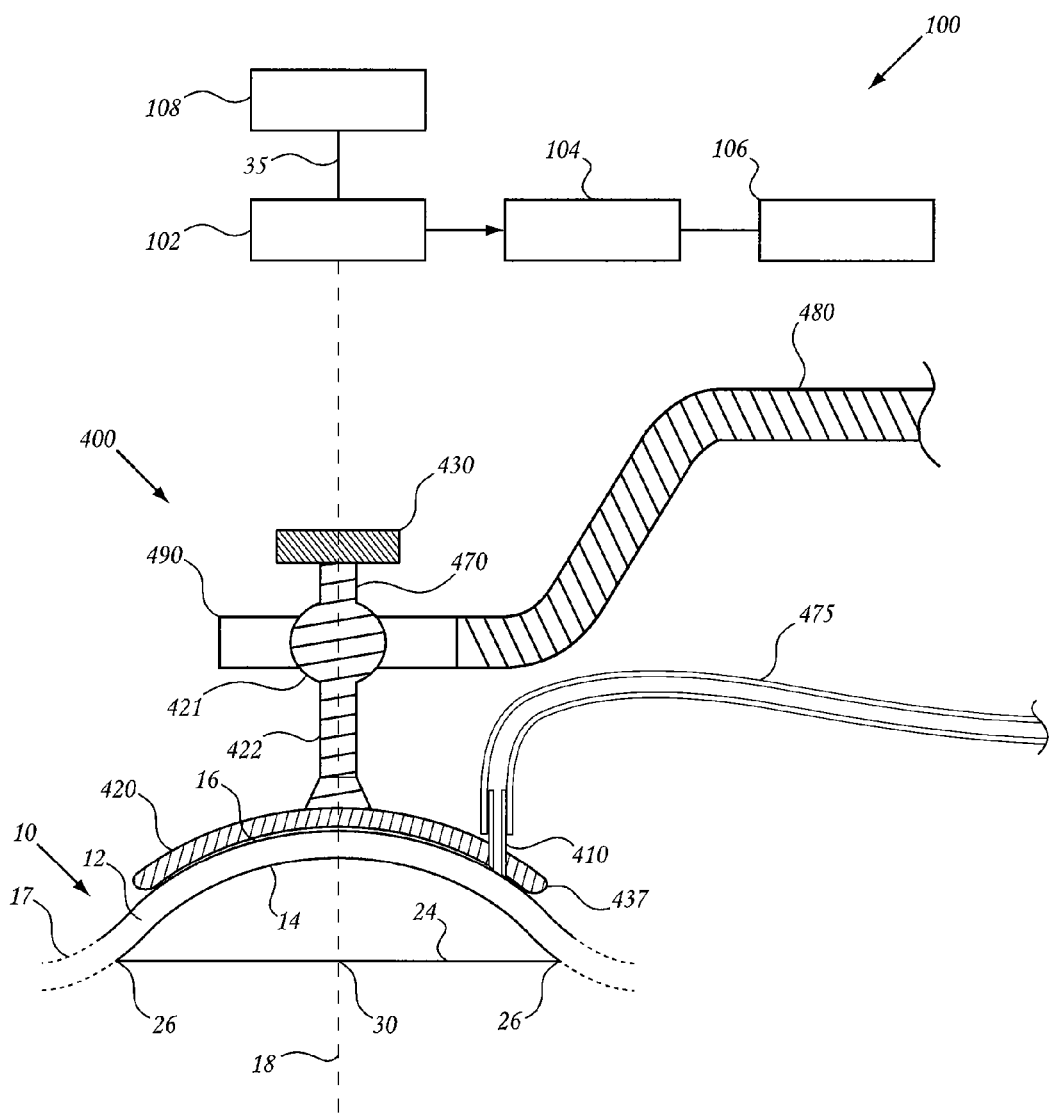

Referring now to FIGS. 4A-4B, following identification of the geometric axis 18, as described in detail above, an ocular device, e.g., the ocular device 400 described in co-owned U.S. provisional application No. 61/020,655, filed Jan. 11, 2008, entitled, "System and Method for Positioning and Stabilizing an Eye," which is incorporated by reference herein, can be positioned onto, and aligned with eye 10. Following positioning and alignment, the ocular device 400 can be utilized for a number of methods, including
  (i) controllably stabilizing the eye,
  (ii) physically manipulating the eye position,
  (iii) limiting eye movement during treatment,
  (iv) providing a positional reference relative to external coordinates of the surface of the eye and its internal anatomy,
  (v) providing fiducials relative to the eye,
  (vi) maintaining corneal lubrication during treatment, and
  (vii) providing a mechanism to align a treatment device and continuously signal indicative of adequate alignment or misalignment.

FIGS. 4A-4B schematically illustrates a top-down view of the ocular device 400 being reversibly and controllably coupled to the cornea 12 and/or limbus 24 of the eye 10, in association with alignment system 100. Note that ocular device 400 (and other ocular device embodiments having aspects of the invention) may be usefully employed independently from alignment systems, such as system 100. The ocular device may be supported by a mounting (not shown) coupled to positioning arm 480 so as to maintain the eye in a first position to provide stability for the eye while the eye is being treated. The mounting may be configured to manually and/or robotically adjust the position of device 400 and eye 10. The ocular device 400 includes a contact member 420 which contacts eye 10. The contact member 420 can be positioned on the eye in a variety of positions, and is therefore useful in a wide variety of ocular treatment procedures. As further illustrated in FIG. 4B, the eye contact member 420 includes a curved structure that is generally centered on the axis 18 and contacts portions of the anterior surface of eye 10. As will be seen below with reference to FIG. 5A, the ocular guide may provide an outer reflecting surface normal to and intersected by the center axis of the eye contact member, allowing eye alignment by using a reflection from this reflecting surface as a Purkinje reflection, that is, as a surrogate for the first Purkinje reflection off the anterior surface of the cornea.

In some embodiments, the contact member 420 contacts all or a portion of the corneal surface 16, and in some embodiments, the contact member 420 contacts portions of the surface of the sclera 17 (represented by dashed lines) disposed adjacent the limbus 26 while cover all or a portion of the corneal surface 16. For example, in one embodiment, the eye contact member 420 has a profile configured so that the periphery 437 of the contact member 420 is in contact with the sclera 17 adjacent the limbus 26, and configured so the center portion of the contact member 420 substantially cover the cornea, but is not in direct physical contact with at least a central portion of the cornea.

In another alternative embodiment, contact member 420 may be sized and configured so that in operation, it covers a majority of the corneal surface, while leaving all or a portion of the limbus 26 visible beyond the edge 437 of contact member 420. In this embodiment, a camera of an alignment system (see, for example, FIGS. 1 and 6) may be arranged to obtain and may process images of the limbus while contact member 420 is in contact with the cornea 12. For example, a camera, such as camera 102 or another camera may be provided, configured to enable an alignment system to confirm the placement and stability of contact member 420 by the spatial relationship of member 420 to limbus 26.

The eye contact member 420 may be held against eye 10 by a selected bias force, e.g., as applied mechanically via positioning arm 480. In addition, or alternatively, vacuum suction may by employed to create attraction between member 420 and the surface of eye 10. The eye holder illustrated in FIGS. 4A-4B includes a vacuum port 410 which functions as an air and/or fluid passage and can be adapted for coupling to a vacuum source through vacuum line 275. In the embodiment illustrated in FIGS. 4A-4B, the vacuum port 410 is positioned through the eye contact member 420 such that an air or fluid communication space is formed through eye contact member 420 to allow air trapped between eye contact member 420 and the anterior surface of the cornea 12 of eye 10 to be removed, thereby reversibly engaging the eye contact member 420 with the anterior surface of the eye in the region of the cornea 12. Vacuum pressure may be adjusted for patient comfort, and in relation to bias force and cup geometry. For example, a vacuum pressure of about 25 mm Hg or less has been shown to be adequate to provide eye stability in one embodiment having aspects of the invention. When the ocular device is seated onto and coupled with eye 10, the mirror 430 is aligned such that it is substantially parallel to plane 28 (normal to the cornea 12 at axis 18 coincident with the center of the limbus 26). In this way, the mirror 430 becomes an additional alignment tool for performing an alignment procedure on a subject's eye 10. Alignment methods having aspects of the invention may include identifying a reflection of beam 35 (light source 108) from mirror 430, and aligning the refection with respect to an anatomical landmark, such as the center of limbus 26. Such methods may be employed in addition to or instead of alignment methods based on a first Purkinje reflex from the surface 16 of cornea 12 as described above with respect to FIG. 1.

Note that all or a portion of contact member 420 may comprise a transparent material, to permit an operator (and/or a system camera) to visualize the relative position of eye structures such as the limbus 26 as contact member 420 is brought into contact with eye 10, and while member 420 remains in contact.

An exemplary method for performing an alignment procedure following the positioning of the ocular device 400 on the subject's eye 10 includes supporting the subject's head at a fixed position in an external coordinate system, determining the position and orientation of the eye according to any of the methods described above, attaching to the front of the eye 10 an ocular contact device 400 effective to stabilize the position of the eye relative to the contact device 400, and thereafter determining the position and orientation of the ocular contact device in the external coordinate system, thereby to determine the position and orientation of the patient's eye in the external coordinate system. The eye 10 can thereafter be moved or positioned as desired, while maintaining stable contact between eye 10 and contact member 420, and while monitoring the motion or position of contact device 400 in the external coordinate system. For example, after attaching the eye 10 to the ocular contact device 400, the method can include moving the ocular contact device 400 to place the device 400 at a selected orientation in the external coordinate system, such as by adjusting the angular position of the contact member 420 with respect to the subject's head. The position of the ocular device in the external coordinate system with such placed in the selected orientation can then be determined.

In a related embodiment, with the ocular device 400 now positioned on the eye, a therapeutic device can be utilized to provide therapeutic treatment to the subject's eye. In this embodiment, a source of a collimated electromagnetic beam, such as an x-ray beam, is positioned such that when it is activated, it is aimed along a selected line of sight at a selected coordinate in the external coordinate system corresponding to a selected target region in the subject's eye.

FIGS. 17A-17D depicts embodiments of eyeholders 400 (*a-d*) having aspects of the invention, similar in many respect to those shown in FIGS. 4A-B and FIG. 16, having alternative configurations of contact member 420. For each figure, the eyeholder 400 is shown superimposed on a schematic frontal view of a portion of an eye 10 having iris 24 adjoining region of sclera 17, the junction of which defines limbus 26. For each figure, the eye 10 is shown aligned with reference axis 18 positioned at the center of limbus 26. In each figure, support post 422 is shown centered on axis 420, although it need not be centered.

Figure 17B:
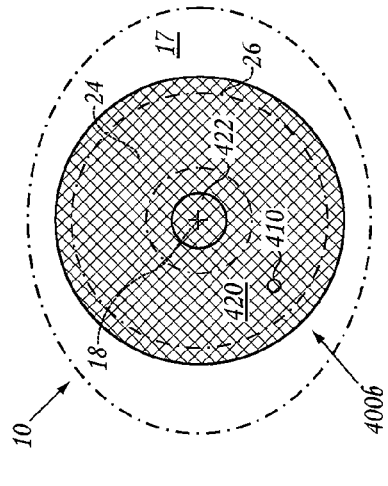
FIGS. 17A-17D depict a number of embodiments of eyeholders having aspects of the invention having alternative configurations of a contact member.
Figure 17D:
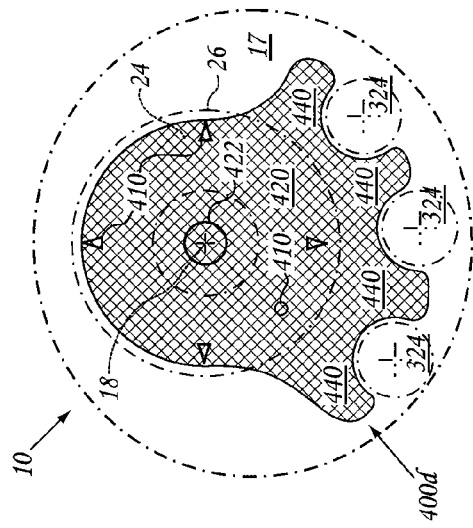
Figure 17A:
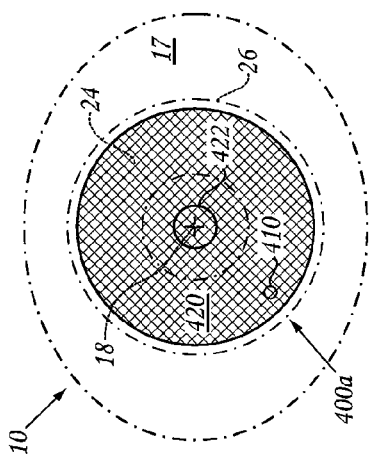

FIG. 17A depicts an embodiment in which contact member 420 is sized to have a margin which may be positioned on the eye surface so as to leave all or most of the limbus boundary 26 uncovered. This configuration facilitates visual confirmation of placement of member 420. This configuration also facilitates the use of automated pattern recognition/boundary detection methods, for example, using images captured by camera 102, or another camera disposed to capture images of the limbus. For example, proximity detector 103 in FIG. 1 may in certain embodiments include an optical rangefinder camera, which may also be employed to determine the position of limbus 26 with respect to contact member 420.

FIG. 17B depicts an embodiment in which contact member 420 is sized to cover all or a portion of limbus 26. In certain embodiments the comparatively large contact or cup member 420 provides greater stability of eye control for a given combination of bias force and/or vacuum pressure, and may facilitate a contour which avoids direct contact with the center of the cornea. Note that member 420 may comprise a transparent material permitting visualization of the covered portion of limbus 26.

Figure 17C:
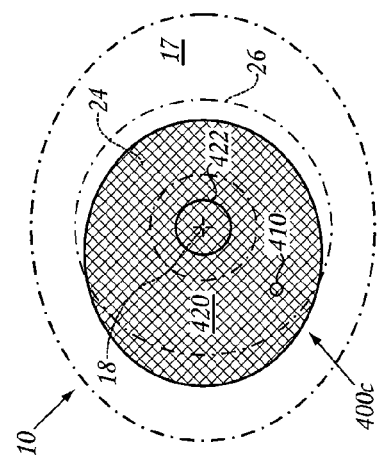

FIG. 17C depicts an embodiment in which contact member 420 is configured to be asymmetrical with respect to limbus 26, and in operation may be positioned off-center with respect to the limbic center (see axis 18).

FIG. 17D depicts an embodiment in which contact member 420 is configured to include one or more lobes 440, the lobes extending beyond the limbus 26, covering sclera regions adjacent one or more treatment beam entry regions 324. In the embodiment shown, the lobes surround portions of a pattern of three radially arranged treatment beam entry regions similar to those shown in FIG. 3D. For example, in an eyeholder for use in an orthovoltage X-ray treatment system, the lobes may comprise a material selected to absorb X-rays, e.g. to reduce dosage absorbed by the lens of the eye. In this example, a large portion of limbus 26 is exposed in portions of the eye surface not proximate to the treatment beams, and one or more fiducials 450 may be arranged to facilitate optical tracking devices. In alternative embodiment (not shown) the lobes may completely surround the beam entry regions 324.

Figure 5A:
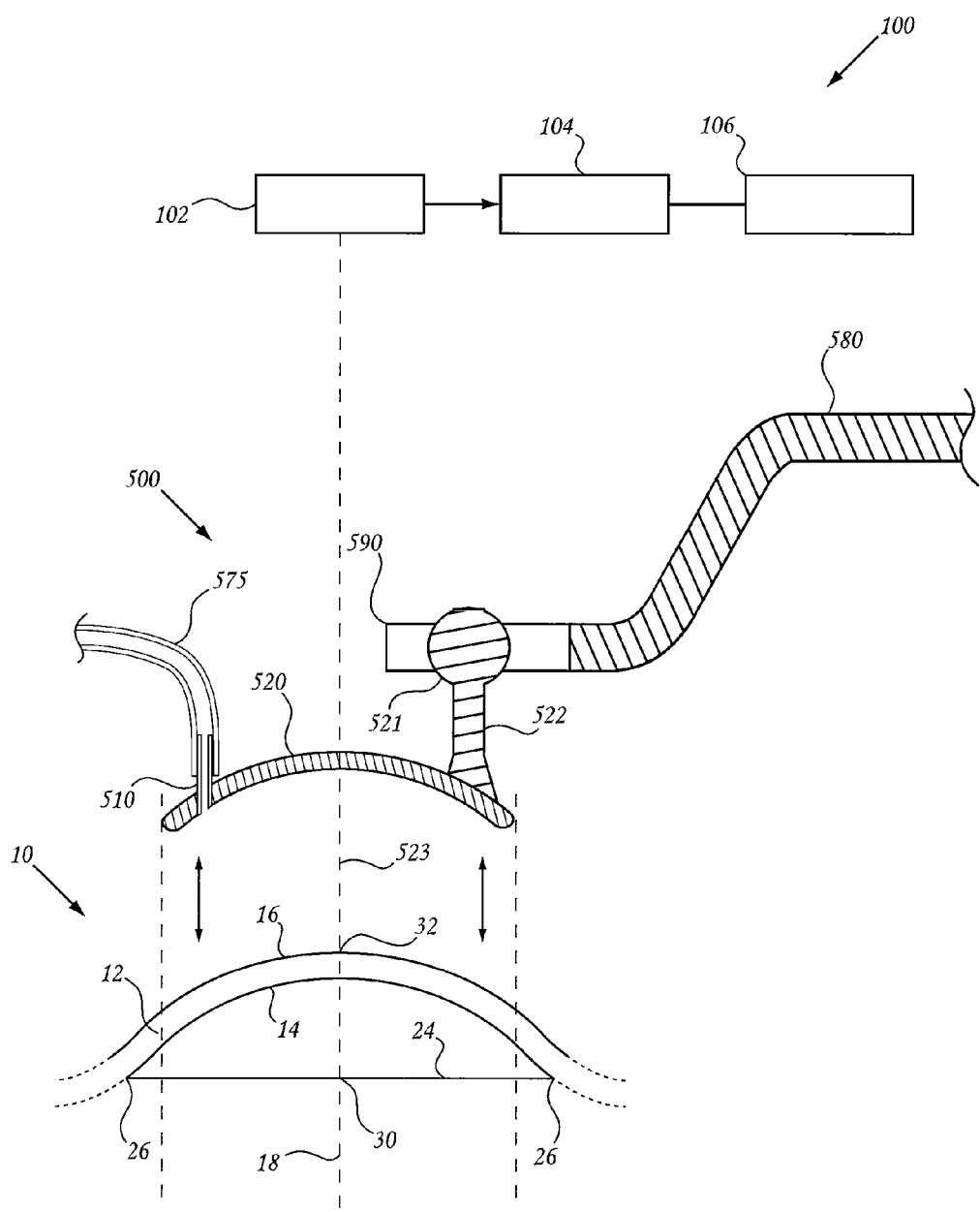

FIG. 5A depicts a configuration of an eye holder 500, which is generally similar to eye holder 400 shown in FIGS. 4A-B, but in which the post 522 is off-center from the central portion of the contact member-scleral lens cup 520. In particular, the offset from the center axis of the ocular guide, indicated at 523, is sufficient to allow a light beam aimed along this axis to be reflected off the outer center region of the ocular guide, unobstructed by a positioning arm 522 and a positioning arm 580. This allows outer surface of the ocular guide, normal to and intersecting axis 523, to provide a point of reflection for a beam aimed at the center of the eye, thus producing a Purkinje reflection that corresponds to the first Purkinje reflection from the anterior of the cornea, when the ocular guide is centered on the patient's eye. As in the embodiments of FIGS. 4A-B, an optional vacuum source 575 is also provided in this embodiment to provide suction engagement of cup 520 with eye 10. All or a portion of contact member 520 may comprise a transparent material, e.g., a clear polymer such as PMMA (polymethyl methacrylate), to permit an operator to see the relative position of eye structures such as the limbus 26 and iris 24 as contact member or cup 520 is brought into contact with eye 10.

Additionally, transparency permits transmission of light into and back from the eye surface and interior through cup 520 while it is in contact with eye 10, so as to enable observation internal eye structures through the cornea, such as the retina. Imaging camera 102 is also provided in this embodiment. A feature of this embodiment is that the imaging camera 102 can visualize an eye structure such as the fundus directly through the cup 520 while a therapy is being performed. A fundus image can be obtained through the clear portion of the scleral cup 520 without the post in the way. The Purkinje of the contacting portion 520 and its center align to the Purkinje of the cornea and the alignment position 523 of the contacting portion 520 can be used as a surrogate for what would be the alignment if the Purkinje of the cornea was used for alignment 18.

Figure 5B:
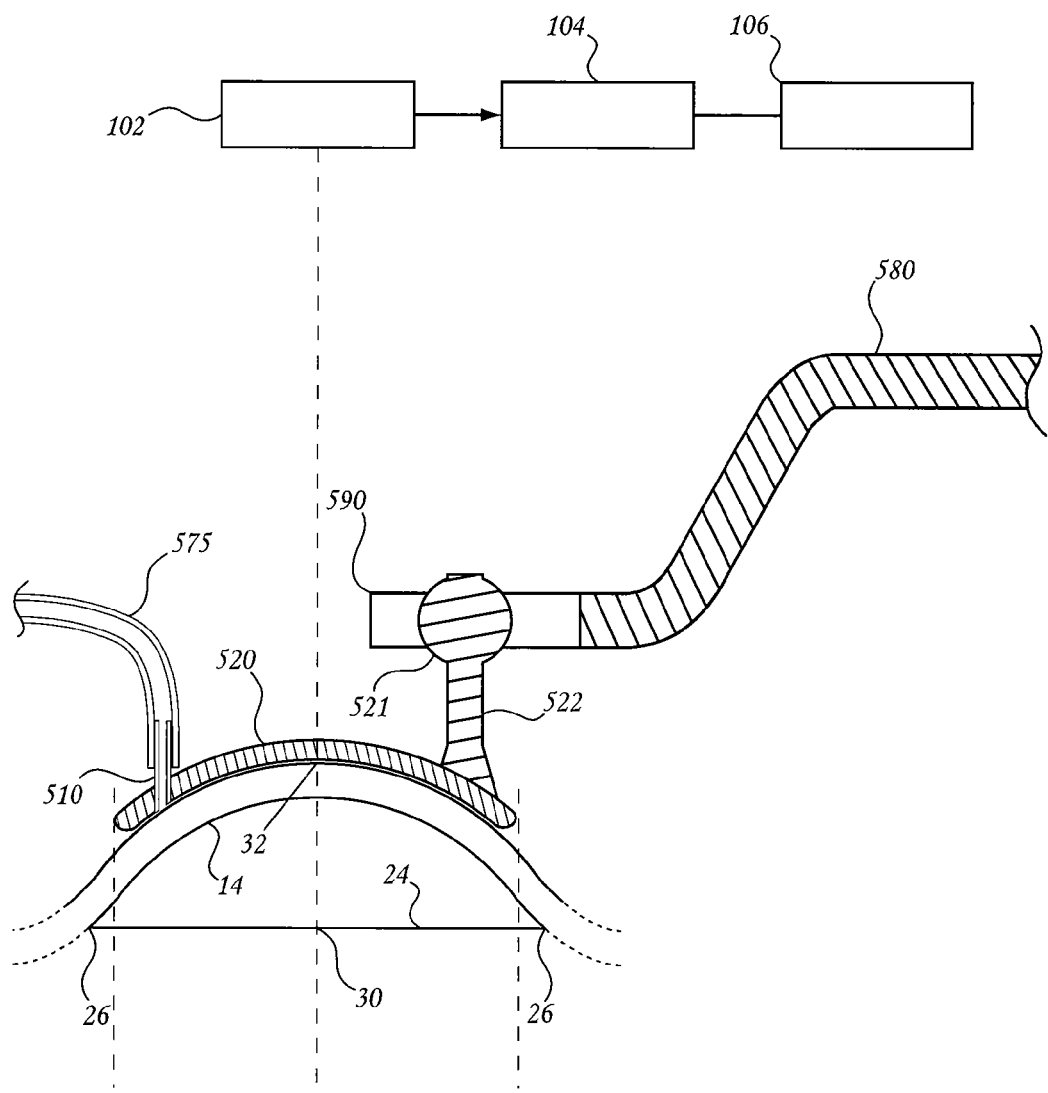

FIGS. 18A-18B depicts embodiments of eyeholders 500 (*a-b*) having aspects of the invention, similar in many respect to those shown in FIGS. 5A-B and 16, having alternative configurations of contact member 520. For each figure, the eyeholder 500 is shown superimposed on a schematic view of a portion of an eye 10 having iris 24 adjoining region of sclera 17, the junction of which defines limbus 26. Each figure includes a frontal view (1) and a cross-sectional view (2) taken along line (2)-(2) in view (1).

FIG. 18A depicts an embodiment in which contact member 520 is configured to include a window area 595 comprising a transparent material, permitting visualization of the eye interior through the central cornea while eyeholder 500a is in contact with the eye 10 (or the entire contact member 520 may comprise a transparent material). The window 595 may also be configured to facilitate visualization or capture of an image to the reflection of a collimated or coherent light beam from the outer surface of window 595, as describe in the alignment methods herein. Vacuum port 510 is configured to apply a suction force adhering eyeholder 500a to eye 10. Note that any space between window 595 and the corneal outer upper surface 16 may be filled with an ophthalmic solution or gel, which may be composed to reduce refractive effects between window 595 and the cornea. Support post 522 may be arranged to mount to contact member 520 off-center with respect to window 595, so as not to obstruct visualization through the window. In this example, contact member 520 is sized-shaped to leave all or a greater portion of limbus 26 uncovered.

FIG. 18B depicts an embodiment in which eyeholder 500b is configured in a generally similar arrangement to eyeholder 500a of FIG. 18A, but in which a central opening 597 is provided so that the central cornea surface 16 is exposed. Contact member 520 is configured in an annular ring shape which surrounds all or a portion of the boundary opening 597. Alternatively, member 520 may be not be entirely closed about the periphery of opening 597, for example having a "C" shaped planform rather than an "O" shaped planform. In the example shown, an annular grove 512 is recessed into the under surface (eye-contact surface) of member 520, to facilitate the distribution of vacuum pressure form communicating vacuum port 510 around the peripheral contact area of member 520. The embodiment shown permits a first Purkinje reflection to be conveniently captured or visualized from the outer corneal surface 16 while eyeholder 500b is in operative contact with eye 10, facilitating embodiments of the alignment methods described herein.

FIGS. 16A through 16B depict alternative species having aspects of the invention of a "breakaway" post fitting which may be employed with eye positioning and/or stabilizing devices such as shown in FIGS. 4A-B and 5A-B. It is advantageous to have a eye stabilization device 400 as shown in FIGS. 4A-B (or 500 as in FIGS. 5A-B) in which the eye contact member or cup 420 (520) can remain coupled to the eye 10 in the event that a patient voluntarily or involuntarily pulls away from the alignment system 100 after the contact member is coupled to the eye, or if the operator determines to disengage positioning arm 480 (580) at some point in a patient procedure. For example, a patient may sneeze or become startled during the course of a procedure, causing the patient to move involuntarily.

Each of FIGS. 16A through 16F depicts a portion of an eye positioning/stabilizing system 400 (500) eye contact member 420 (520) mounted to a multi-part post 422 (522), comprising a proximal post portion 422a (522a) coupled to the contact member and a distal post portion 422b (522b) coupled to the eye stabilization device, the post proximal and distal portions being configured to releasably engage one another. Each of FIGS. 16A-16F includes matched pair of views, in which view (1) shows the proximal and distal portions 422a -422b engaged, and view (2) shows the proximal and distal portions 422a -422b disengaged in exploded view.

Each of the species of FIGS. 16A-16F may further include a vacuum line and source as described above. In some embodiments, the vacuum line 475 (575) may be mounted and connected so as to remain attached to the eye contact member 420 when the post portions 422a,b are disengaged. For example, in one embodiment, the vacuum line and source may be mounted to a patients clothing (such as a collar) so as to remain with the patient, should the patient move away from the overall system 100. Likewise, each of the species of FIGS. 16A-16F may be employed with a bias force applied by the positioning arm (480 in FIGS. 4A-B) as described above.

It should be understood that the mechanisms illustrated in FIGS. 16A-16F are exemplary, and variations will be apparent to one skilled in the art without departing from the spirit of the invention. For example, the configurations of post distal and proximal portions may generally be reversed. Likewise, the devices may include sensors configured to signal control system processors upon engagement or disengagement of portions 422a,b.

FIG. 16A shows a device 400 in which the distal and proximal are profiled to provide a socket 422a and post 422b in which the engagement only transmits significant compression force, but transmits little or no tensile force perpendicular the eye (e.g., is maintained in position by bias force), while resisting lateral force. The distal-proximal portions may be permitted to swivel axially, or axial torque may provide, if desired, by a keyed arrangement on the sides or bottom of the socket (not shown).

FIG. 16B shows a device 400 in which the distal and proximal portions 422a,b are generally similar to that of FIG. 16A, but in which the socket and posts are profiled to provide a light "snap-bead" effect wherein one portion grips the other upon disengagement. Either or both of portions 422a,b may comprise an elastic material, and slots may be incorporated in either socket or post portions to increase flexibility.

FIG. 16C shows a device 400 in which the distal and proximal portions 422a,b include a magnetic coupling, for example where a permanent or electro magnet and/or ferromagnetic material is incorporated into one or both of portions 422a,b, so as to create a pre-defined attraction force between the engaged distal and proximal portions.

FIG. 16D shows a device 400 in which the distal and proximal portions are generally similar to that of FIG. 16C, which additionally or alternatively includes an adhesive material which releasably bonds portions 422a,b together, e.g., in the manner of adhesive tape or "post-it" products.

FIG. 16E shows a device 400 in which the distal and proximal portions 422a,b are generally similar to that of FIG. 16A, but in which the socket and posts are deeply engaged so as to apply lateral force at a selected distance above the surface of the eye contact member.

FIG. 16F illustrates the adaptation of any one of the species of FIGS. 16A-E to a "side-post" device 500, in which the post structure 522a-522b is positions sufficiently off-axis so as to provide an unobstructed center portion 595, which may be transparent (a window for light transmission) to enable certain methods having aspects of the invention as described herein.

Alignment by Limbus Sizing

Figures 6A, 6B, 6C:
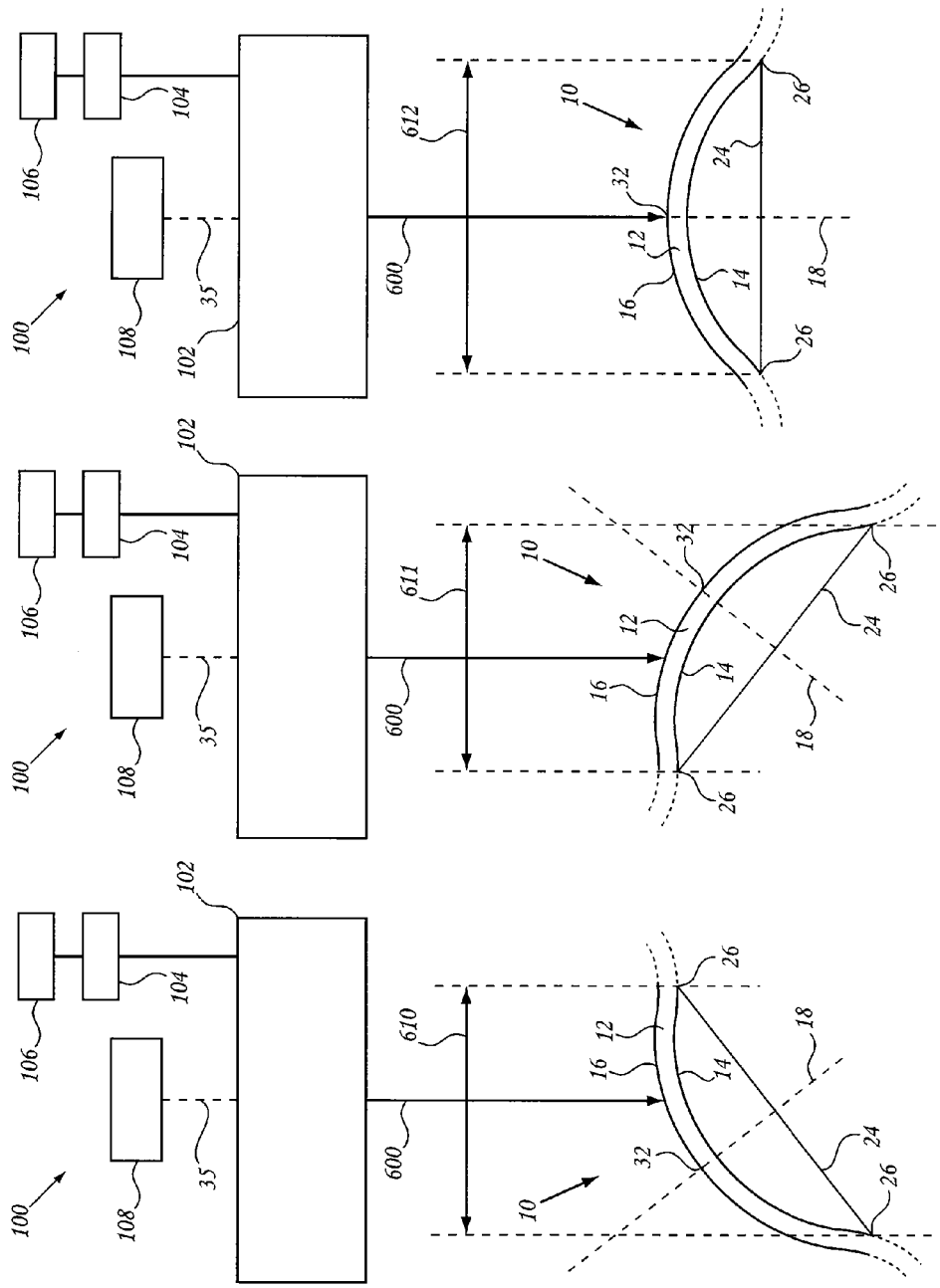
FIGS. 6A-C illustrate schematic side views of an anterior portion of an eye in three orientations with respect to an embodiment of an alignment system having aspects of the invention, depicting a method utilizing limbus sizing to define the reference axis.

In another embodiment of the invention, the alignment method utilizes limbus sizing to define the geometric axis. In this embodiment, as illustrated in FIGS. 6A-C, a schematic side view of a portion of an eye 10 is shown. The alignment system and method in this embodiment of the invention is based on the detection of the maximal area of the limbus 26 of the subject's eye 10. The cornea 12 of eye 10 is characterized by an anterior surface 16 and a posterior surface 14 that are concentric with one another, the iris 24 extending outward to posterior surface 14 of cornea 12. The circle of intersection between iris 24 and interior surface 14 is an anatomical landmark known as the limbus 26. The limbus of an eye is readily imageable.

As discussed above, an "axis of interest" indentified as a reference axis for eye alignment method embodiments having aspects of the invention may advantageously be, but is not necessarily, the optical axis or the geometric axis of the eye. The geometric axis 18 in FIGS. 6A-C, may be determined to be aligned with the external coordinate system of system 100 when axis 18 is coincident with the center of the limbus 26 when the area circumscribed by the boundary of the limbus is positioned to achieve its maximum apparent area with respect to camera 102. In the illustrated embodiment, camera 102 is positioned to image eye 10 along direction 600. Light from light source 108 travels along path 35, entering the eye 10 through the cornea 12 and is directed by the lens to the retina. Camera 102 provides video image data of eye 10 to display 104. Coupled to display 104 is an image generator 106. In operation, image generator 106 generates an image of the limbus 26 and displays it on display 104. Accordingly, as a first step, image generator 106 can be operated to generate a first image of limbus 26 when the eye is in a first position, as shown in FIG. 6A. Image generator 106 can then locate the boundary of limbus 26.

Next, the first area defined by the boundary of the limbus is determined. As shown, FIG. 6A depicts eye 10 angled such that the area 610 defined by the boundary of the limbus is less than maximal. The camera 102, or preferably the eye 10, is then positioned in a second position and image generator 106 is operated to generate a second image of limbus 26, as shown in FIG. 6B. Image generator 106 can then locate the boundary of limbus 26. Next, the second area 611 defined by the boundary of the limbus is determined. As shown, FIG. 6B depicts eye 10 angled such that the area 610 defined by the boundary of the limbus is less than maximal. This process is repeated until the maximum area defined by the limbus boundary is identified, as illustrated in FIG. 6C, where direction 600 is co-aligned with the reference axis 18. Detection of the maximum area 612 of limbus 26 signals the eye is in alignment with the system, and the reference axis 18 is defined.

Identification of the Limbic Boundary

Figure 7:
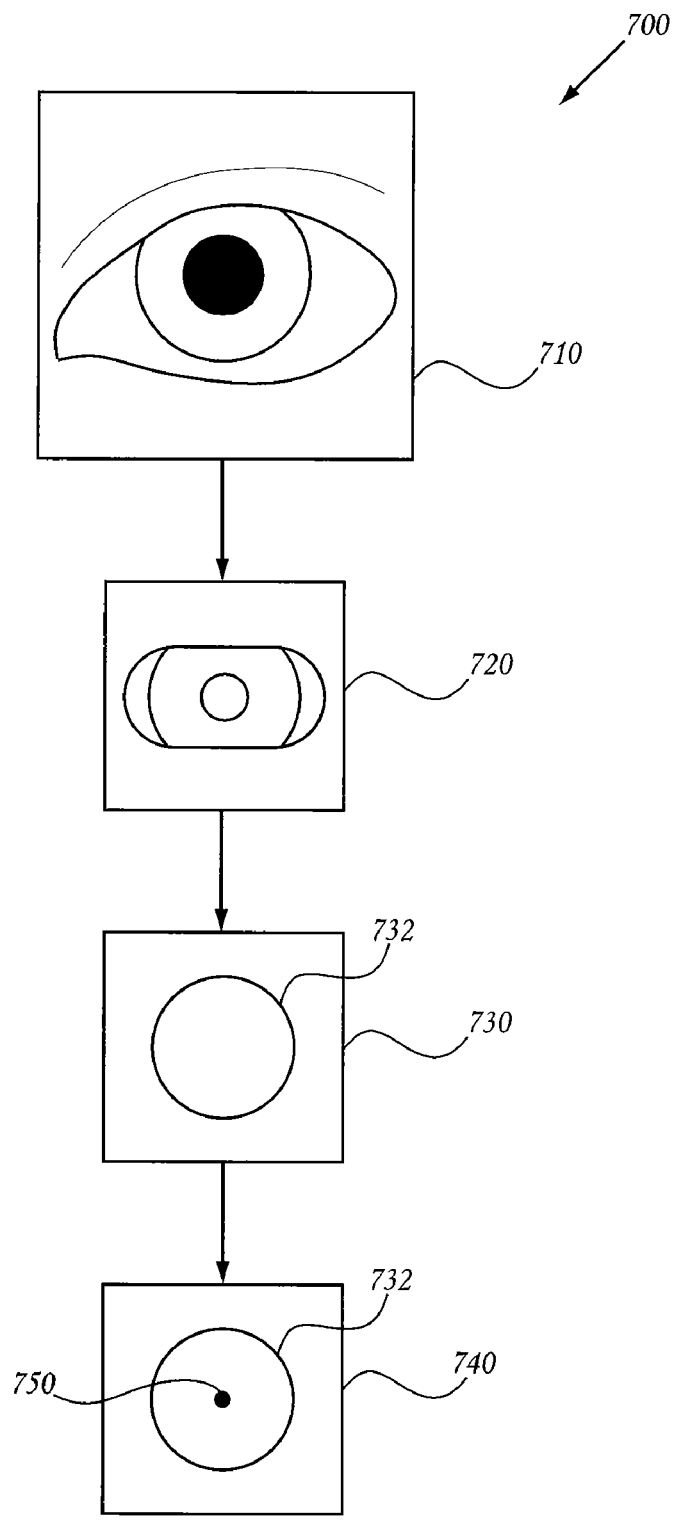
FIG. 7 is a diagram of an exemplary method having aspects of the invention, showing a sequence of the successive data processing steps used to identify the limbic boundary and limbic center.

As noted above, the limbic boundary is determined in the alignment methods described. Determination of the limbic boundary, and limbic center, can be accomplished in a variety of ways. An exemplary method for determining the center of the limbus is diagrammatically illustrated in FIG. 7, showing the sequence 700 of the successive data processing steps to identify the limbic boundary and limbic center. Input image 710 represents the relatively high-resolution eye image data that is applied. The first data processing step 720 is to average and reduce input image 710. This can be accomplished by convolving the data defining input image 710 with a low-pass Gaussian filter that serves to spatially average and thereby reduce high frequency noise. Since spatial averaging introduces redundancy in the spatial domain, the filtered image is next sub-sampled without any additional loss of information. The sub-sampled image serves as the basis for subsequent processing with the advantage that its smaller dimensions and lower resolution lead to fewer computational demands relative to the original, full size, input image 710.

The next data processing steps involved in localizing the limbus boundary, and center of the limbus, include the sequential location of various components of the limbic boundary. In sequence, step 730 locates the limbic (or outer) boundary 732 of the iris. The localization step can be performed in two sub-steps. The first sub-step includes an edge detection operation that is tuned to the expected configuration of high contrast image locations. This tuning is based on generic properties of the boundary component of interest (e.g., orientation) as well as on specific constrains that are provided by previously isolated boundary components. The second sub-step includes a scheme where the detected edge pixels vote to instantiate particular values for a parameterized model of the boundary component of interest.

In more detail, for the limbic boundary 732 of step 730, the image is filtered with a gradient-based edge detector that is tuned in orientation so as to favor near verticality. Thus, even with occluding eyelids, the left and right portions of the limbus should be clearly visible and oriented near the vertical, when the head is in an upright position. The limbic boundary is modeled as a circle parameterized by its two center coordinates, xc and yc, and its radius, r. The detected edge pixels are thinned and then histogrammed into a three-dimensional (xc, yc, r)-space, according to permissible (xc, yc, r) values for a given (x, y) image location. The (xc, yc, r) point with the maximal number of votes is taken to represent the limbic boundary. Finally, with the limbic boundary 732 isolated, the final processing step 740 includes locating the center 750 of the limbus.

The above-described approach to identifying the center of the limbus can be generalized in a number of ways. For example, image representations other than oriented gradient-based edge detection may be used for enhancing iris boundaries. Second, alternative parameterizations for the iris boundary may be employed. Finally, iris boundary localization may be performed without the initial steps of spatial averaging and subsampling.

Defining the Retinal Target Region Following Ocular Alignment

As described above with respect to FIGS. 1-5, a first Purkinje reflex (or an equivalent reflection from an corneal covering member, such as eye contact member 420 or 520) may be correlated and aligned relative to the center of the limbus 26 to define a reference axis 18. The center of the limbus may be manually or automatically detected as described with respect to FIGS. 6-7. Further the reference axis may be aligned with the external coordinate system of an eye positioning/stabilization system and/or eye treatment.

One method embodiment having aspects of the invention includes aligning the eye with the system coordinates and defining the reference axis, and identifying a treatment target tissue region relative to the intersection of the reference axis with a portion of the eye, e.g., the retina. With the eye aligned as described above, and the reference axis defined and correlated with an external coordinate system, a treatment target tissue region within the eye can be identified and located within the external coordinate system.

In a further method embodiment having aspects of the invention includes, after a treatment target tissue is located with respect to the ocular reference axis as defined and aligned with respect to a treatment system, the treatment device is positioned relative to this reference axis to deliver a desired treatment to the target tissue (e.g., a retinal target region at or near the macula).

Figure 8A:
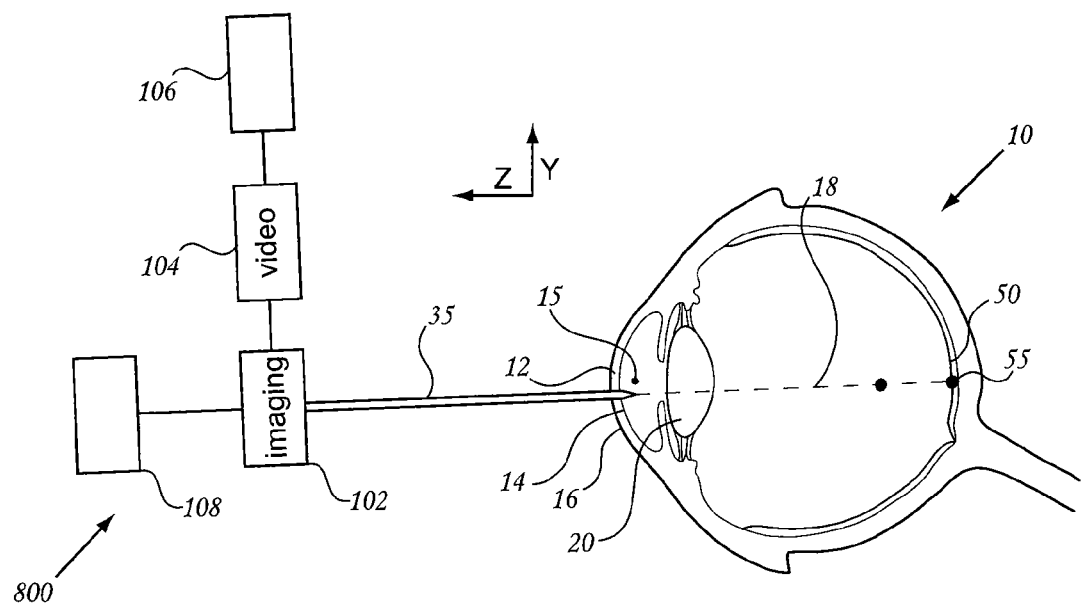
FIGS. 8A-B illustrate a reference axis defined in an embodiment of an alignment system having aspects of the invention, oriented so that the center of collimated light reflection from the retina coincides with the center of the limbus.

FIG. 8A depicts a cross-section of a subject's eye 10 in a saggital (Z-Y) axis to include an anterior corneal surface 16, a posterior corneal surface 14, a lens 20, and a retinal surface 50, in association with system 800. System 800 includes a collimated light source 35 illuminates a cornea surface 16 and its focal point 15 as shown. Note in this regard that the eye positioning and stabilization devices having aspects of the invention, and described with respect to FIGS. 5A-B provide for a transparent eye contact member or cup 520, permitting a path for light transmission to and from external and/or internal structures of eye 10, while the eye is stabilized or positioned. Although the focal point is depicted in front of the lens 20, the focal point can focus behind the lens and closer to the retina 50 as well depending on the power (diopters) of the cornea 12 and/or lens 20. Axis 18 is the extension of the collimated light source path 35 through the anterior-posterior axis of an eye and to the retina 50. As long as the collimated light source travels through or close to the center of the lens, the collimated beam will not be refracted to a great extent. This is important in the radiotherapy treatment because radiation travels in a straight line through the eye.

Device 102 includes an imaging device such as a fundus camera or an optical coherence tomography (OCT) machine. The principles of OCT are familiar to those skilled in the art and for the purpose of the present invention encompass optical coherence reflectometry and other forms of optical interferometry. Additional imaging devices contemplated by the present invention include CT Scan, MRI, A- or B-scan ultrasound, a combination of these, or other ophthalmic imaging devices such as a scanning laser ophthalmoscope.

Figure 8B:
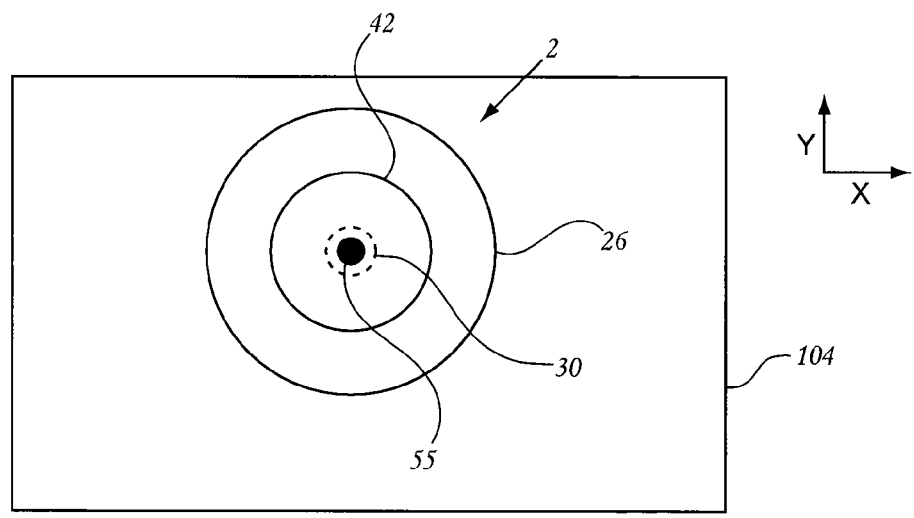

In FIG. 8B, a video image 104 is depicted of a frontal (X-Y) view of the eye 10 in the configuration shown in FIG. 8A. Point 55 represents focal spot 15 as viewed on an imaging monitor 104 using an imaging device 102 which can detect the wavelength of light from the collimated light source 108. Limit 42 is a pupil in FIG. 8B. Region 30 is a circle, the center of which coincides with the center of the limbus 26. Collimated light source 108 can be positioned in the X-Y axis so that the center of its reflection 55 coincides with the center 30 of the limbus 26. The limbus of an eye is readily imageable; to the extent the limbus 26 is imageable with the same camera as the reflection of the collimated light source 12, both centers can be aligned in the X-Y axis. With such alignment, intersection of the reference axis 18 with the retina can be determined.

In some embodiments, a treatment axis may be defined off-set from the reference axis 18. The treatment axis may be parallel to the reference axis, selected so that the target is its intersection with the retina. Treatment beams may then be positioned with respect to the treatment axis, for example, at selected angles of rotation about the treatment axis.

Figure 9A:
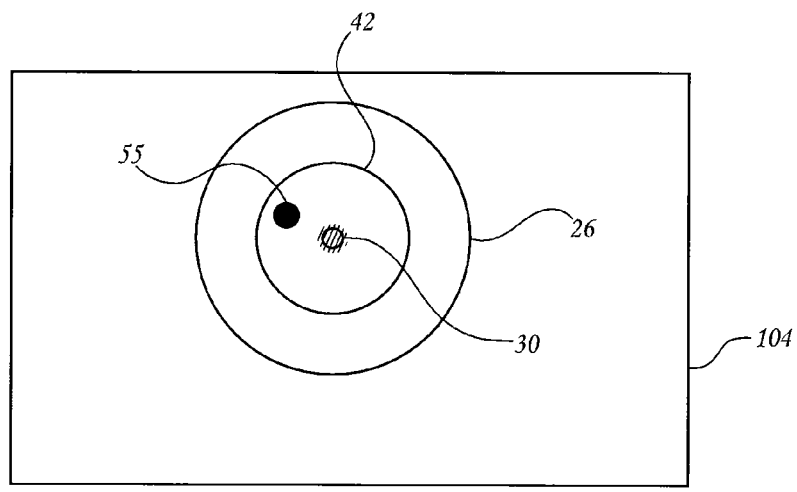
FIGS. 9A-B illustrate an embodiment of an alignment system generally similar to that of FIGS. 8A-B, in which the center of collimated light reflection from the retina is now off-center or off-axis with respect to the center of the limbus.
Figure 9B:
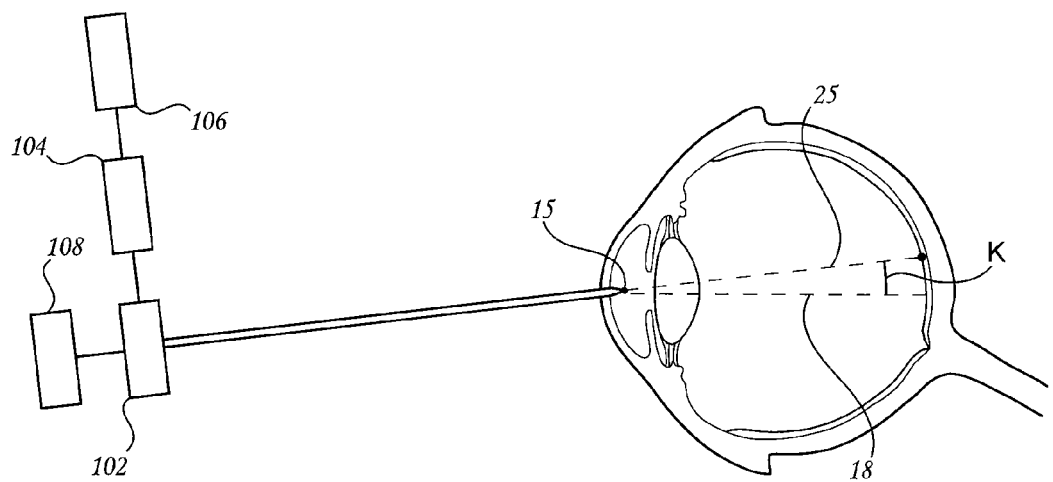

In certain cases, the axis 18 coincides with a region close to the macula on the retina 50. See FIG. 11 for greater detail. This point can be called the center of the posterior pole of the eye FIG. 9A depicts an example where the center of the collimated light focus 55 in the X-Y plane, depicted on the video monitor 104, is not coincident with the center of circle 30 (the center of the limbus 26). FIG. 9B depicts the corresponding case when viewed in the anterior-posterior (Y-Z) axis of the eye, in association with alignment system 900. Focal spot 14 is now off-center or off-axis as shown in FIG. 9A in the frontal view. The beam 35 from light source 108 extensions through the eye to the retina and is depicted in FIG. 9B as axis 25. Axis 25 is different from the reference axis 18 in the Y-Z plane; axis 25 is an axis in which a collimated light beam would be refracted and its position on the fundus affected by the refraction. Axis 18 is the axis in this figure which depicts a Y-Z axis which aligns to a point near the macula (see FIG. 11 for greater detail).

Figure 10:
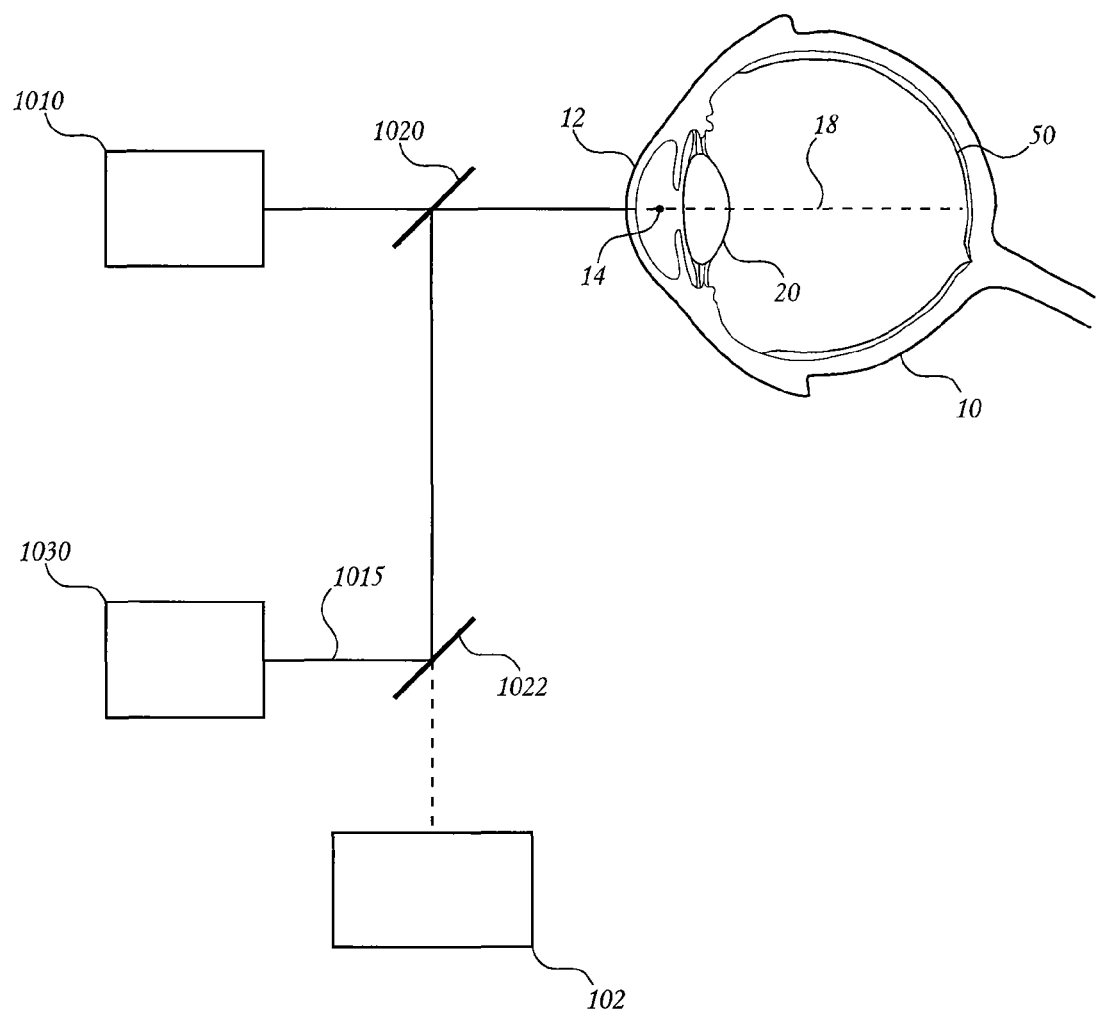
FIG. 10 depicts an embodiment of an alignment system having aspects of the invention, including beam splitters to superimpose the reflection of a laser beacon aligned with a reference axis upon the image obtained of a subject's retina by a fundus camera.

FIG. 10 depicts a configuration of a device utilized to achieve the results in FIGS. 8A-9B. An eye 10 is depicted in FIG. 10 in a Y-Z plane and the cornea 12 of the eye depicted on the front surface. A fundus image (see FIG. 11) can be obtained simultaneously by fundus camera 1010. Laser beacon 1015 projects from laser source 1030 to the retina and can be aligned to the reference axis 18 by aligning it with the center of the limbus and simultaneously aligning with its focal spot 15, represented by its reflection in an ordinary imaging camera 102. Beam splitter 1020 allows deflection of the laser beacon 1015 so that it can be transmitted through the reference axis of the eye 10. Infrared light from the fundus camera 1010 can pass through the beam splitter 1020 so that the fundus can be imaged simultaneously with the laser beacon 1015 on the fundus image through fundus camera 1010. Beam splitter 1020 can at least partially reflect incident white light so that the camera 102 can image the eye. Beam splitter 1022 reflects the laser beacon beam 1015 and also at least partially transmits white light so that it can image the front of the eye in the X-Y plane; that is, the plane on the front of the eye. The system also includes an X-Y position device which enables the laser beacon 1015 to be moved to different positions along the X-Y axis on the front of the eye. A position sensing element (PSD) can also be included in the path of the laser beacon or using an additional beam splitter to detect movement or stability over time of the beacon. Imaging software integrated with, or linked to, the camera 102 can allow stability of the eye 10 to be quantified over time as well.

Figure 11A:
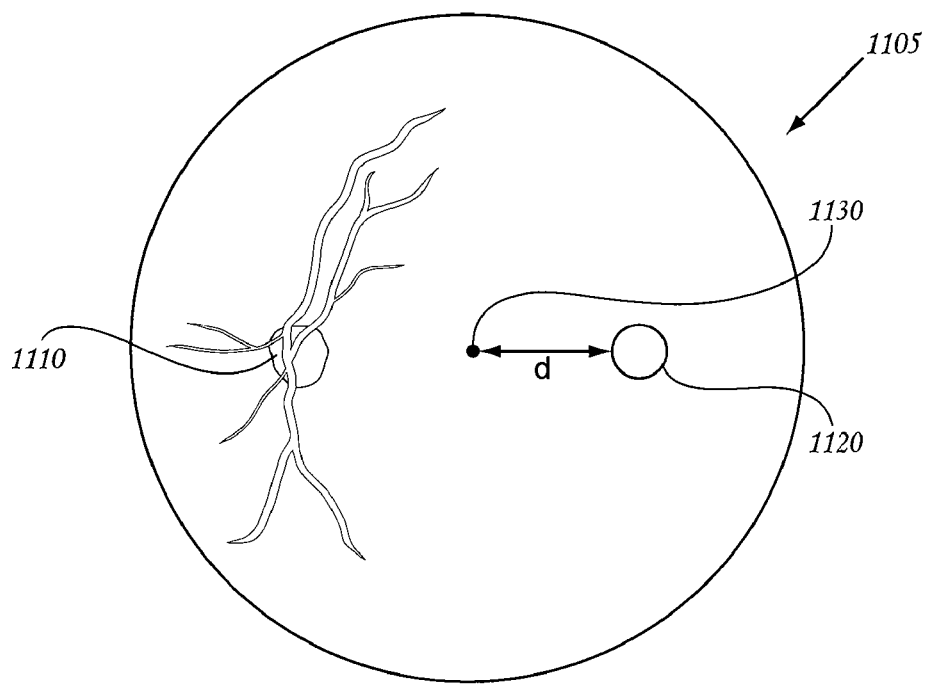
Figure 11B:
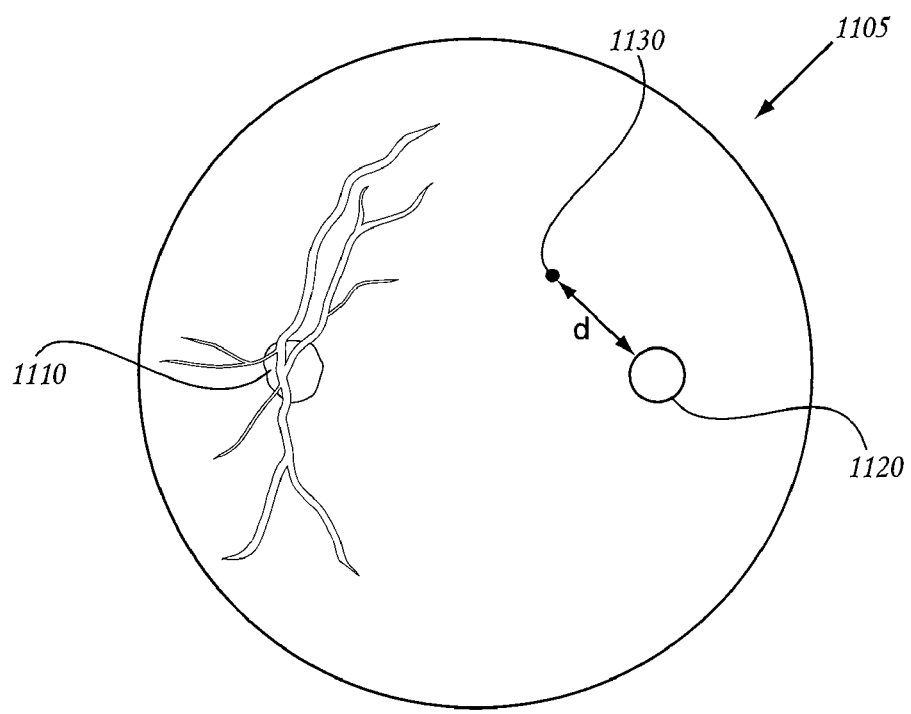

FIG. 11A depicts a fundus image 1105 obtained with the system in FIG. 10 when the focus of the laser beacon and the laser beacon spot entry are aligned on the center of limbus. The projection of the laser beacon to the fundus 1105 is the point of intersection of the reference axis with the retina 1130, and in this embodiment coincides with the approximate center of the optical or geometric axis of the eye. For reference, the optic disc 1110 and the macula/fovea 1120, or center of visual acuity, is shown and is set at a small offset "d" from the reference axis depicted by the beacon 1130. FIG. 11B depicts an illustration of the eye represented in FIG. 12B where the beacon 1130 is not aligned with the center of the limbus.

Figure 12A:
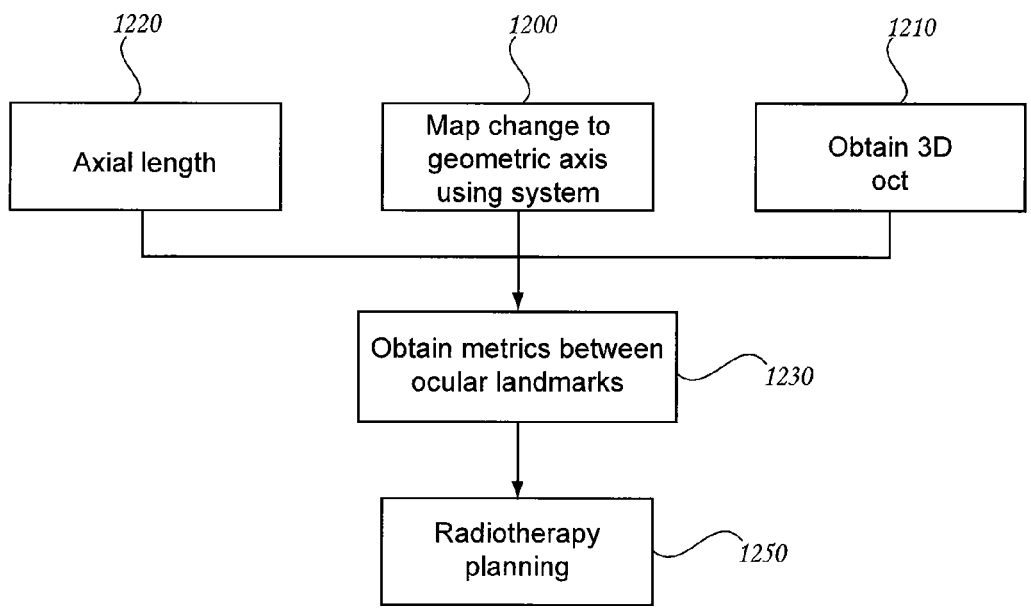
Figure 12B:
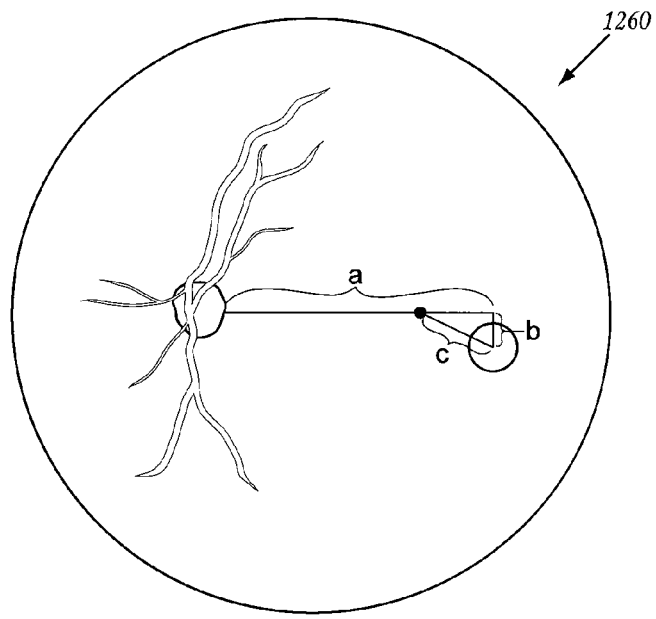

FIG. 12A depicts a summary of the methodology adapted to be used in a system to deliver radiation therapy to the macula of a patient. Alignment system 1200 is used to obtain a fundus image as shown in FIG. 12B. A three-dimensional OCT, or another instrument which can measure distances quantitatively on the retina, image 1210 is obtained so as to quantify distances between the optic nerve and fovea. The 3D OCT image 1210 can be mapped and registered to the fundus image shown in FIGS. 11A-B. Such registering allows for the fundus image with the laser beacon on the reference axis to be scaled for actual distances 1230 (a,b,c in FIG. 12B). Axial length measurement 1220 enables the 3D OCT or 2D OCT to be scaled for actual distances because these instruments rely on axial length to determine quantitative measurements of these parameters. Once the measurements are complete 1230, the limbus and cornea of the eye are registered to the macula both in the X-Y plane and in the Z plane. The laser beacon focus at a depth in the eye and its relationship to the sclera and limbus can be used in combination with metrics on the fundus to deliver radiation therapy.

Figure 13A:
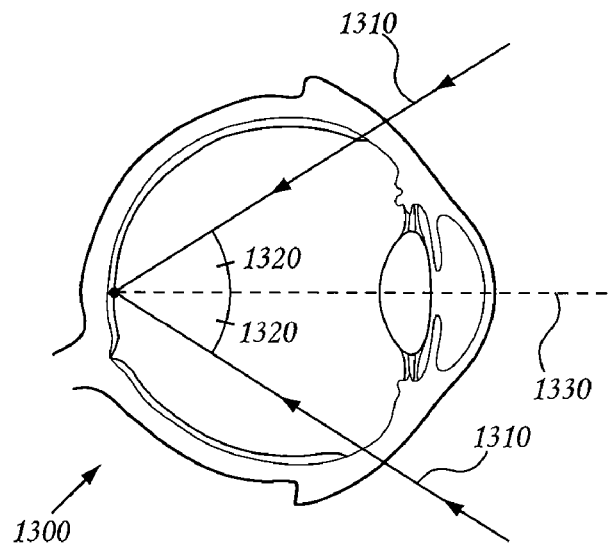

FIG. 13A depicts an x-ray therapy beam 1310 traveling through an eye 1300 at an angle 1320. These x-ray beams 1310 are referenced at angles 1320 to axis 1330. Depending on the intended target tissue of treatment, axis 1330 may be the optical axis, the geometric axis, or another axis defined as the treatment axis.

Figure 13B:
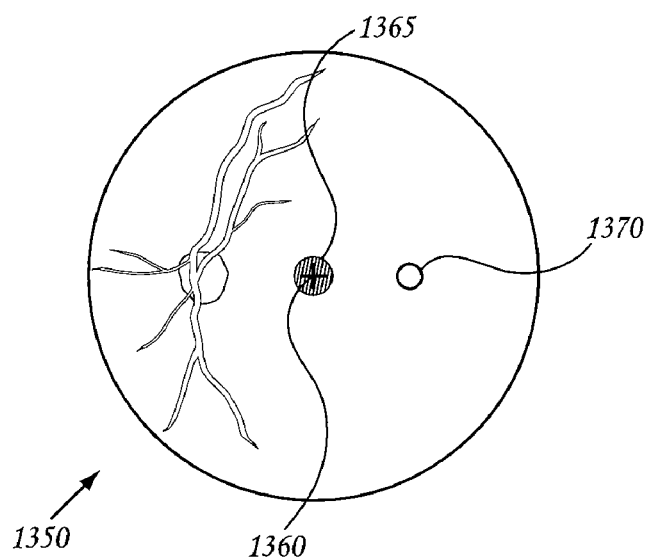

In FIG. 13B, the radiation therapy center 1365 is centered about geometric or optical axis 1360. With the physical metrics determined as discussed above in reference to FIGS. 12A-B, the relationship between the center of the limbus, the geometric or optical axis relative to the center of the limbus, and the macula are known.

Figure 13C:
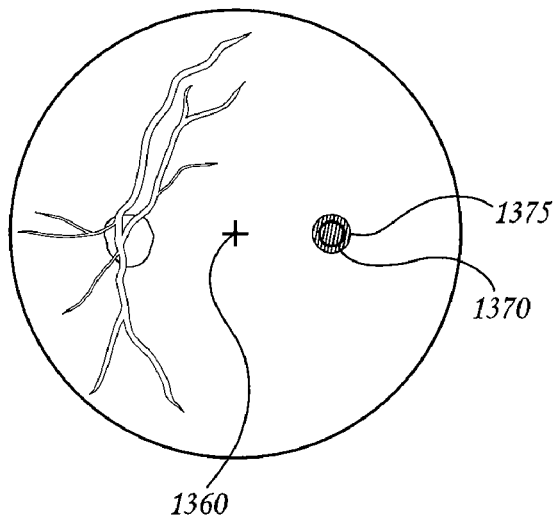

FIG. 13C depicts the center of radiation therapy 1375 coincident with the macula 1370 and not the geometric or optical axis 1360. In this radiotherapy planning system, the laser focus through the cornea in combination with the centering of the laser pointer on the center of the limbus enable a virtual fiducial, or surrogate, for the position of the macula, and therefore, allow the angles of the radiotherapy beams to tri-angulated to the macula without visualization. The system can similarly be used to calibrate a lens or other ocular contact device that a patient may wear for delivery of radiotherapy. In another embodiment, a lesion on the retina or a drusen deposit can be registered to the front of the eye.

Figure 14:
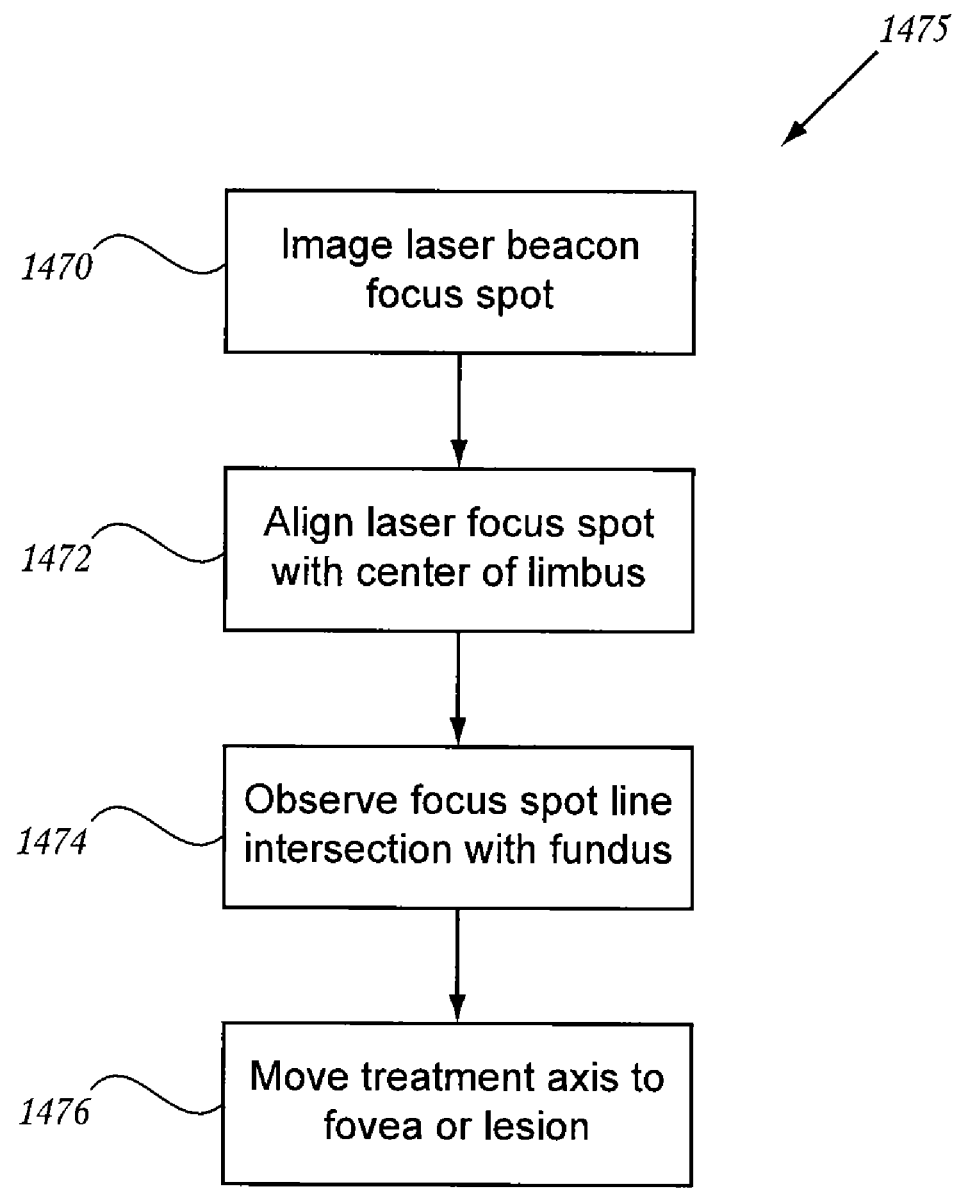
FIG. 14 is a diagram of an exemplary method having aspects of the invention, showing a sequence of the successive steps used to obtain the relationship between the center of the limbus, the optical axis, and the relative position of a beam traveling through the limbus.

FIG. 14 depict a method 1475 to use the system of the current disclosure to obtain the relationship between the center of the limbus, the optical axis of the eye, and the position a beam travels through the limbus relative to these positions when a patient fixates on an object. With these data, the relationship between the optical axis and the visual axis can be determined for an individual patient. The first step in the method is to image the laser beacon focus spot 1470, align the laser beacon focus with the center of the limbus 1472, and observe with the fundus imaging camera 1474 as described above. From this alignment with the optical/geometric axis, the center of treatment can be maintained in this position or it can moved 1476 a distance to the fovea or the center of a lesion, defining a separate treatment axis.

Photoablative Eye Surgery System

Figure 15:
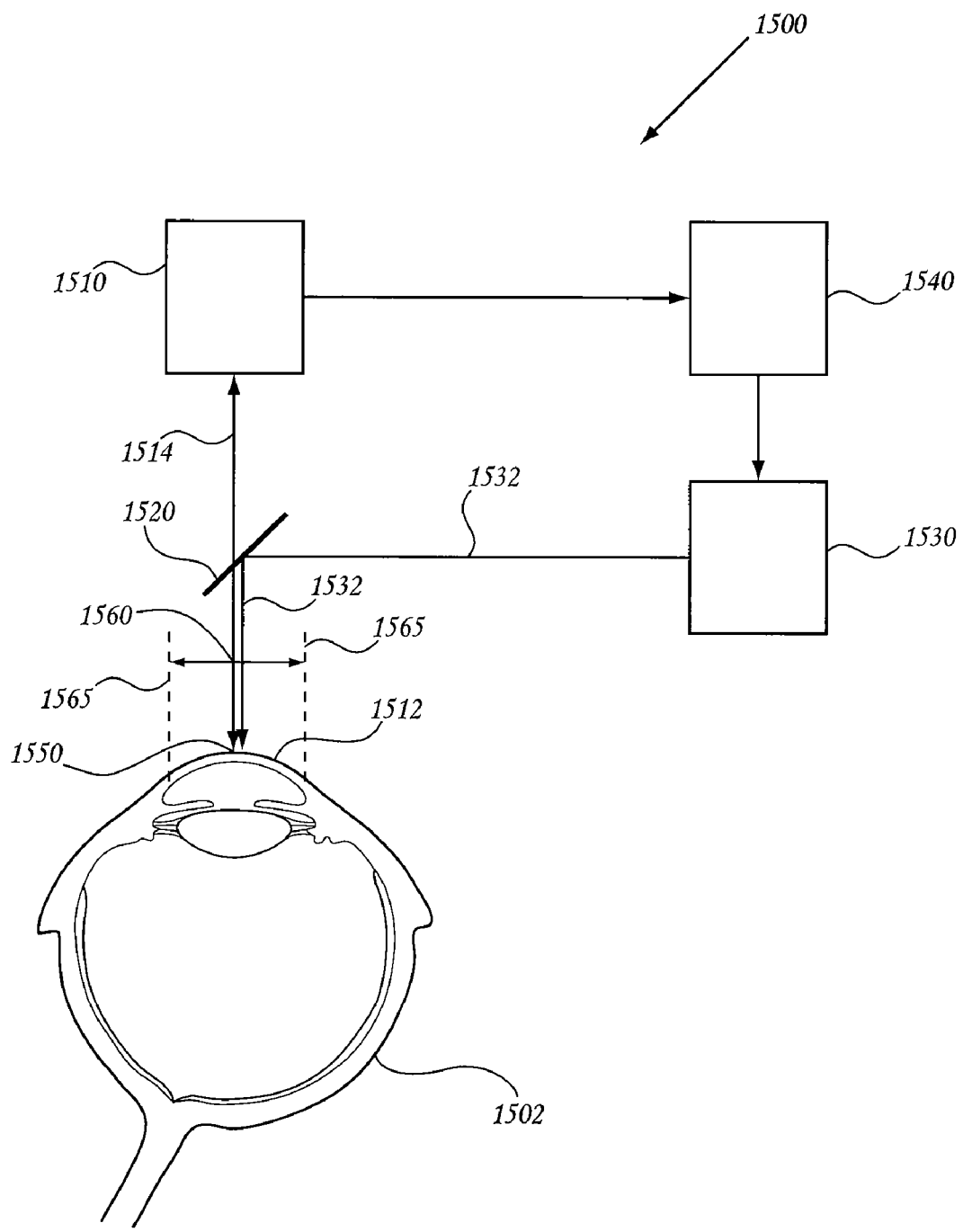
FIG. 15 is a diagram of an exemplary system having aspects of the invention, configured to administer photoablative eye surgery.

Use of the alignment method discussed above is, in one embodiment of the invention, applied to photoablative eye surgery. This eye surgery system embodiment of the invention is shown schematically in FIG. 15. The system 1500 can represent a photoablative eye surgery system for reshaping a patient's cornea represented by anterior corneal surface 1512. The system can include an OCT component 1510 that emits a probe beam 1514 which passes through beam splitter 1520 and propagates towards the eye 1502. The beam is apertured to preferably restrict the probe beam diameter. This is advantageous in that it restricts the probe beam scan over a small lateral dimension resulting in faster detection of the OCT signal. The probe beam is aligned to the reference axis of the eye by concentric co-alignment of the center 1560 of the limbus 1565 and the first Purkinje reflex 850 as discussed in detail above. The system can further includes a therapeutic laser component 1530 that emits a therapeutic beam having a beam propagation axis as shown at 1532. The probe beam 1514 from OCT component 1510 is co-aligned and coincident with therapeutic beam axis 1532 at the corneal surface. The location of therapeutic beam axis 1532 on the corneal surface during the therapeutic procedure is controlled by eye tracker 1540 in a manner well known to those skilled in the art. That is, the motion of the eye due to voluntary and involuntary movement is monitored in real time to coordinate the ablation of the cornea with the therapeutic beam.

The eye tracker 1540 includes at least one image capture device, such as a camera, to at least track the eye in real time. The image capture device can detect the position of the eye and relate the direction of the laser system to the position of the eye. An optional display directed to the operator of the laser system can depict the position of the laser device in real time in some embodiments. In some embodiments, the image capture device detects the position of the eye, and digitizing software is used to track the position of the eye. The eye is meant to remain within a preset position, or treatment field, which can correspond to the edges of the limbus. When the eye deviates beyond a movement threshold, a signal can be sent to the laser device. Movement threshold includes a degree or measurement that the eye is able to move and remain within the parameters of treatment without shutting the laser device off. In some embodiments, the movement threshold can be measured in radians, degrees, millimeters, etc. The laser source is turned off when the eye is out of position beyond the movement threshold, and the laser source is turned on when the eye is within the movement threshold. In some methods of setting the movement threshold, a treating professional delimits the edges of the limbus and treatment planning software then registers the edges of the limbus. If the limbus of the eye moves away from the delimited edge limit, a signal is sent to the laser device to shut down.

Radiotherapy System

In another embodiment of the invention, the alignment method is utilized to define an ocular axis of interest which intersects the retina at a retinal target region near the macula, and combined with a therapeutic treatment scheme in which a radiotherapy device is aligned to a needle placed at least partially through the sclera and even into the vitreous of the eye. A light guide, or pointer, can be placed into or coupled with the needle to illuminate the retina with a collimated light source. The needle and light guide can be stabilized within the sclera so that the collimated light source is stable on the retinal target region. The radiotherapy device can then be aligned with the needle to deliver radiation in a straight line along the needle and along the light guide path and to the desired retinal target region. With this treatment scheme, small regions of the retina can be precisely targeted.

The radiotherapy system used in combination with the alignment methods described above can be configured to deliver anywhere from about 1 Gy to about 40 Gy during a treatment period, or from about 10 Gy to about 20 Gy during a treatment period, to regions of the eye including, but not limited to, the retina, sclera, macula, optic nerve, the capsular bag of the crystalline or artificial lens, ciliary muscles, lens, cornea, canal of schlemm, choroid, and conjunctiva. In some embodiments, the system can be configured to deliver from about 15 Gy to about 25 Gy during a treatment period. In some embodiments, the system 10 is capable of delivering x-ray therapy in any fractionation scheme (e.g., about 1 Gy per day, about 5 Gy per day, about 10 Gy per month, or about 25 Gy per year), as the treatment planning system can retain in memory and recall which regions had been treated based on the unique patient anatomical and disease features. These features and previous treatments are stored in the treatment database for future reference.

The system can also deliver different photon energies depending on the degree of disease or the region of the eye being treated. For example, the x-ray generation tube can deliver photons with photon energies ranging from about 20 keV to about 40 keV, to about 60 keV, or to about 100 keV. It may be desirable to use photons with photon energies ranging from about 20 keV to about 50 keV for structures in the anterior portion of the eye because photons with these photon energies will penetrate less. It may be desirable to utilize photons with photon energies ranging from about 60 keV to about 100 keV or greater for structures in the posterior region of the eye for greater penetration to the retina. In some embodiments, the x-ray generation tube can emit photons with photon energies from about 10 keV to about 500 keV, from about 25 keV to about 100 keV, from about 25 keV to about 150 keV, from about 40 keV to about 100 keV, or any combination of ranges described above or herein. In some embodiments, selection of the photon energy can be based on diagnostic calculations, which can include a model of the eye created from anatomic data taken from the actual eye of the patient to be treated. The treating medical practitioner can choose the beam energies based on the disease and then set the machine to the desired energy level. In some embodiments, the system can receive input from the medical practitioner relating to the type of disease, and the energy level can be preset, which can also be subject to modification by the medical practitioner.

Treatment Methods

Thus, the alignment devices and methods described above are useful in combination with numerous treatment devices and compositions to treat a wide variety of conditions of the eye of a subject. Sources of treatment energy, such as electromagnetic energy emitting devices, can be utilized to implement corneal and/or non-corneal manipulations. According to the architectures and techniques of some embodiments of the invention, the source or sources (when utilized in combination) can be activated to direct energy onto and/or into parts of the eye, such as the conjunctiva and sclera to treat conditions such as presbyopia, wherein the energy affects at least one property of the eye and results in an enhancement in a property of the eye.

In some embodiments of the invention, focusing disorders such as myopia and hyperopia are treated. Myopia, or nearsightedness, relates to an eyesight refractive abnormality whereby distant objects appear blurred as a result of rays of light entering the eye being brought to focus in front of the retina. Hyperopia, or farsightedness, on the other hand, relates to an eyesight refractive abnormality whereby near objects appear blurred or fuzzy as a result of light rays being brought to focus behind the retina.

In addition to myopia and hyperopia, presbyopia is typically associated with a person's lack of capacity to focus at near distances and which tends to develop and progress with age. Regarding this progression, presbyopia is thought to advance as the eye progressively loses its ability to accommodate or focus sharply for near vision with increasing age of the person. Accordingly, the condition of presbyopia generally signifies a universal decrease in the amplitude of accommodation of the affected person.

Myopia and hyperopia can be treated surgically using techniques including corneal interventions, such as reshaping a surface curvature of the cornea located inside of the limbus area, and non-corneal manipulations, such as altering properties of the sclera (which is located outside of the limbus area), ciliary muscle, zonules, or lens. An example of the former treatment includes ablating the surface of the cornea itself to form a multifocal arrangement (e.g., distance vision in one eye and reading vision in another eye according to a treatment plan referred to as monovision) facilitating viewing by a patient of both near and far objects. An example of the latter treatment includes introducing kerfs into portions of the sclera to thereby increase accommodation. Non-corneal interventions typically include temporarily removing or pulling back the subject's conjunctiva, using forceps and scissors and/or one or more of scalpels, cautery, plasma, and laser methods, followed by the actual non-corneal manipulations (e.g., forming kerfs in the sclera). After completing the kerfs, the conjunctiva is then typically sutured back into position.

Electromagnetic energy devices may include, for example, lasers emitting a wide range of wavelengths, such as lasers having wavelengths ranging, for example, from about 0.2 microns to about 3.1 microns. Exemplary laser beam sizes can range from about 0.005 mm up to about 1.0 mm, or 2.0 mm. Exemplary laser energy per pulse values can range from about 0.1 mJ to about 50 mJ depending on, for example, the pulse duration and the laser beam spot size. Typical pulse laser widths may range from about 150 nanoseconds to about 1000 microseconds. The areas to be treated can be pre-traced with a vascular laser or long pulse Er, Cr:YSGG, or long pulse Er:YAG, to minimize bleeding.

In one embodiment of the invention, radiotherapy is administered. Radiotherapy is particularly useful for treating macular degeneration. Macular degeneration is a condition where the light-sensing cells of the macula, a near-center portion of the retina of the human eye, malfunction and slowly cease to work. Macular degeneration is the leading cause of central vision loss in people over the age of fifty years. Clinical and histologic evidence indicates that macular degeneration is in part caused by or results in an inflammatory process that ultimately causes destruction of the retina. The inflammatory process can result in direct destruction of the retina or destruction via formation of neovascular membranes which leak fluid and blood into the retina, quickly leading to scarring.

Radiotherapy can be used in combination with other therapeutics for the eye. Radiotherapy can be used to limit the side effects of other treatments or can work synergistically with other therapies. For example, radiotherapy can be applied to laser burns on the retina or to implants or surgery on the anterior region of the eye. Radiotherapy can be combined with one or more pharmaceutical, medical treatments, and/or photodynamic treatments or agents. For example, radiotherapy can be used in conjunction with anti-VEGF treatment, VEGF receptors, steroids, anti-inflammatory compounds, DNA binding molecules, oxygen radical forming therapies, oxygen carrying molecules, porphyryn molecules/therapies, gadolinium, particulate based formulations, oncologic chemotherapies, heat therapies, ultrasound therapies, and laser therapies.

In some embodiments, radiosensitizers and/or radioprotectors can be combined with treatment to decrease or increase the effects of radiotherapy, as discussed in Thomas, et al., Radiation Modifiers: Treatment Overview and Future Investigations, Hematol. Oncol. Clin. N. Am. 20 (2006) 119-139; Senan, et al., Design of Clinical Trials of Radiation Combined with Antiangiogenic Therapy, Oncologist 12 (2007) 465-477; the entirety of both of these articles are incorporated by reference herein. Some embodiments include radiotherapy with the following radiosensitizers and/or treatments: 5-fluorouracil, fluorinated pyrimidine antimetabolite, anti-S phase cytotoxin, 5-fluorouridine triphosphate, 2-deoxyfluorouridine monophosphate (Fd-UMP), and 2-deoxyfluorouridine triphosphate capecitabine, platinum analogues such as cisplatin and carboplatin, fluoropyrimidine, gemcitabine, antimetabolites, taxanes, docetaxel, topoisomerase I inhibitors, Irinotecan, cyclo-oxygenase-2 inhibitors, hypoxic cell radiosensitizers, antiangiogenic therapy, bevacizumab, recombinant monoclonal antibody, ras mediation and epidermal growth factor receptor, tumor necrosis factor vector, adenoviral vector Egr-RNF (Ad5.Egr-TNF), and hyperthermia. In some embodiments, embodiments include radiotherapy with the following radioprotectors and/or treatments: amifostine, sucralfate, cytoprotective thiol, vitamins and antioxidants, vitamin C, tocopherol-monoglucoside, pentoxifylline, alpha-tocopherol, beta-carotene, and pilocarpine.

Antiangiogenic Agents (AAs) aim to inhibit growth of new blood vessels. Bevacizumab is a humanized monoclonal antibody that acts by binding and neutralizing VEGF, which is a ligand with a central role in signaling pathways controlling blood vessel development. Findings suggest that anti-VEGF therapy has a direct antivascular effect in human tissues. In contrast, small molecule tyrosine kinase inhibitors (TKIs) prevent activation of VEGFRs, thus inhibiting downstream signaling pathways rather than binding to VEGF directly. Vascular damaging agents (VDAs) cause a rapid shutdown of established vasculature, leading to secondary tissue death. The microtubule-destabilizing agents, including combretastatins and ZD6126, and drugs related to 5,6-dimethylxanthenone-4-acetic acid (DMXAA) are two main groups of VDAs. Mixed inhibitors, including agents such as EGFR inhibitors or neutralizing agents and cytotoxic anticancer agents can also be used.

Thus, the system of the present invention can be used in some embodiments to provide radiotherapy treatment. A treatment axis which provides a reference about which application of the radiation beams are applied can be coupled to or aligned with a system axis of the radiotherapy system, about which an x-ray source can be positioned, e.g., by being rotated. The x-ray source can rotate about the system axis of the radiotherapy device, about which the x-ray source can be rotated. The x-ray source can rotate about the system axis with or independent from an imaging subsystem and its corresponding axis. With the treatment axis aligned with the system axis, and with the coupling device engaging the eye, trajectories of the radiation beams can be determined to direct the radiation beams to be coincident with the target tissue of the eye of the subject. The defined space of the treatment axis, the system axis, the location of the coupling device, and the location of the x-ray source provides a confined coordinate frame that can be used, for example, for directing orientation and administration of the radiation beams.

In one embodiment of the invention, radiodynamic therapy is administered. Radiodynamic agents can be administered either systemically or into the vitreous; the region in the eye to be treated is then directly targeted with radiotherapy as described above. The targeted region can be precisely localized using the device of the invention and/or in combination with an eye model, and then radiation can be precisely applied to that region. Beam sizes of about 1 mm or less can be used in radiodynamic therapy to treat ocular disorders if the target is drusen for example. In other examples, the beam size is less than about 6 mm.

It is further contemplated that the system of the present invention can be utilized to treat a variety of types of cancer of the eye. Exemplary cancer treatments are described below. Intraocular melanoma starts from pigment cells called melanocytes, which are found in the part of the eye known as the uvea. The uvea includes the iris, which forms the colored part of the eye; the ciliary body, which helps change the shape of the lens inside the eye so that it can focus; and the choroid, which is a very deep layer of the eye. Though it is uncommon, uveal melanoma is the most common primary eye tumor in adults; approximately 1200 people are diagnosed with the disease each year in the United States. Factors associated with the disease's development include light skin color, environmental exposure and genetic predisposition. If the melanoma begins in the iris, it may appear as a dark spot on the eye. However, if it begins in the ciliary body or choroid, symptoms may appear as vision problems, if at all. In these cases, the disease is usually detected during a routine examination. Chances of recovery and response to treatment depend on the location of the melanoma and whether it has spread. Posterior uveal tract melanomas (those cancers arising from the ciliary body or the choroid—the deeper parts of the eye) are typically more malignant, with a five-year mortality rate of 30% when the tumor has spread to areas outside of the eye. Anterior uveal tract melanomas (those arising from the iris) have a 2% to 3% mortality rate over five years. Thus, in one embodiment of the invention, intraocular melanoma is treated using the system of the invention.

Standard treatment for intraocular melanoma typically includes surgical removal of the eye, or enucleation. Because of this procedure's effect on a patient's appearance, possible diagnostic uncertainties and the potential for the cancer to spread, alternative treatments have been introduced. These treatments include radiation with radioactive plaques, laser photocoagulation, transpupillary thermotherapy and cryotherapy. Also contemplated is proton beam therapy which has the ability to precisely target eye tumors without causing any serious damage to healthy tissue surrounding the eye.

Choroidal metastasis occurs when cancer spreads to the choroidal layer of the eye from another primary site, like the breast. In these situations, the goal of treatment is to improve the patient's quality of life by preserving vision and preventing removal of the eye. Chemotherapy, external beam radiation therapy and proton therapy in combination with the system described above are contemplated by the present invention for the treatment of choroidal metastasis such that the therapeutic treatment allows for retention of the eye, achieves a high probability of local control, and helps avoid vision loss and pain.

Retinoblastoma is an uncommon childhood cancer. It begins in the retina, and accounts for about 3% of cancers in children younger than 15 years—about 4 cases per million. It most often occurs before the age of two, with 95% of retinoblastoma diagnosed before the age of five. The tumor may affect one eye (about 75% of cases), or both eyes (25% of cases). More than 90% of retinoblastoma that does not spread beyond the eye will be cured. Retinoblastoma is sometimes caused by an inherited gene mutation; when it occurs in both eyes, it is always the result of a gene mutation. Treatment of retinoblastoma in accordance with the present invention contemplates a multidisciplinary approach, and involves treating the cancer as well as retaining vision. If the tumor is especially large, or if there is little expectation of retaining normal vision, surgery may be considered. Other options include cryotherapy, photocoagulation, chemotherapy, and radiation therapy. External beam radiation therapy with protons has been used in select cases to control tumors. Proton therapy in combination with the system of the invention is also contemplated by the present invention.

Choroidal hemangiomas are benign vascular tumors that are usually well contained, and may cause a decrease in visual abilities. Treatment of choroidal hemangiomas is meant to reduce fluid collection under the retina and decrease the size of the tumor. Standard treatment involves laser photocoagulation, which successfully reattaches the retina, but may not always completely destroy the tumor. In recent years, radioactive plaque treatment and proton beam radiation treatments have been used. Proton beam therapy shares the precise tumor targeting ability of radioactive plaques, and is therefore contemplated for use with the system of the present invention.

In addition to the cancer treatment methods described above, the invention also contemplates aligning and manipulating the eye so as to move critical structures away from the treatment axis to deliver therapeutic amounts of radiation to tumors outside, but near, the eye. Thus, in one embodiment of the invention, the system is used to position the eye for the treatment of extraocular conditions. In one embodiment of the invention, the device described above is utilized in combination with other therapeutics for the eye. For example, one or more therapy treatments such as cryotherapy, photocoagulation, chemotherapy, and radiation therapy can be utilized in combination with the system of the present invention to provide therapeutic treatment of the eye.

From the foregoing, it can be seen how various objects and features of the invention are met. While certain aspects and embodiments of the disclosure have been described, these have been presented by way of example only, and are not intended to limit the scope of the disclosure. The methods and systems described herein may be embodied in a variety of other forms without departing from the spirit thereof. All publications and patents cited herein are expressly incorporated herein by reference for the purpose of describing and disclosing systems and methodologies which might be used in connection with the invention.

It is claimed:

1. A method of determining when a subject's eye position is aligned with a reference axis in an external coordinate system, comprising:
    (a) determining positions of the sclera/cornea boundary (limbus) of the subject's eye in the external coordinate system,
    (b) from the positions of the sclera/cornea boundary determined in step (a) determining the center of the limbus of the subject's eye in the external-coordinate system,
    (c) determining the position of an image of a light beam reflected from a reflective surface associated with the subject's eye
    (d) determining that the subject's eye is aligned with the external-coordinate reference axis when the position of the reflection from step (c) is coincident with the center of the limbus from step (b).

2. The method of claim 1, wherein the reflective surface associated with the subject's eye includes one of a surface of the cornea, a surface of the lens of the eye, and the surface of the retina.

3. The method of claim 1, wherein the reflective surface associated with the subject's eye includes one of a surface of a contact member or contact lens disposed in contact with the surface of the eye, and a surface of a mirror or fiducial element positioned on a contact member disposed in on surface of the eye.

4. The method of claim 1, wherein said determining is carried out with the subject's head stabilized in a head restraint.

5. The method of claim 1, wherein step (a) includes recording an image of the subject's limbus by an optical detector, and step (b) includes fitting the limbus image to a circle, and determining the center point of the circle.

6. The method of claim 1, wherein determining steps (a)-(c) are carried out by an imaging system disposed in the external coordinate system.

7. The method of claim 6, wherein the reflection from the subject's eye is a first Purkinje image formed by reflection of a coherent or focused light beam off the anterior surface of the cornea of the subject's eye.

8. The method of claim 7, wherein the optical axis of the coherent or focused light beam is aligned with the imaging system.

9. The method of claim 1, which further includes generating an eye-alignment signal when the subject's eye position is aligned with the external-coordinate reference axis.

10. The method of claim 9, which further includes using the eye-alignment signal to attach an ocular positioning and stabilizing device to the subject's eye.

11. The method of claim 9, which further includes using the eye-alignment signal to activate a therapeutic beam aimed along a path having a known relationship with the external-coordinate reference system.

12. The method of claim 11, for use in treating macular degeneration, wherein the therapeutic beam is a low-energy collimated X-ray beam, and the therapeutic beam is aimed along a path that intersects the reference axis at a region of the subject's eye, and at an angle between about 10-45 degrees with respect thereto.

13. The method of claim 1, wherein the reference axis defines a geometric axis of the subject's eye, and the method further includes calculating and/or measuring the distance between the cornea and the retina along this axis.

14. The method of claim 1, for determining the position of intersection of the reference axis with the subject's retina relative to a structure of interest on the retina, which further includes the steps of:
    (e) determining the position of an image formed by reflection of the light beam in step (c) off the retina of the subject's eye, when the position of the reflection image from step (c) is coincident with the center of the limbus image from step (b),
    (f) passing a second coherent or focused light beam through the pupil of the subject's eye to reflect off a structure of interest in the retina, and (g) determining the position of the image of the reflection of the second beam in the external coordinate system, relative to the image from step (e) in the external coordinate system.

15. A method of defining a reference axis of a patient's eye in an external coordinate system, comprising
(a) determining the positions of the sclera/cornea boundary (limbus) of the subject's eye in the external coordinate system,
(b) from the positions of the sclera/cornea boundary in step (a) determining the center of the sclera/cornea boundary of the patient's eye in the external-coordinate system,
(c) determining the position of an image formed by reflection of a coherent or focused light beam from a reflective surface associated with the patient's eye,
(d) adjusting the position of the patient's eye until the position of the reflection image from step (c) is coincident with the center of the sclera/cornea boundary image from step (b), at which position an axis normal to the cornea at the corneal center defines the patient reference axis.

16. The method of claim 15, wherein the reference axis extends from the cornea to a position on the retina which is a maximum distance from the cornea.

17. The method of claim 15, which further includes superimposing the patient reference axis on a three-dimensional model of the eye by aligning the patient reference axis with a model reference axis.

18. The method of claim 15, for conducting a diagnostic or therapeutic procedure on the eye, which further includes positioning a beam of a diagnostic or therapeutic device at a selected position and angle with respect to the patient reference axis.

19. The method of claim 15, which further includes generating an eye-alignment signal when the patient's eye position is aligned with an external-coordinate reference axis.

20. The method of claim 19, which further includes using the eye-alignment signal to attach an ocular positioning and stabilizing device to the patient's eye.

21. The method of claim 20, which further includes using the eye-alignment signal to activate a therapeutic beam aimed along a path having a known relationship with the external-coordinate reference system.

22. The method of claim 15, for use in treating macular degeneration, wherein the therapeutic beam is a low-energy collimated x-ray beam, and the therapeutic beam is aimed along a path that intersects the reference beam in a macular region of the patient's eye, and at an angle between about 10-45 degrees with respect thereto.

23. The method of claim 15, for determining the position of intersection of the reference axis with the patient's retina relative to a structure of interest on the retina, which further includes the steps of:
(e) determining the position of an image formed by reflection of the light beam in step (c) off the retina of the patient's eye, when the position of the reflection image from step (c) is coincident with the center of the sclera/cornea boundary image from step (b),
(f) passing a second coherent or focused light beam through the pupil of the patient's eye to reflect off a structure of interest in the retina, and
(g) determining the position of the image of the reflection of the second beam in the external coordinate system, relative to the image from step (e) in the external coordinate system.

24. A system of defining a reference axis of a patient's eye in an external coordinate system, comprising
(a) a light source for directing a coherent or focused light beam on a reflective surface associated with the patient's eye,
(b) an imaging system for recording an image of the patient's limbus and an image formed by reflection of the coherent or focused light beam from the cornea of the patient's eye, and
(c) a processor operatively connected to the imaging system for
(i) from the image of the sclera/cornea boundary, determining the center of the sclera/cornea boundary of the patient's eye in the external-coordinate system, and
(ii) from the image of the reflection of the coherent or focused light beam off the reflective surface, determining when the position of the reflection image is coincident with the center of the sclera/cornea boundary image, at which position an axis normal to the cornea at the corneal center defines the reference axis.

25. The method of claim 24, wherein the system further includes a head restraint configured to stabilize the patient's head.

26. The system of claim 24, wherein the light source of (a) is a coherent light beam.

27. The system of claim 24, wherein the processor further operates to generate a signal when the coincidence condition in step (ii) is met.

28. The system of claim 27, wherein the processor further operates to generate positioning signals for positioning a diagnostic or therapeutic device at a selected position and angle with respect to the reference axis.

29. The system of claim 24, wherein said imaging system includes a CCD photodetector.

30. The system of claim 29, further comprising an image processor and wherein the processor operates in step (i) to fit the image of the sclera/cornea boundary to a circle, and find the center of the circle.

31. The system of claim 29, further comprising a second processor and wherein the processor operates in step (ii) to determine, at each eye position of the patient eye, whether the center of the patient eye sclera/cornea boundary is the same as the position of the reflection image from the cornea.

32. The system of claim 29, wherein the image system further operates to record reflections of a coherent or focused beam off of the surface of the retina, and the processor further operates to
(iii) determine the position of an image formed by reflection of the light beam in (c) off the retina of the patient's eye, when the position of the reflection image off the cornea step is coincident with the center of the sclera/cornea boundary image,
(iv) determine the position of an image formed by reflection of another coherent or focused light beam off a selected structure of interest in the retina, and
(v) determine the position of the image of the reflection of the other beam off the structure of interest in the external coordinate system, relative to the position of the image of the reflection off the retina along the reference axis.

33. A method of placing a patient's eye in alignment with a reference axis in an external coordinate system, comprising
(a) placing an ocular guide on a patient's eye,
(b) centering the guide with respect to the sclera/cornea boundary of the patient's eye,
(c) stabilizing the ocular guide on the eye by applying a negative pressure between the guide and eye, (d) moving the ocular guide, and thus patient's eye, until the ocular guide is aligned with the reference axis, thus to place the patient's eye in alignment with the reference axis.

34. The method of claim 33, wherein the ocular guide has an peripheral ring dimensioned to be contained within or substantially coincident with the sclera/cornea boundary of the patient's eye, and step (b) includes adjusting the position of the guide until the peripheral ring and sclera/cornea boundary are coaxially aligned.

35. The method of claim 34, wherein said adjusting in step (b) is carried out by manually positioning the ocular guide on the patient's eye.

36. The method of claim 33, wherein the negative pressure applied in step (c) is between 20-50 mm Hg.

37. The method of claim 33, wherein step (d) is carried out by position-controlled movement of an external arm pivotally attached to the guide.

38. The method of claim 33, which further includes applying a force that biases the external arm against the patient's eye.

39. The method of claim 33, wherein the ocular guide includes a reflector and step (d) includes directing a collimated beam at the reflector and adjusting the position of the guide until the collimated beam and its reflection off the guide mirror are along axes that are symmetrical with respect to the reference axis.

40. The method of claim 39, wherein the beam and reflection axes are coincident with the reference axis.

41. The method of claim 33, which further includes determining the extent to which the eye guide is centered with respect to the sclera/cornea boundary, recording the variation, if any, from true centering, and constructing a coordinate transform between the actual and centered positions of the eye guide, and step (d) includes applying the transform to the position of the eye guide, with just placed in an aligned position, to place the patient's eye in alignment with the reference axis.

42. The system of claim 33, wherein the eye guide comprises an eye-contact portion configured to operatively contact an anterior surface of the eye, and a support portion operatively engagable to the eye-contact portion, and wherein eye-contact portion and the support portion are configured to engage releasibly, the release being upon voluntary or involuntary motion by the patient.

43. The method of claim 33, wherein the ocular guide has a curved structure which is centered on an axis extending through the contact member, the ocular guide has an outer reflecting surface normal to and intersected by the center axis of the eye contact member, and step (d) includes directing a collimated beam at the reflecting surface and adjusting the position of the guide until the collimated beam and its reflection off the reflecting surface are along axes that are symmetrical with respect to the reference axis.

44. An image-guided ocular treatment system comprising
(a) a eye guide adapted to be placed on a patient's eye, and stabilized on the eye by the application of negative pressure between the eye guide and eye when the guide is approximately centered with respect the sclera/cornea boundary of the patient's eye,
(b) a camera for recording an image of the eye guide on the patient's eye,
(c) a guide-alignment assembly for detecting alignment between the eye guide, with such stabilized on a patient's eye, and an external-coordinate reference axis,
(d) an external arm pivotally attached to the eye guide to hold the eye at a position in which the eye guide is aligned with the external-coordinate reference axis,
(e) a processor operatively connected to the camera and guide-alignment assembly for
(i) determining from the image of eye guide and the sclera/cornea boundary, any variation from true centering of the eye guide on the patient's eye,
(ii) if variation from true centering is determined, constructing a coordinate transform between the actual and centered positions of the eye guide,
(iii) with the eye guide moved to and held at its aligned position, and applying the coordinate transform if necessary, determining the position of the eye with respect to the external-coordinate reference axis,
(iv) from the determination in step (iii) determining a treatment axis or axes along which a therapeutic beam will be aimed at a target region of the eye, and
(f) a display monitor operatively connected to the processor for displaying to the user, an image of the patient's eye and attached eye guide, information about the extent of alignment between the eye guide and reference beam, and a virtual image of the treatment axis or axis.

45. The method of claim 44, wherein the system further includes a head restraint configured to stabilize the patient's head.

46. The system of claim 44, wherein the processor includes stored fundus images, and operates to superimpose those images on the image of the patient's eye displayed on the monitor, allowing the user to view the areas of intersection of the therapeutic beam axes and fundus.

47. The system of claim 44, wherein the ocular guide comprises an eye-contact portion configured to operatively contact an anterior surface of the eye, and a support portion operatively engagable to the eye-contact portion, and wherein eye-contact portion and the support portion are configured to engage releasibly, the release being upon voluntary or involuntary motion by the patient.

* * * * *